US012419908B1

United States Patent
Edwards et al.

(10) Patent No.: US 12,419,908 B1
(45) Date of Patent: Sep. 23, 2025

(54) CALCIUM OR MAGNESIUM CHLORIDE SALT-BASED COMPOSITION

(71) Applicant: SENSORY CLOUD, INC., Boston, MA (US)

(72) Inventors: David A. Edwards, Cambridge, MA (US); Rachel Diane Field, Boston, MA (US); Thomas E. Devlin, Somerville, MA (US); Dennis Arthur Ausiello, Wellesley Hills, MA (US)

(73) Assignee: SENSORY CLOUD, INC., Boston, MA (US)

( * ) Notice: Subject to any disclaimer, the term of this patent is extended or adjusted under 35 U.S.C. 154(b) by 0 days.

(21) Appl. No.: 19/209,542

(22) Filed: May 15, 2025

Related U.S. Application Data

(60) Division of application No. 18/809,916, filed on Aug. 20, 2024, which is a continuation-in-part of application No. 18/769,136, filed on Jul. 10, 2024, which is a continuation of application No. 18/094,604, filed on Jan. 9, 2023, now abandoned, said application No. 18/769,136 is a continuation of application No. 17/139,401, filed on Dec. 31, 2020, now abandoned.

(60) Provisional application No. 63/428,622, filed on Nov. 29, 2022, provisional application No. 63/425,450, filed on Nov. 15, 2022, provisional application No. 63/401,948, filed on Aug. 29, 2022, provisional application No. 63/395,926, filed on Aug. 8, 2022, provisional application No. 63/331,398, filed on Apr. 15, 2022, provisional application No. 63/324,461, filed on Mar. 28, 2022, provisional application No. 63/297,927, filed on Jan. 10, 2022, provisional application No. 63/130,099, filed on Dec. 23, 2020, provisional application No. 63/121,448, filed on Dec. 4, 2020, provisional application No. 63/048,421, filed on Jul. 6, 2020.

(51) Int. Cl.
*A61K 33/14* (2006.01)
*A61K 9/00* (2006.01)
*A61K 45/06* (2006.01)

(52) U.S. Cl.
CPC ............ *A61K 33/14* (2013.01); *A61K 9/0043* (2013.01); *A61K 9/0073* (2013.01); *A61K 45/06* (2013.01)

(58) Field of Classification Search
CPC .............................. A61K 33/14; A61K 9/0073
See application file for complete search history.

(56) References Cited

U.S. PATENT DOCUMENTS

| | | | | |
|---|---|---|---|---|
| 5,863,563 | A * | 1/1999 | Scheele | A61P 11/00 514/579 |
| 10,111,883 | B1 * | 10/2018 | Garceau | A61K 31/437 |
| 2012/0058198 | A1 * | 3/2012 | Clarke | A61K 33/14 424/602 |
| 2014/0203097 | A1 * | 7/2014 | Edwards | B05B 11/0054 239/305 |

FOREIGN PATENT DOCUMENTS

WO WO-2021207155 A1 * 10/2021 .............. A61P 31/14

OTHER PUBLICATIONS

Lake "Sterility Requirement for Aqueous-Based Drug Products for Oral Inhalation" Federal Register, May 26, 2000, vol. 65, No. 103, p. 34082-34089 (Year: 2000).*

* cited by examiner

*Primary Examiner* — Bethany P Barham
*Assistant Examiner* — Judith Marie Kamm
(74) *Attorney, Agent, or Firm* — Knowles Intellectual Property Strategies, LLC; Patrea L. Pabst

(57) ABSTRACT

Hydration of a larynx and/or vicinity with a composition comprising a salt formulation (e.g., $CaCl_2$, $MgCl_2$, KCl and/or NaCl) can achieve prophylactic and/or therapeutic effects (e.g., cough suppression, improving voice quality, increasing pulse oxygen saturation and/or increasing mucosal vaccination effectiveness). The composition is administered as dry particles (e.g., aerosol) or as a liquid (e.g., solution, aerosol). The liquid can have a pH of 7.0 up to around 10.0, or preferably around 7.5 up to around 9.5, or more preferably around 8.0 up to around 9.0, or even more preferably 8.0 to 8.5 or most preferably around 8.0. The droplets can have a mass median aerodynamic diameter from approximately 8 μm to approximately 15 μm or from approximately 15 μm to approximately 500 μm. A therapeutic dose (e.g., 0.5 mg to 4.0 mg mass of salt) is administered in response to an indication. Such can employ an osmolitically active composition.

15 Claims, 29 Drawing Sheets

| PARTICIPANT NO. | TREATMENT GROUP (EXCLUDED FROM ANALYSIS) | AGE | GENDER (M/F) | BLOOD GROUP | CRP | CRP (DAY 3) | D DIMER | SYMPTOMATIC | FEVER? | COUGH? | DIFFICULTY BREATHING? | SMELL OR TASTE DIFFERENCE? | DIARRHEA OR VOMIT? | BODY PAIN? | TEMP. (F) | SpO2 | TEMP. (F) (2ND READING) | SpO2 (2ND READING) | TEMP. (F) (3RD READING) | SpO2 (3RD READING) |
|---|---|---|---|---|---|---|---|---|---|---|---|---|---|---|---|---|---|---|---|---|
| 1 | ACTIVE | 30 | F | | 6.4 | 1.2 | 271 | ASYMPTOMATIC | NO | YES | NO | NO | NO | YES | 98 | 96 | 98.2 | 96 | 98 | 98 |
| 2 | ACTIVE | 16 | F | | 1.1 | 0.5 | 215 | SYMPTOMATIC | YES | YES | NO | YES | NO | YES | 98.1 | 98 | 98.3 | 99 | 98.3 | 99 |
| 3 | CONTROL | 42 | M | O+ | 8.4 | 2.9 | 165 | SYMPTOMATIC | Y | Y | N | N | N | Y | 100 | 96 | 98 | 97 | 98 | 98 |
| 4 | CONTROL | 40 | M | O+ | 27.2 | 117.3 | 253 | SYMPTOMATIC | N | Y | N | Y | N | N | 99 | 97 | 98.3 | 96 | 98 | 97 |
| 5 | ACTIVE | 23 | M | O+ | 2.8 | 1.3 | 218 | SYMPTOMATIC | Y | N | N | Y | N | Y | 98.2 | 96 | 98.1 | 98 | 98.4 | 98 |
| 6 | ACTIVE | 45 | M | A+ve | 6.4 | 9.5 | 250 | SYMPTOMATIC | Y | Y | N | Y | Y | Y | 98 | 98 | 98.3 | 99 | 98 | 99 |
| 7 | ACTIVE | 41 | M | A+ve | 31.3 | 117.3 | 304 | SYMPTOMATIC | Y | Y | Y | N | N | Y | 98.2 | 98 | 98 | 99 | 98 | 99 |
| 8 | CONTROL | 28 | F | O+ | 1.9 | 6.9 | 198 | SYMPTOMATIC | Y | Y | N | N | N | Y | 98.3 | 99 | 98 | 98 | 98.4 | 99 |
| 9 | CONTROL | 39 | F | O+ | 25.4 | 2.2 | 290 | SYMPTOMATIC | Y | Y | N | N | Y | Y | 98 | 98 | 98.2 | 98 | 98.1 | 98 |
| 10 | CONTROL | 28 | F | O+ | 2.3 | 8.7 | 197 | SYMPTOMATIC | Y | Y | N | Y | N | Y | 99 | 96 | 98 | 96 | 98 | 98 |
| 11 | CONTROL | 47 | M | A+ve | 23.1 | 26.3 | 218 | SYMPTOMATIC | N | Y | N | Y | N | N | 98 | 97 | 98 | 96 | 98 | 98 |
| 12 | CONTROL | 41 | M | A+ve | 20.1 | 68.7 | 324 | ASYMPTOMATIC | N | Y | N | N | N | Y | 98.1 | 98 | 98.2 | 97 | 98.4 | 98 |

\* = EXCLUDED

FIG. 1K

| Disease Severity Classification | Subjective Symptom Score Day 0 | Day 1 | Day 2 | Day 3 | Day 4 | Day 5 | Received IV Antibiotic? | Received Steroids? | Outcome |
|---|---|---|---|---|---|---|---|---|---|
| MILD | 3 | 2 | 2 | | | | NO | NO | AFTER 2 DAYS, SHE WAS DISCHARGED |
| MILD | 3 | 3 | 2 | 2 | 2 | | NO | | DISCHARGED |
| MILD | 3 | 3 | 2 | 2 | | | N | N | DISCOMFORT WITH NASAL SPRAY; DISCHARGED |
| MODERATE | 4 | 4 | 3 | 3 | 3 | 2 | Y | Y | DISCHARGED |
| MILD | 3 | 2 | 2 | 1 | 1 | | N | | DISCHARGED |
| MILD | 3 | 3 | 2 | 2 | | | N | N | DISCHARGED |
| MILD | 4 | 4 | 3 | 2 | 2 | | Y | N | DISCHARGED |
| MILD | 3 | 3 | 2 | 2 | | | N | N | DISCHARGED |
| MILD | 3 | 3 | 2 | | | | N | N | DISCHARGED |
| MILD | 3 | 3 | 2 | | | | N | N | DISCHARGED |
| MILD | 3 | 3 | 3 | 3 | | | N | N | DISCHARGED |
| MILD | 3 | 3 | 2 | | | | N | N | DISCHARGED |

FIG. 1L

KEY TO FIG. 1K–1S

| | |
|---|---|
| 1K | 1L |
| 1M | 1N |
| 1O | 1P |
| 1Q | 1R | 1S |

FIG. 1M

| PARTICIPANT NO. | TREATMENT GROUP (EXCLUDED FROM ANALYSIS) | AGE | GENDER (M/F) | BLOOD GROUP | CRP | CRP (DAY 3) | D DIMER | SYMPTOMATIC | FEVER? | COUGH? | DIFFICULTY BREATHING? | SMELL OR TASTE DIFFERENCE? | DIARRHEA OR VOMIT? | BODY PAIN? | TEMP. (F) | SpO2 | TEMP. (F) (2ND READING) | SpO2 (2ND READING) | TEMP. (F) (3RD READING) | SpO2 (3RD READING) |
|---|---|---|---|---|---|---|---|---|---|---|---|---|---|---|---|---|---|---|---|---|
| 13 | ACTIVE* | 47 | M | | 115.5 | 53.7 | 291 | SYMPTOMATIC | Y | Y | Y | N | Y | Y | 98.1 | 97 | 97.8 | 96 | | |
| 14 | ACTIVE | 32 | M | A+ve | 11.5 | 27.8 | 248 | SYMPTOMATIC | Y | Y | N | N | Y | Y | 98 | 97 | 98 | 98 | 98.1 | 99 |
| 15 | ACTIVE | 20 | M | O+ve | 17.7 | 3.8 | 324 | SYMPTOMATIC | Y | Y | N | Y | N | Y | 98 | 96 | 98.3 | 98 | 98 | 98 |
| 16 | ACTIVE | 42 | M | O+ve | 35.2 | 5.9 | 409 | SYMPTOMATIC | N | Y | N | N | Y | N | 98.2 | 95 | 98 | 96 | 98.1 | 98 |
| 17 | ACTIVE* | 38 | M | O+ve | 28.8 | 146.6 | 229 | SYMPTOMATIC | Y | Y | Y | N | N | Y | 98.1 | 97 | 98 | 93 | | |
| 18 | CONTROL | 45 | F | O+ve | 7.9 | 8.94 | 244 | SYMPTOMATIC | Y | Y | Y | N | N | Y | 98 | 96 | 98.1 | 96 | 98 | 96 |
| 19 | CONTROL | 53 | F | B+ve | 5.2 | 9.7 | 187 | SYMPTOMATIC | Y | Y | N | N | Y | Y | 98 | 97 | 97.8 | 96 | 98.3 | 97 |
| 20 | CONTROL | 54 | F | – | 13 | 1.8 | 163 | SYMPTOMATIC | Y | N | N | N | N | Y | 99 | 98 | 98 | 98 | 98 | 99 |
| 21 | CONTROL | 44 | F | O-ve | 13.6 | 19.63 | 290 | SYMPTOMATIC | Y | Y | Y | N | Y | Y | 98.2 | 97 | 98.5 | 97 | 98.4 | 98 |
| 22 | ACTIVE | 37 | M | A+ | 3.2 | 37.9 | 201 | SYMPTOMATIC | Y | N | N | Y | N | Y | 99 | 97 | 99 | 95 | 98 | 98 |
| 23 | ACTIVE* | 45 | M | A+ | 214.5 | 24.4 | 357 | SYMPTOMATIC | Y | Y | N | N | Y | Y | 98 | 97 | 98.8 | 95 | 98 | 93 |
| 24 | ACTIVE | 24 | M | O+ve | 6.4 | – | 179 | ASYMPTOMATIC | Y | Y | N | N | N | Y | 98 | 97 | 98.1 | 98 | | |

* = EXCLUDED

| DISEASE SEVERITY CLASSIFICATION | SUBJECTIVE SYMPTOM SCORE DAY 0 | DAY 1 | DAY 2 | DAY 3 | DAY 4 | DAY 5 | RECEIVED IV ANTIBIOTIC? | RECEIVED STEROIDS? | OUTCOME |
|---|---|---|---|---|---|---|---|---|---|
| MODERATE | 4 | 3 | 3 | | | | Y | Y | ESCALATED/KLEBSIELLA INFECTION, CT SEVERITY 10/25 |
| MILD | 3 | 2 | 2 | | | | N | N | DISCHARGED |
| MILD | 2 | 2 | 2 | 1 | | | N | N | DISCHARGED |
| MILD | 3 | 3 | 3 | 2 | 2 | 2 | Y | Y | DISCHARGED |
| MODERATE | 4 | 4 | 4 | | | | Y | Y | ESCALATED |
| MILD | 3 | 3 | 2 | 2 | 2 | | Y | N | ESCALATED TO INCREASE D DIMER |
| MILD | 3 | 3 | 3 | 3 | 3 | 2 | Y | Y | STEROIDS WERE GIVEN FOR 5 DAYS |
| MILD | 2 | 2 | 2 | 2 | | | Y | Y | DISCHARGED |
| MILD | 3 | 3 | 2 | 3 | 2 | | Y | N | DISCHARGED-10/05/2021 |
| MODERATE | 3 | 3 | 3 | | | | N | Y | SHIFTED TO W-6 |
| MODERATE | 3 | 3 | | | | | Y | Y | SHIFTED TO ER ON 8/05/2021 |
| MILD | 3 | 1 | 1 | | | | N | N | DISCHARGED |

FIG. 1N

| PARTICIPANT NO. | TREATMENT GROUP (EXCLUDED FROM ANALYSIS) | AGE | GENDER (M/F) | BLOOD GROUP | CRP | CRP (DAY 3) | D DIMER | SYMPTOMATIC | FEVER? | COUGH? | DIFFICULTY BREATHING? | SMELL OR TASTE DIFFERENCE? | DIARRHEA OR VOMIT? | BODY PAIN? | TEMP. (F) | SpO2 | TEMP. (F) (2ND READING) | SpO2 (2ND READING) | TEMP. (F) (3RD READING) | SpO2 (3RD READING) |
|---|---|---|---|---|---|---|---|---|---|---|---|---|---|---|---|---|---|---|---|---|
| 25 | ACTIVE | 41 | M | – | 49.7 | 5.4 | 187 | SYMPTOMATIC | N | Y | Y | N | N | Y | 98 | 94 | 98.4 | 95 | 98.1 | 98 |
| 26 | ACTIVE | 29 | M | A+ve | 9 | 7.4 | 98 | SYMPTOMATIC | N | N | N | N | Y | Y | 98.2 | 97 | 98.4 | 99 | 98.1 | 99 |
| 27 | CONTROL | 53 | F | O+ve | 95.9 | 48.95 | 187 | SYMPTOMATIC | Y | Y | N | Y | N | Y | 98 | 95 | 98.2 | 95 | 98.1 | 97 |
| 28 | CONTROL | 57 | F | | 2.8 | 1.3 | 290 | SYMPTOMATIC | Y | Y | Y | Y | Y | Y | 98 | 96 | 97.9 | 98 | 98.3 | 96 |
| 29 | ACTIVE | 55 | M | B+ve | 66.5 | 10.61 | 220 | SYMPTOMATIC | Y | Y | N | Y | N | Y | 98 | 96 | 98.2 | 99 | | |
| 30 | ACTIVE | 33 | M | O-ve | 5.7 | 1.3 | 170 | SYMPTOMATIC | Y | Y | Y | Y | Y | N | 98 | 97 | 98 | 99 | 98 | 99 |
| 31 | CONTROL | 33 | M | A+ve | 85.2 | 15 | 189 | SYMPTOMATIC | Y | Y | Y | Y | Y | Y | 98 | 97 | 98.1 | 97 | 98.2 | 96 |
| 32 | CONTROL | 50 | F | – | 12.52 | 7.76 | 204 | SYMPTOMATIC | Y | Y | N | N | Y | Y | 98 | 96 | 98.4 | 98 | 98.1 | 97 |
| 33 | CONTROL | 44 | F | – | 3.67 | 8.81 | 213 | SYMPTOMATIC | Y | Y | N | N | Y | Y | 98.5 | 98 | 98.5 | 98 | 98 | 98 |
| 34 | CONTROL* | 33 | F | | | | | ASYMPTOMATIC | Y | N | N | Y | Y | Y | | | | | | |
| 35 | CONTROL | 48 | M | A+ve | 0.7 | 0.5 | 224 | SYMPTOMATIC | Y | Y | N | N | N | Y | 98 | 99 | 98 | 98 | 98 | 99 |
| 36 | CONTROL | 30 | M | O+ve | 31.1 | 35.8 | 234 | SYMPTOMATIC | Y | Y | N | Y | N | N | 98 | 98 | 98.1 | 95 | 98 | 95 |

\* = EXCLUDED

FIG. 10

| DISEASE SEVERITY CLASSIFICATION | SUBJECTIVE SYMPTOM SCORE DAY 0 | DAY 1 | DAY 2 | DAY 3 | DAY 4 | DAY 5 | RECEIVED IV ANTIBIOTIC? | RECEIVED STEROIDS? | OUTCOME |
|---|---|---|---|---|---|---|---|---|---|
| MODERATE | 2 | 2 | 1 | 1 | | | N | N | DISCHARGED-8/05/2021 |
| MILD | 3 | 3 | 3 | 2 | 2 | | Y | N | DISCHARGED-11/05/2021 |
| MODERATE | 3 | 3 | 3 | 3 | 2 | | Y | Y | DISCHARGED |
| MILD | 3 | 3 | 2 | 2 | | | N | N | DISCHARGED-10/05/2021 |
| MILD | 3 | 2 | 1 | | | | N | Y(ORAL 1 DOSE) | DISCHARGED-11/05/2021 |
| MILD | 3 | 2 | 2 | 1 | | | N | N | DISCHARGED-14/05/2021 |
| MILD | 4 | 3 | 3 | 3 | | | N | Y | DISCHARGED |
| MILD | 3 | 2 | 2 | | | | N | N | DISCHARGED |
| MILD | 3 | 2 | 2 | | | | N | N | DISCHARGED |
| MILD | 3 | 3 | 2 | | | | N | | DISCHARGED-14/06/2021 |
| MILD | 3 | 3 | 3 | 2 | | | N | | DISCHARGED-17/06/2021 |
| MILD | 4 | 4 | 3 | 3 | | | Y | | DISCHARGED |

FIG. 1P

| PARTICIPANT NO. | TREATMENT GROUP (EXCLUDED FROM ANALYSIS) | AGE | GENDER (M/F) | BLOOD GROUP | CRP | CRP (DAY 3) | D DIMER | SYMPTOMATIC | FEVER? | COUGH? | DIFFICULTY BREATHING? | SMELL OR TASTE DIFFERENCE? | DIARRHEA OR VOMIT? | BODY PAIN? | TEMP. (F) | SpO2 | TEMP. (F) (2ND READING) | SpO2 (2ND READING) | TEMP. (F) (3RD READING) | SpO2 (3RD READING) | DISEASE SEVERITY CLASSIFICATION | SUBJECTIVE SYMPTOM SCORE DAY 0 | DAY 1 |
|---|---|---|---|---|---|---|---|---|---|---|---|---|---|---|---|---|---|---|---|---|---|---|---|
| 37 | CONTROL | 29 | M | B+ve | 34.8 | 7.5 | 221 | SYMPTOMATIC | N | Y | Y | Y | N | N | 100 | 95 | 97.1 | 95 | 97 | 94 | MILD | 4 | 4 |
| 38 | ACTIVE | 46 | M | A+ve | 45.4 | 29.8 | 324 | SYMPTOMATIC | Y | Y | N | Y | N | Y | 98.6 | 96 | 101 | 98 | 97 | 98 | MILD | 4 | 4 |
| 39 | ACTIVE | 29 | F | B+ve | 1.19 | 0.4 | 261 | SYMPTOMATIC | Y | Y | Y | Y | Y | Y | 99.6 | 95 | 97.6 | 99 | 97 | 99 | MILD | 4 | 4 |
| 40 | ACTIVE | 42 | M | A+ve | 23.7 | 4.9 | 403 | SYMPTOMATIC | Y | Y | N | N | N | N | 100 | 97 | 98 | 98 | 97 | 98 | MILD | 3 | 3 |

| DAY 2 | DAY 3 | DAY 4 | DAY 5 | RECEIVED IV ANTIBIOTIC? | RECEIVED STEROIDS? | OUTCOME |
|---|---|---|---|---|---|---|
| 2 | 2 | | | Y | | DISCHARGED-16/06/2021 |
| 2 | 2 | | | N | | DISCHARGED |
| 1 | 1 | | | N | | DISCHARGED |
| 1 | 1 | | | N | | DISCHARGED |

FIG. 1S

| RH | T=1s | T=2s | T=5s | NOSE OR MOUTH | REST OR EXERCISE |
|---|---|---|---|---|---|
| X (DEHYDRATION FACTOR) | | | | | |
| 10% | 0.2 | 0.2 | 0 | N | R |
| 60% | 0.1 | 0.1 | 0 | N | R |
| 10% | 0.3 | 0.2 | 0.2 | M | R |
| 60% | 0.2 | 0.1 | 0.1 | M | R |
| 10% | 0.3 | – | – | M | E |
| $Q_ET(mg)$, $RH_{INH}$ | | | | | |
| 10% | 3.2, 24% | 6.4, 40% | 16, 88% | N | R |
| 60% | 1.6, 53% | 3.2, 61% | 8, 85% | N | R |
| 10% | 1.2, 10% | 2.4, 20% | 6, 38% | M | R |
| 60% | 0.6, 48% | 1.2, 51% | 3, 60% | M | R |
| 10% | 6.0, 38% | – | – | M | E |
| AIR GENERATION $V_{SAT}$ (cm$^3$) | | | | | |
| 10% | 16, 138 | 16, 130 | 11, 60 | N | R |
| 60% | 14, 100 | 14, 90 | 11, 70 | N | R |
| 10% | 17, 180 | 16, 150 | 16, 130 | M | R |
| 60% | 16, 150 | 14, 100 | 14, 90 | M | R |
| 10% | 16, 130 | – | – | M | E |
| PCL THICKNESS CHANGE d (μm) | | | | | |
| 10% | 0.2 | 0.2 | 0 | N | R |
| 60% | 0.1 | 0.1 | 0 | N | R |
| 10% | 0.3 | 0.2 | 0.2 | M | R |
| 60% | 0.2 | 0.1 | 0.1 | M | R |
| 10% | 1.5 | – | – | M | E |

FIG. 8

| RH | T=1s | T=2s | T=5s | NOSE OR MOUTH | REST OR EXERCISE |
|---|---|---|---|---|---|
| $(C_{ATP0}-C_{ATP0})/C_{ATP0}$ | | | | | |
| 10% | 1.9 | 2.0 | 0 | N | R |
| 60% | 0.1 | 0.5 | 0 | N | R |
| 10% | 0.2 | 3.0 | 6.0 | M | R |
| 60% | 0.5 | 0.5 | 1.0 | M | R |
| 10% | 9.0 | – | – | M | E |
| $(Cl-Cl_0)/Cl_0$ | | | | | |
| 10% | 0.2 | 0.4 | 0 | N | R |
| 60% | 0.02 | 0.1 | 0 | N | R |
| 10% | 0.4 | 0.6 | 1.2 | M | R |
| 60% | 0.1 | 0.1 | 0.2 | M | R |
| 10% | 1.8 | – | – | M | E |
| $(CBF_0-CBF)/CBF_0$ | | | | | |
| 10% | 0.1 | 0.2 | 0 | N | R |
| 60% | 0.01 | 0.05 | 0 | N | R |
| 10% | 0.2 | 0.3 | 0.7 | M | R |
| 60% | 0.07 | 0.07 | 0.2 | M | R |
| 10% | 1.0 | – | – | M | E |
| $(EBP-EBP_0)/EPB_0$ | | | | | |
| 10% | 1.6 | 3.1 | 0 | N | R |
| 60% | 0.7 | 1.3 | 0 | N | R |
| 10% | 3.1 | 3.8 | 11.6 | M | R |
| 60% | 1.3 | 1.3 | 2.7 | M | R |
| 10% | 15.5 | – | – | M | E |
| $M_D(mg)$ | | | | | |
| 10% | 0.3 | 0.3 | 0 | N | R |
| 60% | 0.2 | 0.2 | 0 | N | R |
| 10% | 0.5 | 0.3 | 0.3 | M | R |
| 60% | 0.3 | 0.2 | 0.2 | M | R |
| 10% | 2.5 | – | – | M | E |

FIG. 10

| ASSUMPTIONS | VALUES | DESCRIPTION OF ENVIRONMENTAL MASS AND ENERGY TRANSPORT, AND BASIC PHYSICAL CONSENT ASSUMPTIONS |
|---|---|---|
| ENVIRONMENTAL | | |
| TEMPERATURE | 30°C | REPRESENTATIVE OF WARM EQUATORIAL AIR |
| RELATIVE HUMIDITY | 10-60% | TYPICAL MODERATE RANGE OF LOW TO HIGH HUMIDITY |
| MASS TRANSPORT | | |
| 3 COMPARTMENTS | | NOSE, TRACHEA AND CENTRAL AIRWAYS ARE PERFECT MIXING COMPARTMENTS |
| STEADY STATE | | ALL TRANSPORT HAPPENS AT OR NEAR A STEADY STATE IN REAL TIME OR OVER TIME AVERAGE |
| PERFECT MIXING | | AIRBORNE WATER MASS IN EACH COMPARTMENT IS PERFECTLY MIXED |
| ANION PERMEATION | | ANION TRANSPORT IS RAPID RELATIVE TO CATION TRANSPORT – MEMBRANES ARE HIGHLY PERMEABLE TO CHLORIDE ION TRANSPORT |
| QUIESCENT DOMINANT | | WATER EVAPORATION OVER THE ENTIRE SURFACE AREA OF THE NOSE IS DOMINATED BY QUIESCENT EVAPORATIVE LOSSES |
| CONVECTIVE DOMINANT | | WATER EVAPORATION OVER THE ENTIRE SURFACE AREA OF THE TRACHEA IS DOMINATED BY CONVECTIVE EVAPORATIVE LOSSES |
| TRACHEA AIR VELOCITY | 1m/s | THIS VALUE ASSUMES AIR FLOW OVER THE SURFACE OF THE TRACHEA IS DOMINATED BY LARYNGEAL JET OF AIR (PEAK 3s/m) |
| ENERGY TRANSPORT | | |
| UPPER AIRWAYS | | THE ENVIRONMENTAL AIR TEMPERATURE (30°C) IS RETAINED UP TO THE END OF THE TRACHEA OF THE CARINA |
| CENTRAL AIRWAYS | | FROM THE CARINA TO THE LAST GENERATION PRIOR TO FULL SATURATION OF THE AIR THE AIR A TEMPERATURE OF 35°C HOLDS |
| EVAPORATION ENERGY | | THE LOSS/GAIN OF ENERGY FROM THE ALF ON EVAPORATION/CONDENSATION HAS MINOR IMPACT ON MASS WATER FLOWS |
| PHYSICAL UA | | |
| TRACHEAL | R=1cm, L=12cm | CHARACTERISTIC OF TYPICAL REPORTED HUMAN TRACHEAS |
| UPPER AIRWAY AREAS | 160cm² (NOSE), 60cm² (TRACHEA) | CHARACTERISTIC OF TYPICAL REPORTED HUMAN NOSE AND TRACHEAL DIMENSIONS |
| ALF THICKNESSES | 30μm (TOTAL), 7μm (PCL), 23μm (MUCUS) | WITHIN THE RANGE OF REPORTED ALF THICKNESSES IN HYDRATED HUMAN UPPER AIRWAYS |
| ALF VOLUMES | 0.48cm³ (NOSE), 0.18cm³ (TRACHEA) | |
| ALF SALT CATION MASSES | 5.5mg Na+, 70μg Ca++, 7μg Mg++ | BASED ON ASSUMPTION OF EQUILIBRIUM OF ALF SALTS WITH WELL-HYDRATED (ISOTONIC SALT) CONCENTRATION IN SURROUNDING TISSUE |

FIG. 13

CALCIUM OR MAGNESIUM CHLORIDE SALT-BASED COMPOSITION

CROSS-REFERENCES TO RELATED APPLICATIONS

This application claims priority as a divisional of U.S. Ser. No. 18/809,916 filed Aug. 20, 2024, which is a continuation of U.S. patent application Ser. No. 18/094,604 filed Jan. 9, 2023, which claims priority to U.S. patent application Ser. No. 63/428,622 filed Nov. 29, 2022, U.S. patent application No. 63/425,450 filed Nov. 15, 2022, U.S. patent application Ser. No. 63/401,948 filed Aug. 29, 2022, U.S. patent application Ser. No. 63/395,926 filed Aug. 8, 2022, U.S. patent application Ser. No. 63/331,398 filed Apr. 15, 2022, U.S. patent application Ser. No. 63/324,461 filed Mar. 28, 2022, and U.S. patent application Ser. No. 63/297,927 filed Jan. 10, 2022, and this application claims priority as a continuation in part of Ser. No. 18/769,136, filed Jul. 10, 2024, which is a continuation of U.S. patent application Ser. No. 17/139,401 which was filed Dec. 31, 2020, which claims priority to U.S. patent application Ser. No. 63/048,421 filed Jul. 6, 2020, U.S. patent application Ser. No. 63/121,448 filed Dec. 4, 2020, and U.S. patent Ser. No. 63/130,099 filed Dec. 23, 2020.

FIELD

This disclosure generally relates to topical hydration treatments of a relatively non-hydrated larynx and trachea of a subject to reduce phonation threshold pressure and thereby one or more of: reduce or suppress cough incidence, improve voice quality increase pulse oxygen saturation, and/or treat one or more disorders or diseases (e.g., gastrointestinal esophageal reflux disease and the associated laryngopharyngeal reflux; asthma) of the subject and/or improve efficacy of mucosal vaccinations. Such can be achieved via a delivery of isotonic or hypertonic salt-based formulations or compositions breathed through the nose or mouth and that deliver into the nose or mouth at least approximately 0.3 mg of total salt (e.g., calcium, magnesium and/or possibly potassium and/or sodium chloride) or approximately 2.5 mg of total salt, and treatment protocols, devices, and articles suitable for the depositing at least approximately 0.1 mg of salt-based compositions to the larynx and other tissue surrounding or in the vicinity of the larynx in a respiratory tract of the subject.

BACKGROUND

Description of the Related Art

Applicant has previously described the use of salt-based compositions delivered to an upper respiratory tract of a subject to suppress or otherwise limit respiratory droplet generation which can, for example, occur through the breakup of airway lining fluid during respiration, coughing, sneezing, talking or even singing. The shed respiratory droplets may be drawn inwardly, deeper into the respiratory tract, of the subject, for example to the periphery of the lungs. Inhaled particles from the environment, for instance soot particles, may land on the upper airway lining mucus. Breakup of the mucus into respiratory droplets can carry these particles deeper into the lungs, promoting allergic responses or other respiratory ailments.

Various airborne respiratory diseases including severe acute respiratory syndrome-coronavirus-2 (SARS-CoV-2) transmit through the air by a combination of the large droplets exhaled when people cough or sneeze, and by the very small respiratory droplets people generate in their airways when they naturally breathe. How exhaled respiratory droplets vary between individuals, evolves over time within individuals, and changes with environmental conditions, e.g., the humidity of the air, as well as with the onset and progression of COVID-19 infection, is critical to clarifying the nature of COVID-19 transmission—and other highly-communicable airborne respiratory diseases, such as influenza and tuberculosis.

BRIEF SUMMARY

Applicants have determined that hydration treatments of a relatively dehydrated larynx and/or vicinity of the larynx of a subject can advantageously lower phonation threshold pressure (PTP), for example within 15 minutes of topical application and that the lowered PTP can persist, for example, for at least 90 minutes after administration, and possibly greater than 120 minutes after administration, in a way that is generally far more efficient, significant and faster than occurs on the drinking of water. Lowering phonation threshold pressure, a measure of the minimal pressure required to promote vibration of the vocal folds (and sound), improves air flow through the glottis, improves voice quality, and lowers cough incidence among those with laryngeal hypersensitivity. Hydration can be achieved by delivering into the nose or mouth of at least approximately 0.3 mg salt, or approximately 2.5 mg of 5% hypertonic salt (e.g., via the nose), and in a way that permits at least approximately 0.1 mg of salt to deposit in the larynx and trachea. This salt is preferably a divalent salt, for example one or a combination of the following two salts: calcium chloride, magnesium chloride—while it is also possible to use, alone or in combination with calcium and/or magnesium chloride, sodium chloride and/or potassium chloride. The salt can be administered or delivered in a dry form, as particles with a range of mass densities and sizes, while having a median aerodynamic size in the range of approximately 8 microns to approximately 15 microns. Alternatively the salt can be administered or delivered in a wet form, for example as a liquid solution to be gargled, or a mouth wash, or for example as a nasal spray, any of which can deposit at least 0.1 mg of salt in the larynx and trachea by passage from the nasal or oral cavity directly into the throat; or, most preferably, administered or delivered as a fine mist of droplets (e.g., an aerosol of droplets) with mass median aerodynamic diameters in the range of approximately 8 microns to approximately 15 microns, or more preferably having a median aerodynamic size in the range of approximately 9 microns to approximately 13 microns, approximately 9 microns to approximately 12 microns, approximately 8 microns to approximately 13 microns, approximately 8 microns to approximately 12 microns, that are breathed in through the mouth and/or nose and deposit by inertia and gravity in the larynx and its vicinity. It is noted that not only did approximately 50% of the total number of droplets in the aerosols of droplets have the aerodynamic diameters in the range of approximately 8 microns to approximately 15 microns, inclusive, but also approximately 50% of the mass of the aerosols of droplets was contained in the droplets having aerodynamic diameters in the range of approximately 8 microns to approximately 15 microns, inclusive. Alternatively, the salt can be administered or delivered in a wet form, as a mist of droplets (e.g., an aerosol of droplets) with mass median aerodynamic diameters in the range of approximately 15 microns or larger if accompanied during or following delivery by actions (e.g., head tilted backwards or lying prone) that induce post-nasal drip. In some instances, a typical salt solution mass deposited in the upper airways is approximately 10 mg, with approximately 3 mg deposited in trachea itself. In such instances, with a 5% salt solution approximately 0.5 mg to approximately 0.15 mg of salt (e.g., divalent salt) would be deposited per inhalation.

If administered or delivered in a wet form, the solution or droplets should have a pH of around 7.0 to around 10.0, and preferably be maintained at a pH of around 7.5 to around 9.5 or more preferably be maintained at a pH of 8.0 to around 9.0, or even more preferably 8.0 to 8.5 or most preferably around 8.0 to counter acidic conditions in the larynx that can promote laryngeal dysfunction. It is notably found that, whereas the larynx has a healthy pH of around 7, acidic conditions characterized by a pH below approximately 6, even below approximately 5, often afflict many people, with estimates based on a pH probe ranging from 10% to 60% of all normal subjects (Merati A L, Lim H J, Ulualp S O, Toohill R J. Meta-analysis of upper probe measurements in normal subjects and patients with laryngopharyngeal reflux. *Ann Otol Rhinol Laryngol.* 2005; 114(3):177-182). Since salt solutions commonly delivered to the nose and respiratory tract often have acidic pH (pH in the nose is normally found to be acidic given the high exposure to environmental airborne mass), for optimal PTP lowering associated with reducing cough, improving voice quality, improving oxygenation and/or addressing laryngeal symptoms of gastroesophageal reflux disease, a pH of the salt solution delivered to the larynx and trachea should be at least 7.0 up to around 7.2, which is typically near the upper range of airway lining fluid pH including in the distal airways, or even as high as a pH of around 7.5, a pH of around 8.0 or even a pH of around 10.0, beyond which can lead to airway lining fluid causticities indicative of respiratory disease. It is noted that the ocean has a pH of roughly 7.5-8.5 buffered by high concentrations of bicarbonate.

Described herein are various prophylactic, hygienic and/or therapeutic treatment protocols, devices, and articles suitable for the delivery of hydration, and in particular hydration via the depositing of a minimal salt mass of at least approximately 0.1 mg to the larynx and trachea in a respiratory tract of a subject for the purpose of reducing phonation threshold pressure for at least approximately 90 minutes and acting within 15 minutes post-administration to a human subject who, for example, is not breathing humid air of greater than 60% RH, has not consumed fluid within an 2, or preferably 3, or optimally after within 8 hours of administration and is not drinking fluids within the timeframe of PTP measurement.

Water is typically not "actively" transported in the body, but rather depends on osmotic gradients or hydrostatic pressure for its movement. The latter only plays a role in pathological states (i.e., congestive heart failure). In normal physiology, osmotic forces are the drivers of water movement. While the kidney relies on the insertion of "water channels" called aquaporins for rapid osmotic movement of water, the lung does not.

The upper airway is under unique hydration challenges, given its exposure to the vagaries of the external environment. Frequently the upper airways, particularly, where hydration of inhaled air occurs, dehydrate, causing osmotic stresses on epithelial cells; this can cause cells to shrink as they attempt to hydrate the airway lining fluid, and cause regulating of epithelial cell volume by the membrane transport typically of sodium and potassium ions. These stresses and fluxes can positively influence the health of the airways, especially when cyclical and supported by proper whole body hydration, while they can also lead to cell damage and inflammation in extreme and prolonged dehydration conditions.

Regulation of airway lining fluid volume is critical to respiratory health. The inventors have found that a condensation layer over airway mucus may play a role in this regulation. The evolution of the condensation layer in a range of breathing conditions is mathematically analyzed, and predicted consequences to airway structure and function is compared with published in vitro and human clinical data. As a consequence of the sustained breathing of dry air results in a steady-state displacement of the mucus toward the epithelium even without airway lining fluid volume loss. This displacement accompanies a thickening of the condensation layer, which otherwise disappears with impaired mucus and epithelial water permeation. In normal healthy lungs, mucus displacement toward the epithelium tends to be greatest at high minute volume as occurs in sustained strenuous exercise, and based on such inventors predict an eight-fold (7.9) rise in upper airway lining fluid ATP concentration, a two-fold (1.8) rise in inflammatory marker concentration (IL-1$\beta$, IL-6 and TNF-$\alpha$), a 40% decrease in cilia beat frequency, and a nine-fold (8.5) rise in exhaled breath particles. These predictions closely match experimental data from several published human clinical studies. Confirming published in vitro and human clinical data, the inventors have discovered that ATP concentration in airway lining fluid increases with increasing minute volume on the breathing of dry air owing to cilia stresses associated with the displacement of the mucus (thickening of the condensation layer) and attaining levels that provoke cough in asthmatics. Cough incidence grows linearly with the mouth breathing of dry (10% RH) air, rising in the case of asthmatics around 7 fold (6.7) as minute volume increases from 15 L/min to 100 L/min (from around 0.75 cough per minute to around 5 coughs per minute), while imparting negligible cough reflex in healthy human airways. Exhaled breath particles appear to be a relative measure of upper airway dehydration, rising two-fold (2.4) in normal healthy airways on the tidal mouth breathing of dry air relative to mouth breathing of humid air (60% RH). Rehydration can be achieved by the inhalation of approximately 2.5 mg of 5% hypertonic salt to the nose. Maintenance of the condensation layer appears to be beneficial to respiratory health.

The breathing of dry air deepens the severity of respiratory diseases from asthma and COPD to influenza and COVID-19. Dehydrated airways promote inflammation, mucus production, cilia dysfunction, and triggers of cough, notably ATP release and associated acidification of the airways. By these phenomena, and the associated reduction of mucociliary clearance of inhaled particles, dry upper airways amplify the health risks of dirty air, and are a contributing factor to the rising global tide of respiratory disease.

Respiratory disease is now the principal killer in low income countries for all age groups, from infants to the elderly. Alarmingly worsened by the ongoing COVID-19 pandemic, rates of respiratory disease in high income countries have already been rising for decades. Children are especially vulnerable to respiratory disease, as indicated by asthma attacks in the US among children relative to the general population. Among US children, who also tend to suffer from dehydration, black and non-black Hispanic children are most at risk of asthma, with black children three to four times more likely to die of asthma than non-black children. Children of color are also most dehydrated among all U.S. children.

The upper airways dehydrate in many natural ways. Adding to the impact of whole-body dehydration, mouth breathing, heavy breathing as occurs on sustained exercise, and the coldness and dryness of inhaled air, all contribute to drying out of the upper airways. Dehydration of the larynx is an especial threat given its proximity to environmental air dryness and the reality that fastest air flow within the airways occurs in the larynx on inhalation.

The condition of cystic fibrosis, where defects in the CFTR gene prevent chloride transport across epithelial cells, and between cells via the paracellular route, thereby preventing water transport into the airways, has long been studied as a condition of chronic and excessive airway dehydration. Among therapeutic approaches to relieve the symptoms of cystic fibrosis, rehydration of the airways by the delivery of hypertonic saline has proven particularly useful.

One of the primary roles of the upper airways is to humidify inhaled air. Water from tissues surrounding the airways transports through airway lining fluid (ALF) and into inhaled air by osmotic movement through micro-structured fluids, notably a layer of mucus that in healthy airways rests above a periciliary layer (PCL), within which cilia protrude from ciliated epithelial cells and beat the mucus toward the mouth.

The osmotic movement of water through the mucus, a hydrogel, is common to transpiring hydrogels in nature, as on the surfaces of plant leaves, where large osmotic pressures created to support water evaporation can pull water great vertical distances. The facility of water to transport across hydrogels is characterized by a physicochemical transport property of the hydrogel called the water permeability, which increases and decreases with various natural phenomena, such as dehydration (which tends to shrink the hydrogel). Shrinking and expansion of hydrogels, depending on their ionic nature (anionic or cationic), also occurs with acidification, and alterations in ion content type and concentration.

A condensation layer generally covers transpiring hydrogels, whose existence can be understood by way of a simple example. Imagine a hydrogel, of the nature of airway lining mucus, supported by an underlying layer of water (such as the PCL) over a solid or semi-solid barrier (such as an epithelial cell layer). The mucus-like hydrogel exists in contact with air and contains a salt, such as sodium chloride, at isotonic concentration, within anionic pores that are large relative to the size of the salt ions, while small relative to the electrostatic potential surrounding each ion. The anionic chloride ions therefore diffuse with relative freedom of motion while cationic sodium diffusion is restricted. Moisture in the air condenses onto the hydrogel surface through natural condensation, as in the sudden sweep of supersaturated air as occurs on an exhalation. This leads to deposition of a mass of water on the surface of the hydrogel, and immediate diffusion of sodium and chloride ions from the hydrogel into the condensation layer. An equal and opposite mass of water flows into the membrane. Once enough salt has diffused into the condensation layer to produce isotonic concentration, and an equivalent mass of water has moved by osmosis into the hydrogel, salt concentration in the condensation layer will be the same as in the pores of the hydrogel. On evaporation, which may be extreme with a sudden sweep of cold or dry air, as occurs over airway mucus on an inhalation of conditioned air, the mass of water in the layer diminishes, moving the surface of the condensation layer toward the mucus with salinity increase within the condensation layer. Since the sodium cations are partially restricted in their movement into the pores of the hydrogel, their concentration increases most significantly, driving diffusion into the pores, and the reverse movement of water into the condensation layer, the basic physics of osmosis. To supply water at sufficient rate to meet the rate of evaporation, very large osmotic pressures can arise—osmotic pressure exceeding 5000 atmospheres have been observed in natural hydrogels during evaporation in 40% RH air.

Condensation layers of this kind would appear to play a role in the function (humidification and filtration of inhaled air) and dysfunction (cough, clearance breakdown, vocal dysphonia, among others) of upper airway lining fluid, and relate to the rehydration efficacy of inhaled hypertonic salines.

The salt-based hydrating compositions generally described herein can be provided as a laryngeal hygiene prophylactic or even as a therapeutic (e.g., to resolve voice abnormalities or acutely relieve cough) in a variety of settings or dehydrating circumstances.

Dehydration or the breathing of dry air can reduce natural clearance of inhaled particles, while, where the larynx is directly concerned, can particularly harm vocal performance, promote cough and throat-clearing, and reduce blood oxygen ($O_2$) saturation levels. Abnormally low pH levels in the larynx or surrounding regions can result in cough, throat clearing, hoarseness and other physical problems, for example, as results from gastrointestinal esophageal reflux disease and more specifically from laryngopharyngeal reflux see www.ncbi.nlm.nih.gov/pmc/articles/PMC6194652/#B8. Such can also exacerbate asthma.

Traditionally, hydration is provided in relief of these laryngeal circumstances by drinking water or breathing humid air. Sometimes antacids are also given for acid reflux—while these do not immediately or directly resolve laryngeal acidity. These methods provide hydration and/or increased pH to exceedingly more tissues than the larynx and therefore are not as efficient or effective (e.g., leading to relatively small changes and requiring variable periods of time, see for instance Verdollini et al Journal of Speech and Hearing Research, Volume 37, 1001-1007, October 1994) as direct topical delivery of hydration. Attempts to directly and topically hydrate the larynx using aerosols (i.e., nebulized droplets with median aerodynamic diameters smaller than around 6 microns) have not succeeded in appreciably reducing PTP (e.g., pubmed.ncbi.nlm.nih.gov/20699338/ and pubmed.ncbi.nlm.nih.gov/26412295/.

Rapid targeted hydration, for example by nasal inhalation of aerosol of droplets of 8 microns to 15 microns, or more preferably having a median aerodynamic size in the range of, approximately 9 μm to approximately 13 μm, approximately 9 μm to approximately 12 μm, approximately 8 μm to approximately 13 μm, approximately 8 μm to approximately 12 μm, or alternatively by nasal spray delivery of an aerosol of droplets of approximately 15 μm or larger during or followed by actions (e.g., head tilted backwards or lying prone) that induce post-nasal drip, with salt-based water compositions or formulations generally described herein can be delivered to a subject (e.g., human) to significantly reduce PTP by at least 5%, or 10%, or sometimes 15%, 20%, 30% or more (the degree of diminution depending in part on the degree of hydration of the subject prior to airway hydration) within 15 minutes post administration and reduced PTP may persist for up to 90 minutes or 120 minutes or even longer, and thereby to lower cough and/or throat-clearing incidence, improve vocal performance, increase oxygen saturation, and/or treat one or more disorders or diseases for extended periods of time, for example in response to states of dehydration as occurs in the course of breathing dry air, a night of sleep without liquids, vocal performance, strenuous physical exertion, or the suffering of abnormal pH levels (e.g., due to gastrointestinal esophageal reflux disease).

In a normally hydrated individual the general flow of water as relates to the upper airways is from the peribronchial tissue into the airways. The evaporation of water in the upper airways that occurs to hydrate inhaled air, produces an osmotic pressure in favor of water egress into airway lining fluid. This flow of water keeps the airways hydrated, while the airways hydrate inhaled air preventing massive water loss from the lungs. In states of dehydration, as occurs on the breathing of dry air, strenuous exercise or singing, low body water content changes the flow of water from the airways into the surrounding tissues. This can lead to drying out of the upper airways and consequent constriction of the glottis promoting higher phonation threshold pressure, lower air flow, and notably in the vicinity of the larynx, cough provocation, exercise-induced glottal constriction and asthma attack.

It has been observed that hydration of the larynx can permit greater glottis aperture, better air flow, and ultimately lower phonation threshold pressure (PTP). Lower PTP has been found to correlate with better voice quality, and lower cough incidence for those with laryngeal hypersensitivity. Previous attempts to deliver hydration directly to the larynx have not succeeded to lower appreciably PTP as an insufficient mass of salt was delivered, e.g., by aerosol droplets with droplet median diameters smaller than around 6 microns, and therefore not targeted to the larynx and trachea. The nasal or oral breathing delivery of isotonic or hypertonic saline droplets of mass median aerodynamic diameter approximately 8 µm to approximately 15 µm, or more preferably having a median aerodynamic size in the range of, approximately 9 µm to approximately 13 µm, approximately 9 µm to approximately 12 µm, approximately 8 µm to approximately 13 µm, approximately 8 µm to approximately 12 µm, or, if accompanied or followed by post-nasal drip (e.g., head tilted back, prone position), approximately 15 µm to approximately 500 µm, can deposit within one to six breaths enough salt (greater than approximately 0.1 mg) to hydrate the tissue permitting greater air flow through the glottis and appreciably lower PTP, i.e., more than 5%, 10%, 15%, 20% or 25% reduction of PTP relative to PTP of the individual in a relatively dry larynx state. In other words, targeted upper airway hydration with sufficient quantities of salt in an isotonic or hypertonic solution can facilitate oxygenation, vocal performance, and cough reduction.

It is known that hypertonic salt solutions of sodium, potassium, calcium and magnesium chloride delivered to the airways promote hydration of the airways by osmotic pressures that pull water out of epithelial cells and into the airway lining fluid. Typically hypertonic salts delivered to the airways for hydration of the airways involve sodium chloride, and it is observed that the duration of hydration (as surmised by the speeding up of cilia beat frequency) is around 30 minutes up to 1 hour. Similar findings have also been observed based on the observation of exhaled aerosol diminution (Field et al 2021). It is, however, known that calcium ($Ca^{+2}$) and magnesium ($Mg^{+2}$) ions, among other roles, both compete for sodium channels in epithelial membranes and therefore transiently slow sodium ion movement through the membranes thus slowing down the speed of cell volume regulation (see, www.ncbi.nlm.nih.gov/pmc/articles/PMC22436/, www.ncbi.nlm.nih.gov/pmc/articles/PMC4468632/, and academic.oup.com/cardiovascres/article/81/1/72/277150) and the egress of sodium via the epithelial ion channels, keeping water in the air lining fluid longer. Calcium and magnesium, when delivered as a hypertonic salt solution or as dry salt particles, can therefore prolong the hydration of the airway lining fluid and thereby promote longer hydration of the larynx (and trachea and surroundings), and therefore prolonged suppression of cough, higher oxygenation, and prolonged vocal benefit, among other benefits. Hydration of the larynx reduces mechanical strain on cilia caused by restricted water volume and/or physical stress on phonation, reducing ATP release. P2X3 homotrimers have a primary role in cough. Ca and Mg cations can advantageously prolong an insensitive state of P2X3 receptors in the larynx, trachea and bronchus post release of ATP—these electrostatic interactions advantageously reduced by acidity (e.g., pH of the divalent (++) salts is pH 9 to 10 versus 6 to 7 for monovalent (+) salts. The divalent salts slow sodium ion diffusion via epithelial sodium ion channels prolonging hydration post osmotic challenge. Thus, hydration can advantageously lower PTP, 2-4 times longer with the divalent salts relative to the monovalent salts.

These insights have many consequences. Among other things it suggests that laryngeal targeted salt-based compositions generally described herein have major relevance to athletes, speakers and singers, and cough sufferers among others.

Droplet size of approximately 8 µm to approximately 15 µm, or more preferably having a median aerodynamic size in the range of, approximately 9 µm to approximately 13 µm, approximately 9 µm to approximately 12 µm, approximately 8 µm to approximately 13 µm, approximately 8 µm to approximately 12 µm, or alternatively approximately 15 µm to approximately 500 µm accompanied by an action (e.g., head tilted backwards, lying prone) promoting post-nasal drip into the larynx, can advantageously target the larynx. Particularly, droplets in the range of 1 to 7 µm tend to penetrate and deposit throughout the respiratory tract including in the alveolar region of the lungs. The generation of an aerosol with droplets in this size range requires more energy than the generation of an aerosol with the same mass of salt for delivery within droplets of say 10 µm or 50 µm or 200 µm in size, and therefore requires, for a given energy input, more time. Nasally or orally inhaled droplets of from 8 micron to 15 micron in size, or more preferably having a median aerodynamic size in the range of, approximately 9 microns to approximately 13 microns, approximately 9 microns to approximately 12 microns, approximately 8 microns to approximately 13 microns, approximately 8 microns to approximately 12 microns, and for example around 9 micron or around 10 micron in diameter predominantly deposit in the nasal or oral pharynx and in the larynx, trachea and main bronchi. On the other hand droplets of 15 micron to 500 micron can be inhaled or sprayed into the nose but tend to land in the nose and do not penetrate the trachea. In this case, tilt of the head or lying prone can promote post-nasal drip and hydrate the larynx.

Optimally, hypertonic calcium and/or magnesium chloride at the highest healthy hypertonicity for repeated use e.g., 2% or 3% or 4% or optimally 5% or even 6%, and without any other monovalent salt, will lead to the longest duration of hydration. Hypertonic salts of sodium and/or potassium chloride are also possible and can be delivered to the airways to improve hydration, while with shorter acting times than the divalent salts. When administered or delivered as solutions, all of these laryngeal hydrating salts can have a pH of the solution of 7.0 up to around 10.0, or preferably around 7.5 up to around 9.5, or more preferably around 8.0 up to around 9.0, or even more preferably 8.0 to 8.5 or most preferably around 8.0, with an aim to suppress coughing, improve vocal characteristics (e.g., reduce shimmer, reduce jitter, reduce vocal roughness), increase pulse oxygen saturation, and/or treat symptoms of one or more disorders or diseases (e.g., gastrointestinal esophageal reflux disease; asthma). In some implementations, the composition can be buffered, for example with a bicarbonate or citrate or phosphate or other buffer, to assure the desired pH level. In some implementations, the composition is stored in a sterile-fill container and is optionally free of any preservative, for instance filled in an oxygen-free environment. Other osmolitically active compositions may be effective and natural to the body, including large sugars, such as mannitol, sorbitol, and trehalose, while others, which are not advised, are either foreign to the body, as in the case of chitosan, or present in the body, as in the case of iron, while introducing other complex biochemical consequences.

Thus, one can hydrate the larynx to moisten the vocal folds, increase superficial water, and thereby lower PTP by around 5%, 10%, 15%, 20%, 25% or greater within roughly 15 minutes post-administration and for up to 90 minutes or even 120 minutes or more relative to a dehydrated larynx (e.g., in the absence of drinking fluids within two to eight hours of administration and during testing as well as a relative humidity no greater than around 60%) in order to: 1) increase air flow through the larynx (leading to increased pulse oxygen saturation); 2) improve voice quality; 3) reduce cough or throat-clearing incidence; and/or 4) increase laryngeal and possibly tracheal pH to treat negative consequences of acidity that are associated with one or more disorders or diseases (e.g., gastrointestinal esophageal reflux disease; asthma). The duration of effect is around 30 minutes (for sodium and potassium chloride) to around 90 or 120 minutes (with calcium and magnesium chloride), and for the latter salts may extend past 180 minutes.

A mister or nebulizer or spray pump that targets delivery of an aerosol of droplets to the larynx and vicinity of the larynx, and optionally the nose, may be particularly effective. The solvent (notably water), where included, and ions of the salt or salts in the droplets or alternatively as dry particles, may beneficially hydrate the larynx and tissues in the vicinity of the larynx, suppressing coughs, improving vocal characteristics and/or increasing pulse oxygen saturation; and/or increase laryngeal and possibly tracheal pH to treat negative consequences of acidity that are associated with one or more disorders or diseases (e.g., gastrointestinal esophageal reflux disease; asthma).

Prophylactically and/or therapeutically delivered hydration can deposit in the nose or other portions of the respiratory tract, depending on the nature of the delivery system and technique, with some associated degree of efficiency. This efficiency can be measured as a fraction of "delivered dose" to "nominal dose." The dosage administered or delivered (i.e., that which enters the nose or mouth) should be at least approximately 0.3 mg of total salt, and more preferably at least 0.5 mg of total salt or approximately 2.5 mg of total salt, and that the dosage deposited in the larynx and trachea be at least approximately 0.1 mg of total salt.

The described salt-based hydrating formulations or compositions are formulated in readily-soluble solutions applied to the nose as an installation or a spray, or in the form of aerosolized droplets (e.g., water droplets) that have a mass median droplet diameter range of approximately 8 microns to approximately 15 microns, with a standard deviation of less than 3 microns; alternatively the mass median droplet size is approximately 9 to approximately 13 microns, approximately 9.5 microns, or approximately 11 microns, with a standard deviation of 2 microns or less, or in some applications with a standard deviation of 1 micron or less. These droplet size ranges are advantageously too large for significant penetration into the lungs, while small enough to target the larynx and surround tissue. Otherwise, such solutions may applied to the nose as an inhalation or a spray, or in the form of aerosolized water droplets that have a mass median droplet size range of approximately 15 microns to approximately 500 microns, or a mass median droplet size range of approximately 50 to approximately 100 microns. In this latter case a head tilt for around 15 seconds to 2 minutes or lying prone for at least this same duration is sufficient to promote post-nasal drip delivery to the larynx. Finally, it is also possible to deliver the salts to the target tissues as an aerosol of dry particles, also with the mass median aerodynamic diameter range of approximately 8 microns to approximately 15 microns, with a standard deviation of less than 3 microns; alternatively the mass median aerodynamic diameter is, approximately 9 microns to approximately 13 microns, approximately 9 microns to approximately 12 microns, approximately 8 microns to approximately 13 microns, approximately 8 microns to approximately 12 microns, approximately 9.5 microns, or approximately 11 microns, with a standard deviation of 2 microns or less, or in some applications with a standard deviation of 1 micron or less.

The salt-based hydrating formulations or compositions may include one or more or all of sodium chloride, calcium chloride, magnesium, and/or potassium chloride, while preferably they include exclusively calcium and/or magnesium chloride. If delivered as solutions these compositions optimally maintain pH in the range of approximately 7 to approximately 7.5. Suitable salt-based hydrating formulations or compositions may, for example, include: salt solutions containing approximately 0.9%, approximately 2%, approximately 3%, approximately 4%, approximately 5%, approximately 6%, approximately 7%, approximately 8%, approximately 9% or approximately 10% by weight of the droplet of salt(s) including $CaCl_2$, $MgCl_2$, and/or KCl and/or NaCl.

Sodium, potassium and chloride are abundantly present in bodily tissues and their transport across airway epithelial membranes regulated to restore cellular volume relatively rapidly following hyper and hyposmotic challenges.

Calcium (see www.ncbi.nlm.nih.gov/pmc/articles/PMC4510619/, www.ncbi.nlm.nih.gov/pmc/articles/PMC5068478/) and magnesium (www.ncbi.nlm.nih.gov/pmc/articles/PMC4455826/) divalent cations are also abundantly present in bodily tissues and regulated in unique ways according to cellular needs including volume regulation (see journals.physiology.org/doi/full/10.1152/physrev.00037.2007, www.ncbi.nlm.nih.gov/pmc/articles/PMC4938024/), while membrane transports exist in airway epithelial cell membranes where variations of these divalent cations regularly occur and on time scales that generally differ from the monovalent ions of sodium, potassium and chloride.

The hydrating salt-based solution may also optionally contain one or more preservatives. Alternatively, the hydrating salt-based solution can be a sterile fill version packaged in an aseptic environment, and can thus be preservative free other than the salts themselves. The preservatives may include any preservative that would not otherwise interfere with the chemistry of the salts in the salt-based formulation. As one skilled in the art would appreciate, preservatives are on the FDA list of non-active agents. Suitable preservatives include benzalkonium chloride, benzyl alcohol, and benzoic acid. The preservative can be added in amounts known to those of skill in the art, for instance, 0.05-0.2 wt %, or about 0.1 wt %. Alternatively or additionally, the salt-based solution might also have low pH, through the addition of HCl or by some other means, e.g., pH in the range of about 2 to about 6; alternatively, about 2 to about 5; about 2 to about 3; or about 2.5. The HCl acid may be added with a citric acid buffer.

Application may be simple, for example one or more deep nasal inspirations may provide a suitable dosage to suppress coughing, improve vocal characteristics and/or increase pulse oxygen saturation for up to 90 minutes or more after administration. A protocol for administration may, for example include identifying an indication (e.g., laryngeal hypersensitivity syndrome, detecting a persistent cough or condition associated with persistent cough, detecting a vocal performance or scheduled vocal performance, detecting dehydration of a subject or portion thereof or detecting a physical exertion or planned physical exertion, for instance an upcoming race or other sporting or athletic event, or task or mission), and generating and administrating a dosage of a hydrating composition to a subject in anticipation of or during such conditions. Indications of a persistent cough can include any one or more of: persistent coughing, a runny or stuffy nose, postnasal drip, sore throat, hoarseness, frequent throat clearing, wheezing and/or shortness of breath. Indications of a vocal performance can include one or more of a vocal performance, a scheduled vocal performance (e.g., singing, speech or presentation, performance). Indications of a physical exertion or planned physical exertion can include one or more of: a race or other sporting or athletic event, a scheduled race or other sporting or athletic event, and/or a task or mission.)

An initial application (e.g., one, two, three, four, five or six deep nasal inspirations) may be administered by the subject or a staff member or other personal assigned to the specific task, for example prophylactically. A second application (e.g., one, two, three, four, five or six deep nasal inspirations) may follow, for example during coughing, during a vocal performance, or during an exertion. The second application may, for example, be self-administered. Self-administration may be performed from freely-accessible wall, and/or ground or table mounted nebulizers or misters. Alternatively, each individual (e.g., employee, patient, performer, athlete) may be supplied with a personal nebulizer or mister and an adequate supply of hydrating solution or dry powder to allow the individual to self-administer the hydrating aerosol of droplets, for example three times a day.

Thus, in some at least some implementations, proprietary compositions of natural salts and water with 7 micron to 15 micron mass median aerodynamic diameter droplets, preferably 8 micron to 13 micron mass median aerodynamic diameter droplets, or more preferably approximately 9 microns to approximately 13 microns, approximately 9 microns to approximately 12 microns, or approximately 8 microns to approximately 12 microns, or 10 micron to 11 micron mass median aerodynamic diameter droplets uniquely targets nose, larynx, and trachea to hydrate the same. While hypertonic salt treatments provide 30-60 minutes of hydration benefit, compositions described herein, at least some implementations, can extend benefit to several hours by natural modulation of epithelial sodium channel transport via divalent cations (Ca, Mg). While most nasal salines are acidic, compositions described herein, at least some implementations, have pH (7-7.2) for optimal laryngeal pH to avoid laryngeal hypersensitivity. The effectiveness of the compositions described herein can be demonstrated with measures of phonation threshold pressure (PTP) and exhaled aerosol. The compositions can, for example, reduce a phonation threshold pressure relative to a dehydrated state of an individual having avoided eating, drinking fluids, hydrating the airways or breathing air with relatively humidity of 50% or greater for approximately 2 hours, for example reducing the phonation threshold pressure such least 10% or more.

Application of a fine mist assures optimal coverage of sinus and olfactory bulb of the nose. Targeted hydration of the larynx can advantageously improve air flow optimization and reduce coughing. Targeted hydration of the trachea can advantageously improve particle clearance and reduce respiratory droplet formation Divalent cations (Ca, Mg) are advantageously natural stabilizers of desensitized state of P2X3 receptors.

In at least some implementations, the composition is sterile and free of preservatives, other than the natural salts themselves and optionally water, for example produced in pharmaceutical grade aseptic filing operation.

Various apparatus are also describe herein which allow the portable, discrete delivery of hydrating salt-based formulations or compositions, enhancing efficiency of delivery to humans and other animals on an individual basis. The apparatus may configured to be portable, allowing the user to have the benefit of on demand delivery, in a wide variety of environments, or it may be present in a physical environment and used by many as in the use of a hand sanitizing station.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIGS. 1K, 1L, 1M, 1N, 1O, 1P, 1Q, 1R, and 1S are a table illustrating data from a randomized double-blinded nasal-saline control study of 40 moderately symptomatic COVID-19 patients admitted into Bangalore Baptist Hospital during the period May-June when the delta variant predominated infections in India.

FIG. 8 is a table showing values of an airway dehydration factor $\chi$, according to at least one illustrated embodiment.

FIG. 10 is a table showing values of an airway inflammation factor I, following inhalation of dry (10% RH) air with an inhalation time T of 1, 2 or 5 seconds and a temperature at the carina of 35° C., according to at least one illustrated embodiment.

FIG. 13 is a chart showing basic assumptions of a biophysical model of hydration and dehydration of the human air waves, according to at least one illustrated implementation.

DETAILED DESCRIPTION

Figure 1A:
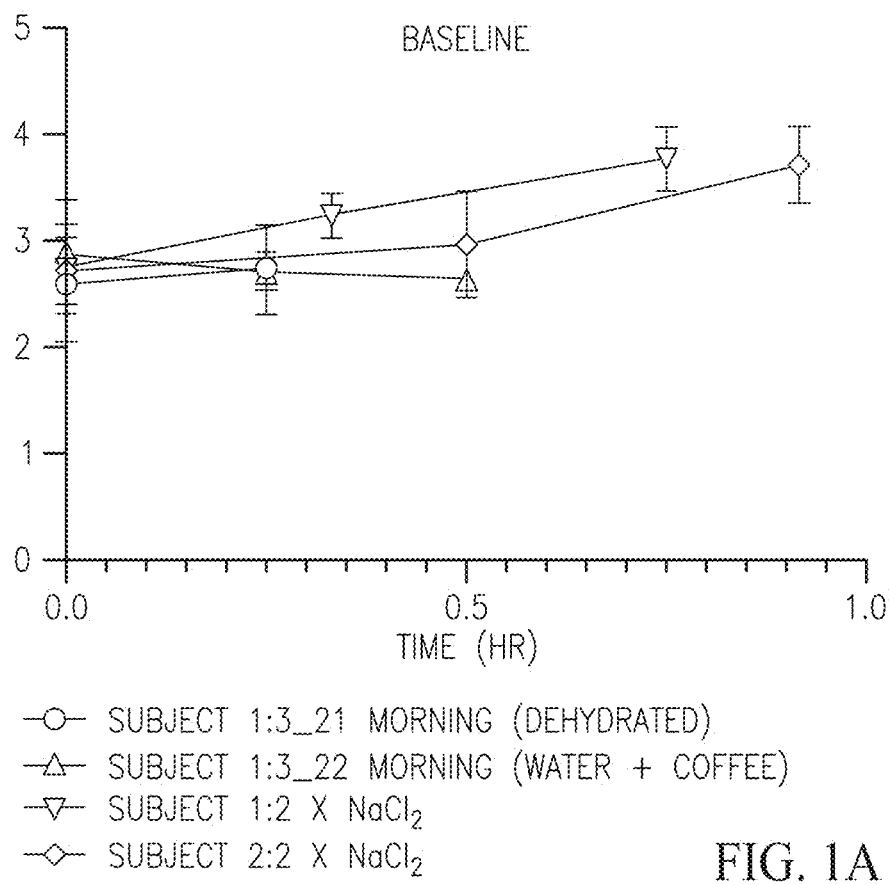
FIG. 1A is a graph showing baseline measurements of phonation threshold pressure (PTP) for two subjects, taken at several times on several different days with the subject experiencing different conditions on the various days as explained with reference to Example 1.
Figure 1B:
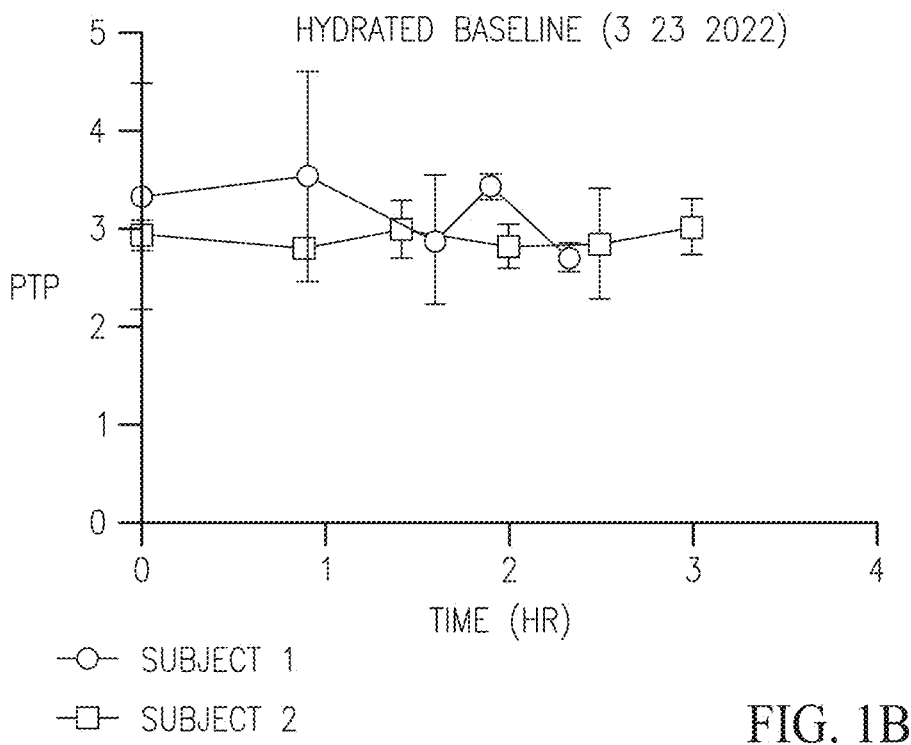
FIG. 1B is a graph showing hydrated baseline measurements of phonation threshold pressure (PTP) for two subjects, taken before and after the subjects drank an 8 ounce glass of water, and measured at several times after drinking the glass of water, and under conditions explained with reference to Example 1.

In the following description, certain specific details are set forth in order to provide a thorough understanding of various disclosed embodiments. However, one skilled in the relevant art will recognize that embodiments may be practiced without one or more of these specific details, or with other methods, components, materials, etc.

Unless the context requires otherwise, throughout the specification and claims which follow, the word "comprise" and variations thereof, such as, "comprises" and "comprising" are to be construed in an open, inclusive sense, that is, as "including, but not limited to."

Reference throughout this specification to "one implementation" or "an implementation" or to "one embodiment" or "an embodiment" means that a particular feature, structure or characteristic described in connection with the implementation or embodiment is included in at least one implementation or at least one embodiment. Thus, the appearances of the phrases "in one implementation" or "in an implementation" or "in one embodiment" or "in an embodiment" in various places throughout this specification are not necessarily all referring to the same implementation or embodiment. Furthermore, the particular features, structures, or characteristics may be combined in any suitable manner in one or more implementations or embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Described herein are new compositions, systems, methods, and articles of manufacture to advantageously deliver hydrating salt compositions to the larynx and/or trachea, e.g., via an aerosol of droplets to the larynx and/or tissue in the vicinity of the larynx, to reduce or suppress coughing, improve one or more vocal characteristics, and/or increase oxygen saturation levels; and/or increase laryngeal and possibly tracheal pH to treat negative consequences of acidity that are associated with one or more disorders or diseases (e.g., gastrointestinal esophageal reflux disease; asthma). The droplets have a pH of 7.0 up to around 10.0, or preferably around 7.5 up to around 9.5, or more preferably around 8.0 up to around 9.0, or even more preferably 8.0 to 8.5 or most preferably around 8.0, and can have a mass median aerodynamic diameter or size of approximately 8 µm to approximately 15 µm, approximately 9 microns to approximately 13 microns, approximately 9 microns to approximately 12 microns, approximately 8 microns to approximately 13 microns, or approximately 8 microns to approximately 12 microns. The droplets can, for example, be buffered to the specified pH level. The droplets can alternatively have a mass median aerodynamic diameter or size of larger than approximately 15 µm to approximately 500 µm, if accompanied by an action to induce esophageal penetration of the larynx or post-nasal drip. The droplets comprise water and a salt-based formulation or composition, and in particular physiological salt-based formulations or compositions. The salt formulations or compositions include optimally calcium and/or magnesium chloride, while they might also include sodium chloride, and/or potassium chloride. Dry powder formulations or mouth washes are also possible. If in the form of solutions, the hydrating salt compositions are optimally buffered to pH around 7.0 up to around 10.0, or preferably around 7.5 up to around 9.5, or more preferably around 8.0 up to around 9.0, or even more preferably 8.0 to 8.5 or most preferably around 8.0. Dry powder formulations can, for example, include one or more sugars, for instance trehalose or mannitol, which could be used to produce a hypertonic ALF with a dry powder formulation. The sugars can also advantageously function as good carriers for various drugs or pharmaceuticals (e.g., excipients, receptor targeting drugs or pharmaceuticals).

In particular, in the case of aerosols, a pump mister or alternatively a nebulizer can be used to generate an aerosol of droplets of specified size, specified tonicity, and/or specified dosage of salts, and delivery the same to target the larynx and tissue in the vicinity of the larynx. This may advantageously target the larynx and tissue in the vicinity of the larynx, hydrating such more efficiently than via other techniques.

The droplets are delivered as aerosol, and for instance taken in by the subject through the act of inspiration. When droplets with a relatively large size are employed (a mass median aerodynamic diameter or size of lager than approximately 15 µm to approximately 500 microns), the inspiration is accompanied or followed by an action to induce (when by the mouth) esophageal entry to the larynx or (when by the nose) post-nasal drip, for example a tilting of the head backwards or lying in a prone position. The aerosol can be dispensed in an unenclosed volume for instance the open air (e.g., in a room, out of doors), preferably reasonably proximate to a location of one or more individual's faces (e.g., positioned relatively in front of a nose of one or more subjects), without the use of an enclosed volume (e.g., mask, chimney, tumbler, vial, beaker or other container or vessel). Alternatively, the aerosol may be dispensed in an enclosed or partially enclosed volume (e.g., mask, chimney, tumbler, vial, beaker or other container or vessel). The individual(s) draw the aerosol in via the nose and/or mouth, for instance ortho-nasally and/or retro-nasally.

The salt-based compositions and formulations may comprise one, two, or more forms of physiological salts, which salts are dissolved in water. The salt-based compositions and formulations may, for example comprise any of one, two or more salts dissolved in water, and/or the salt or salts selected from the group consisting of: calcium chloride, magnesium chloride, and/or potassium chloride; preferably they include calcium and/or magnesium chloride. Ideal buffers are bicarbonate, citrate or phosphate-based. Each of the droplets can comprise at least 0.9% by weight of the droplet of salt, the salt comprising one, more or all of sodium chloride, and/or calcium chloride and/or magnesium chloride, and/or potassium chloride.

Administering the hydrating salt composition by whatever route (oral or nasal) or mode (fluid, droplets, dry particles) includes administering sufficient hydrating substance to achieve a delivery into the nasal or oral cavity of at least approximately 0.3 mg mass of salt(s), or approximately 0.5 mg mass of salt(s) or approximately 2.5 mg mass of salt(s), or up to approximately 30 mg of salt(s), and depositing into the larynx and trachea of at least approximately 0.1 mg mass of salt(s). Administering the hydrating aerosol of droplets can include administering sufficient droplets to achieve a delivery into the nasal cavity of from 0.3 mg to 2.0 mg mass of salt(s) (e.g., as determined by the known deposition pattern in the upper airways of a nasally inhaled cloud of droplets of the size characterizing the aerosol, and measuring the weight loss from a standing cloud of the mist held within a glass or vessel while a subject inhales deeply through the nose).

Administering the hydrating aerosol of droplets can include providing the aerosol of droplets in an enclosed volume, partially enclosed volume or open space for inspiration by a human. Administering the hydrating aerosol of droplets can include multiple inhalations and/or administering the aerosol of droplets for approximately 4 or 5 seconds to approximately 2 minutes to achieve a therapeutically effective dosage. Administering the hydrating aerosol of droplets can include inducing post-nasal drip, for example by tilting a head backwards or lying prone. Administering the hydrating aerosol of droplets can include inducing post-nasal drip, for example by tilting a head backwards or lying prone for approximately 15 seconds to approximately 2 minutes.

Described herein are various salt compositions incorporating calcium ions, and/or magnesium ions, and/or potassium ions and/or sodium ions, with chloride, which may be used to hydrate a larynx and surrounding tissue, for example to address the need for a broad prophylactic and/or therapeutic. Without being bound by theory, the inventor(s) hypothesized that an aerosol of droplets having a mass medium aerodynamic diameter or size of from approximately 8 μm to approximately 13 μm can be used to target the larynx and surrounding tissue. Without being bound by theory, the inventor(s) hypothesized that an aerosol of droplets having a mass medium aerodynamic diameter or size of from approximately greater than 15 μm to approximately 500 μm can be used to target the larynx and surrounding tissue if paired with actions to induce post-nasal drip. Droplet size can be measured via light scattering, for instance via light a scattering particle counter that measures particles that are 300 nanometers and larger, for example via laser diffraction using a Spraytec spray analysis system (Malvern Panlytical Ltd, UK) in an open-bench configuration in which the delivery device is affixed approximately 2" from the measurement beam, and Data collection occurs at a 1 kHz acquisition rate over the duration of the spray event, with reported results representing the time-averaged size distributions. The aerosol of droplets may advantageously include water and a salt formulation or composition comprising sodium chloride, and optionally including one, more or all of calcium chloride, magnesium chloride, and/or potassium chloride in addition to the sodium chloride, to improve hydration of the larynx and surrounding tissue in the vicinity of the larynx. Such can, for example, reduce or otherwise suppress coughing, improve vocal characteristics (e.g., shimmer, jitter), and/or improve pulse oxygen saturation levels of a subject to which the aerosol of droplets is administered. Such can, for example, increase laryngeal and possibly tracheal pH to treat negative consequences of acidity that are associated with one or more disorders or diseases (e.g., gastrointestinal esophageal reflux disease; asthma).

The impact of laryngeal hydration can be assessed by measurement of the Phonation threshold pressure (PTP), originally defined as oscillation threshold pressure (Titze, 1988), as the minimum lung pressure required to initiate vocal fold oscillation. It is based on an instability criterion for airflow in a soft-walled pipe that leads to flow-induced oscillation of the wall. It can be measured for instance by using the Aeroview System (Glottal Enterprises), a compact, non-invasive, accurate device and capable of recording oral airflow, nasal airflow, subglottal pressure and microphone data during speech.

Nasal Delivery Devices

Multiple delivery systems are possible for nasal sprays (e.g. SIMPLY SALINE™, a commercial nasal saline spray) or mouth washes (e.g. a glass or bottle). Multiple dry powder inhalers are also common for delivery of dry powders for inhalation to the respiratory tract including the upper airways.

Aerosol generators appropriate for generating the necessary droplet sizes of hydrating salt compositions are more specialized; two are described here. Both delivered similar droplet sizes by a similar maneuver of two deep nasal inhalations of the mist once generated before the nose. A pocket-size pump-spray device 700 (FIG. 5) functioned with a mechanical aerosol generator (AeroPump, Germany) by pressing the hydrating salt solution through laser-etched holes in a silica wafer followed by Rayleigh-Taylor instability that disintegrates into droplets of a specified size distribution (aerosol cloud of droplets 701). Another version of the pump-spray device 800 (FIG. 6) with a spacer to facilitate controlled dosing as is suitable for a regulated treatment product, is illustrated in FIG. 6 dispensing an aerosol cloud of droplets 801. A table-top nebulizer device 2100 (FIG. 7) which includes a vibrating mesh that turns ON upon tilting the device, promoting the generation of droplets of a specified size distribution (e.g., aerosol cloud of droplets 701 of FIG. 5, aerosol cloud of droplets 801 of FIG. 6). Emitted size distributions from the two delivery devices and the SIMPLY SALINE™ pump spray were determined via laser diffraction using a Spraytec spray analysis system (Malvern Panlytical Ltd, UK) in an open-bench configuration. The delivery devices were affixed approximately 2" from the measurement beam. Data collection occurred at a 1 kHz acquisition rate over the duration of the spray event, with reported results representing the time-averaged size distributions. All experimental conditions were assessed in triplicate. Another version of a pump spray (FIG. 6) that is suitable for dosing control incorporates a spacer around the nose.

Figure 7:
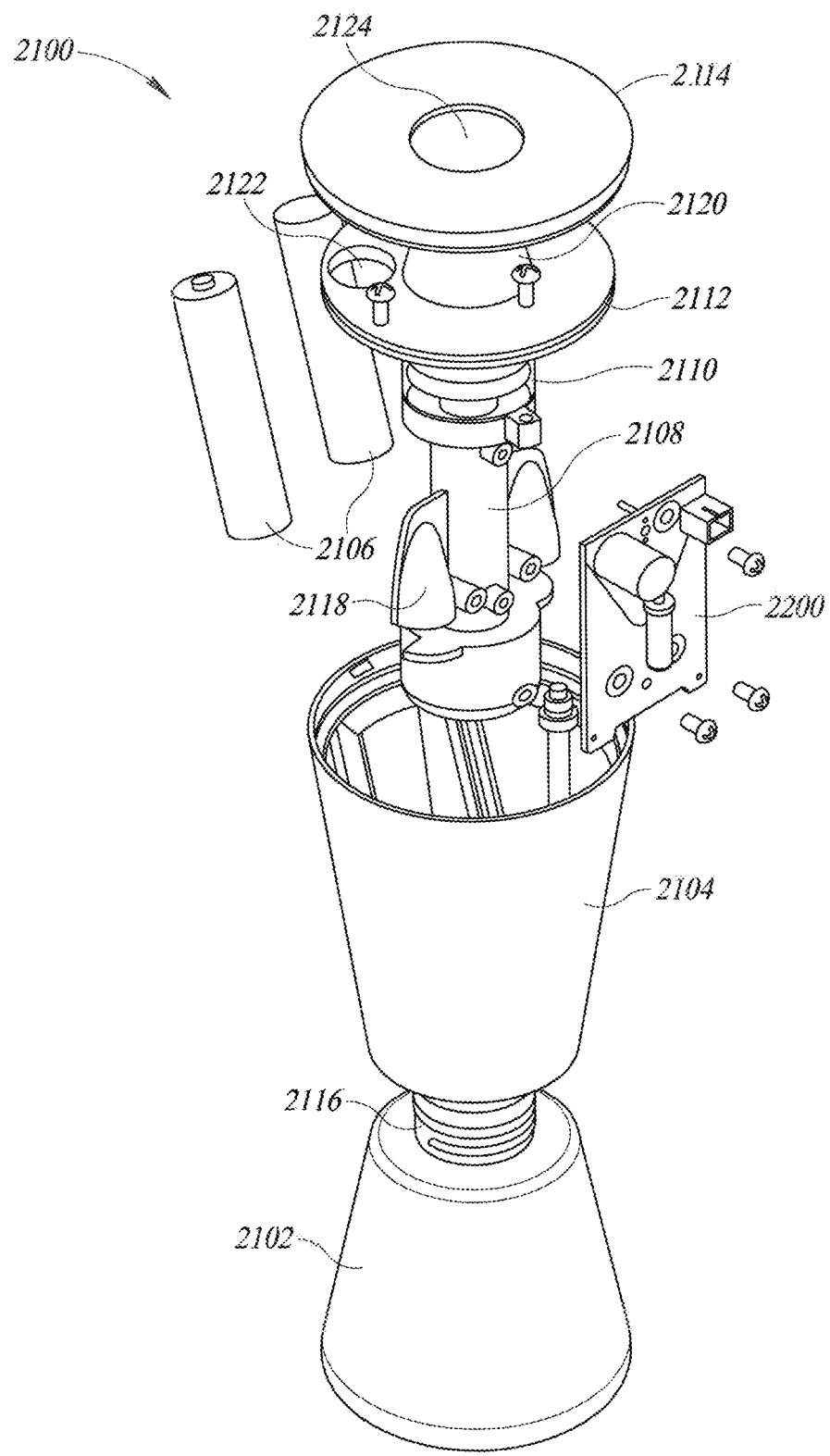
FIG. 7 is an illustration of a vibrating-mesh generator delivery system that can be used to deliver a mist, a cloud, or an aerosol comprising a salt-based formulation or composition that is effective to provide targeted hydration to a larynx of a human and to tissue in the vicinity of the larynx, according to at least one illustrated embodiment.

FIG. 7 illustrates a handheld NIMBUS™ nebulizer delivery device 2100 for producing and delivering a cloud of aerosolized droplets with a median size of from approximately 8μ to 12μ, the droplets comprising a solvent (e.g., water, ethyl alcohol, combination of water and ethyl alcohol) and a salt-based formulation or composition in aerosol form (e.g., suspension of droplets in air, for instance a suspension of small water droplets each comprising NaCl and optionally $CaCl_2$, $MgCl_2$ and/or KCl dissolved in the water of the droplets in the recited concentrations).

The hand-held nebulizer (NIMBUS™) operates on the basis of a vibrating mesh activated by two replaceable AAA batteries. The device is comprised of a head, which contains the piezoelectric vibrating mesh and on/off trigger, and a base or 1 oz. (30 mL) vial into which a solution comprising the solvent with the salt-based formulation or composition dissolved therein can be filled. The NIMBUS™ vial is detachable and made either of glass or plastic, full of sterile solution and discarded once empty. To evaluate delivered dose a 4-place balance (0.1 mg precision) was used along with the hand-held nebulizer. NIMBUS™ was inverted and cloud dispensed into a 6 ounce jar covered by a disk with a hole for cloud emission into the glass container. After ten seconds the cloud ceased to form, the NIMBUS™ was removed, the disk removed, and the weight of the glass determined. The "Discharged Dose" (n=5) results comprise measuring the entire 10-second emission into the jar through the coaster, and capping the coaster hole immediately after. The total emitted mass from the device was determined to be 57.0±2.1 mg. Approximately 22.1±1.5 of the dose deposited on the walls of the glass or ~39% of the emitted dose. Nasally delivered dose was assessed by two users affecting a single nasal inhalation from the glass post filling (n=5). The results 22.6 mg and 23.4 mg, respectively suggest a reproducible delivery of the solution and in the range of the target nasal dose.

The device 2100 can include any of the features of any of the other devices described herein, and can be used in combination with any of the other devices described herein. As illustrated in FIG. 7, delivery device 2100 includes a base 2102, which can be transparent and which includes a hollow container or tank or vial, in some cases having a volume or capacity of less than 100 mL, for holding a solution of a solvent with a salt-based formulation or composition dissolved therein in a liquid form. The base 2102 also includes an upwardly-extending hollow conduit, tube, or pipe 2116, through which the solution can be poured out of the base 2102 in a liquid form. An exterior surface of the conduit 2116 includes a set of threads.

The delivery device 2100 also includes a top or upper portion or main body 2104, which includes a hollow housing and the electronic and mechanical components of the delivery device 2100. Such components include a printed circuit board 2200 and associated components coupled thereto, a pair of batteries 2106, a hollow conduit, tube, or pipe 2108, a piezo-electric device 2110, which can include or be physically coupled to a mesh screen having a mesh size of 3 microns, of 4 microns, of 6 microns, of 20 microns, or of between 3 and 20 microns, as well as an internal cover 2112, and an external cover 2114, which can be transparent or translucent. The housing of the main body 2104 can be opaque or translucent, and can have a specific color such as red, orange, yellow, green, blue, purple, brown, black, or white. The internal cover 2112 can have an appearance matching that of the housing of the main body 2104. In particular, the internal cover 2112 can be opaque if the housing of the main body 2104 is opaque or translucent if the housing of the main body 2104 is translucent, and can have a specific color matching that of the housing of the main body 2104, such as red, orange, yellow, green, blue, purple, brown, black, or white.

The conduit 2108 includes a relatively wide top end portion, a relatively narrow middle portion and a relatively wide bottom end portion sized to extend around the conduit 2116 of the base 2102. An inner surface of the bottom end portion of the conduit 2108 includes threads complementary to the threads of the conduit 2116 so that the conduits 2108 and 2116 can be threadedly engaged and thereby coupled to one another. When the conduits 2108 and 2116 are coupled to one another, liquid salt-based antimicrobial and/or anti-contagion formulation or composition can be poured out of the base 2102 through the conduit 2116 and into the conduit 2108. The relatively wide top end portion of the conduit 2108 is sized and configured to house the piezo-electric device 2110 at the top end of the conduit 2108, so that a solution of the solvent with the liquid salt-based formulation or composition dissolved therein can flow through the conduit 2108 from the bottom end portion thereof to the piezo-electric device housed at the top end portion thereof.

The conduit 2108 also includes a pair of flanges 2118 that are coupled to opposing outer side surfaces of the middle portion of the conduit 2108, and that extend laterally outward from the respective side surfaces as well as in a direction aligned with the overall length of the conduit 2108. The flanges 2118 each include a recess or cradle that is shaped and configured to cradle a portion of one of the batteries 2106, to partially restrain the batteries 2106 when the device 2100 is assembled. The internal cover 2112 includes a generally circular or disk-shaped main body portion and a hollow and truncated cone-shaped portion 2120 that extends upward from the main body portion. The main body portion of the internal cover 2112 includes a pair of openings or apertures 2122 that extend through the main body portion. Each of the apertures 2122 is sized and configured to cradle a portion of one of the batteries 2106, to partially restrain the batteries 2106 when the device 2100 is assembled. The external cover 2114 includes a generally circular or disk-shaped main body portion and an opening or aperture 2124 that extends through the main body portion. The aperture 2124 is sized and configured to fit snugly around a portion of the outer surface of the cone-shaped portion 2120 of the internal cover 2112 when the device 2100 is assembled.

Alternatively or additionally, a dispenser may employ a structure (e.g., substrate) with one or more nozzles, the nozzles having orifices in the micron size range (e.g., 1 micron-30 microns). Such nozzles may take advantage of the Raleigh effect, passage through the micron sized range orifice causing a jet or stream of fluid to separate into a mono-disperse spray of droplets. Desired droplet size can be achieved by properly dimensioning the orifice(s), with the droplets generally being twice the size of the orifice. Thus, an orifice size in the range of 4 microns to 6 microns can achieve a median droplet size in the range of 8 microns to 12 microns, while a 4.5 micron orifice or a 5.0 micron orifice can achieve a median droplet size of 9 microns or 10 microns, respectively. The use of nozzles with micron sized orifices may advantageously reduce the variation between droplet size in an aerosol, leading or more uniformity and/or predictability of the amounts (e.g., mass) of an active substance (e.g., salt) delivered to a subject in a unit time. Multiple micron sized orifices may advantageously increase the number of droplets in an aerosol per unit of time. Nozzles with micron sized orifices can be obtained from Medspray of The Netherlands. The nozzle(s) be implemented as part of a mister with a reservoir and associated pump. Manual activation of the pump can drive fluid from the reservoir through the micron sized orifices.

Figure 5:
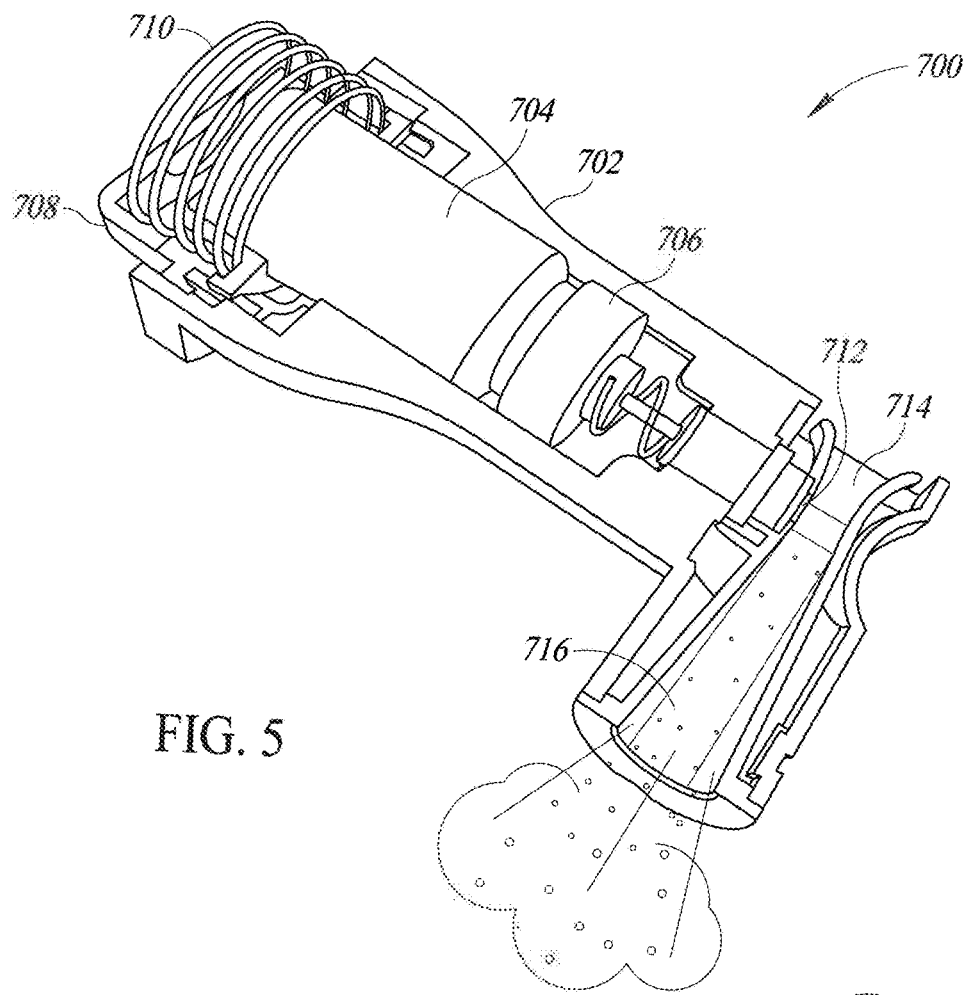
FIG. 5 is an exploded view of a pocket-size pump-spray delivery device to deliver a mist, a cloud, or an aerosol comprising a salt-based formulation or composition that is effective to provide targeted hydration to a larynx of a human and to tissue in the vicinity of the larynx, according to at least one illustrated embodiment.
Figure 6:
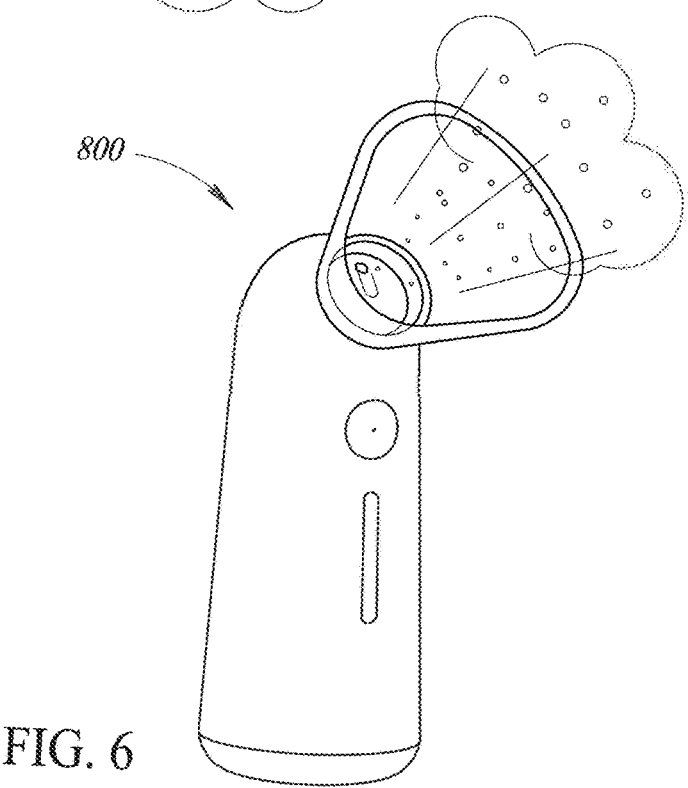
FIG. 6 is an exploded view of a pocket-size pump-spray delivery device with a spacer in which to position a nose of a user, to deliver a mist, a cloud, or an aerosol comprising a salt-based formulation or composition that is effective to provide targeted hydration to a larynx of a human and to tissue in the vicinity of the larynx, according to at least another illustrated embodiment.

FIG. 5 shows a spray pump 700 which can be used to generate and administer an aerosol of droplets, according to at least one illustrated implementation.

The spray pump 700 can include a body 702, that holds or houses a reservoir 704 with a metering valve 706. The reservoir 704 can be removable from the body, for refilling or replacement. The spray pump 700 can include a manual actuator 708 (e.g., button, trigger) that is coupled to the body 702 for movement with respect thereto (e.g., translation, rotation) and a bias mechanism 710 (e.g., spring, coil spring, leaf spring) that bias the manual actuator 708 away from an actuated position to an unactuated position. Actuating the manual actuator 708 to the actuated position can operate the metering valve 706 to cause liquid to be dispensed from the reservoir. Actuating the manual actuator 708 can, for example cause the metering valve 706 to dispense a measured amount of liquid from the reservoir, the measured amount equaling a dosage or a fraction of a dosage with an integer in the denominator (e.g., ½, ¼). The liquid can be dispensed either under a stored pressure where the liquid in the reservoir 704 is under pressure, or by creating pressure (e.g., a negative pressure of vacuum) to draw liquid from the reservoir 704. The spray pump 700 can include one or more spray nozzles 712, and optionally an air inlet 714 and an outlet with a Venturi channel 716.

The spray pump 700 can advantageously employ a substrate with a plurality of spray nozzles 712 with orifices having diameters on the micron scale (e.g., 1 micrometer to 30 micrometers) in order to generate Rayleigh jets. The spray pump 700 relies on the principle of Rayleigh break-up to generate droplets with a uniform droplet size on the order one to several tens of microns in size. Generally, the diameter of the droplets is twice the diameter of the orifice that generates the droplets. Thus, droplets of approximately 8 μm to 12 μm can be generated via spray nozzles with orifice diameters of 4 μm to 6 μm, respectively. Droplets with diameters of greater than approximately 20 μm can be generated via spray nozzles 712 with orifice diameters of greater than approximately 10 microns up until the principle of Rayleigh break-up fails. The spray nozzles 712 can be produced in a substrate using conventional micro- and nanotechnology fabrication processes and techniques.

All of these devices deliver a nominal dose of approximately 20-25 mg of solution per 4-5 seconds of actuation, the approximate time for a single deep nasal inhalation. Formation of a standing cloud of the aerosol in a glass container and nasal inspiration of the cloud (Edwards et al 2020) indicates that approximately 40% of the nominal dose is delivered into the nose. Practical delivered doses with standing clouds formed before the face in an unconstrained environments with the mist produced 2 inches from the nose will be less than 40%, and depending on user technique appear to typically range from 20-30%. According to Calmet et al (2019), a 10 micron aerosol inhaled into the nose deposits approximately 30% of the nasally delivered dose beyond the posterior region of the nose, i.e. into the larynx and trachea. The estimated nominal, delivered, and deposited doses of the hydrating salt solutions via these aerosol generates on a single nasal inhalation of 4 seconds therefore range from 20 mg (nominal), 5 mg (25% delivered), and 1.5 mg (30% deposited). In the case of a 5% salt solution, this translates into an estimated nominal, delivered and deposited dose of salt of 1 mg salt (nominal), 0.25 mg salt (delivered) and 0.075 mg salt (deposited). This suggests that per deep nasal inhalation with an approximately 10 micron droplet size the nominal, delivered and deposited salt doses range from 1 mg salt (nominal) to approximately 0.1-0.4 mg (delivered) (on average approximately 0.25 mg) and approximately 0.1 mg (deposited).

Discussion

Dehydration of the upper airways commonly occurs on the breathing of dry air or in dehydrated states of the human body (systemic dehydration), for instance lung disease, aging, high BMI, exercise, among other states including those following sleep during which little or no liquid intake has occurred. These circumstances harm the upper airway immune system and the ability to clear inhaled particles and efficiently process air flow.

Systemic dehydration depletes water in those upper airway regions of the lungs responsible for hydrating inhaled air, notably the nose, trachea and main bronchi. The lungs emit approximately 25% of daily total water mass loss in the process of hydrating inhaled air. This loss derives from a combination of water evaporation from upper-airway mucus on inspiration, and from exhalation of moist air from the lungs on expiration.

Alternating low and high humidity in the upper airways during tidal breathing creates a cyclical pattern of dehydration and rehydration that, when accompanied by systemic dehydration or the chronic breathing of dry air, can promote extreme thinning of upper airway lining fluid, reduce cilia beat frequency, and damage epithelial cells. These and other effects of airway dehydration reduce the ability of the upper airways to clear inhaled contaminants filtered out of the air by the upper airways and harm natural function to protect the gas exchange regions of the lungs. Chronic dehydration of the upper airways therefore exacerbates allergies, asthma, COPD and airborne infections including influenza and COVID-19.

Figure 2A:
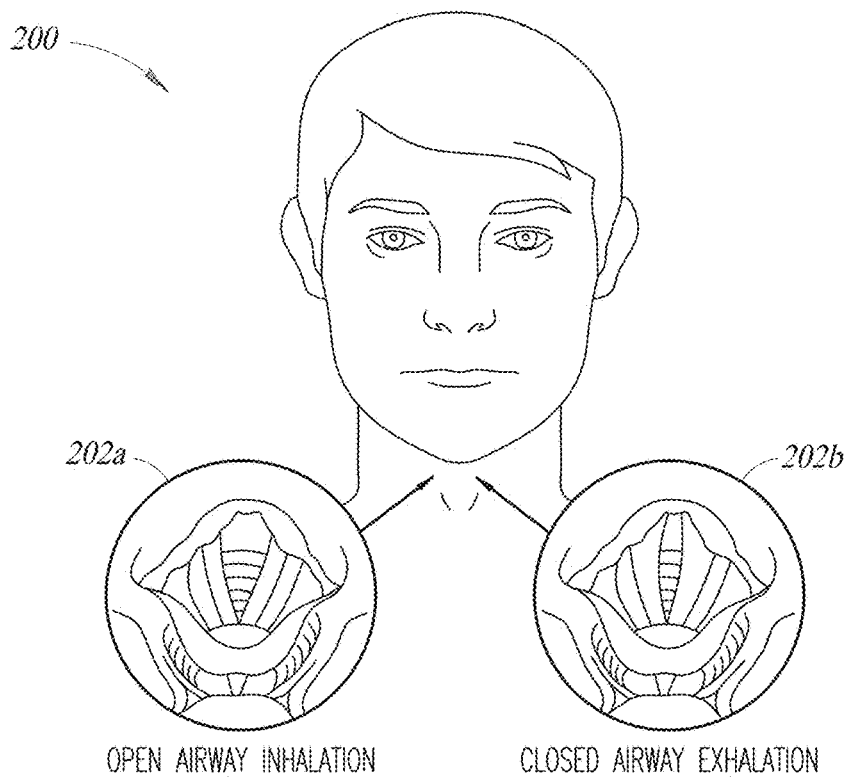
FIG. 2A is an illustration showing a human subject, with enlarged cutaway views respectively illustrating a glottis of the human in a relatively open configuration during inhalation and in a relatively closed configuration during exhalation during normal tidal breathing.

Upper airway dehydration further alters the dynamics of the glottis, the triangular-shaped narrow passage within the larynx bounded by the vocal folds (FIG. 2A). Responsible for sound generation, vocal folds are multi-layer tissues coated by mucus and epithelial cell layers that vibrate at around 100 Hz when exposed to pressures that exceed a threshold phonation pressure and to a degree shaped by viscoelastic properties that are highly water-dependent. The glottis aperture fluctuates at around 1 Hz during normal tidal breathing, expanding on inhalation and contracting on exhalation by one to three fold. Dehydration of the glottis reduces flexibility of the vocal folds, and can reduce glottal aperture and air flow as a consequence of reduced glottal pressure associated with diminished turbulent two-phase (droplet in air) mixing. This can promote cough especially in those with laryngeal hypersensitivity.

A measure of glottal dehydration is PTP, which has been shown to decrease with laryngeal hydration. PTP being inversely related to air flow (at a given glottal pressure), it has therefore been found to correlate with propensity to cough, in those with laryngeal hypersensitivity, and to correlate with voice quality in singers and speakers, and to correlate.

Figure 1C:
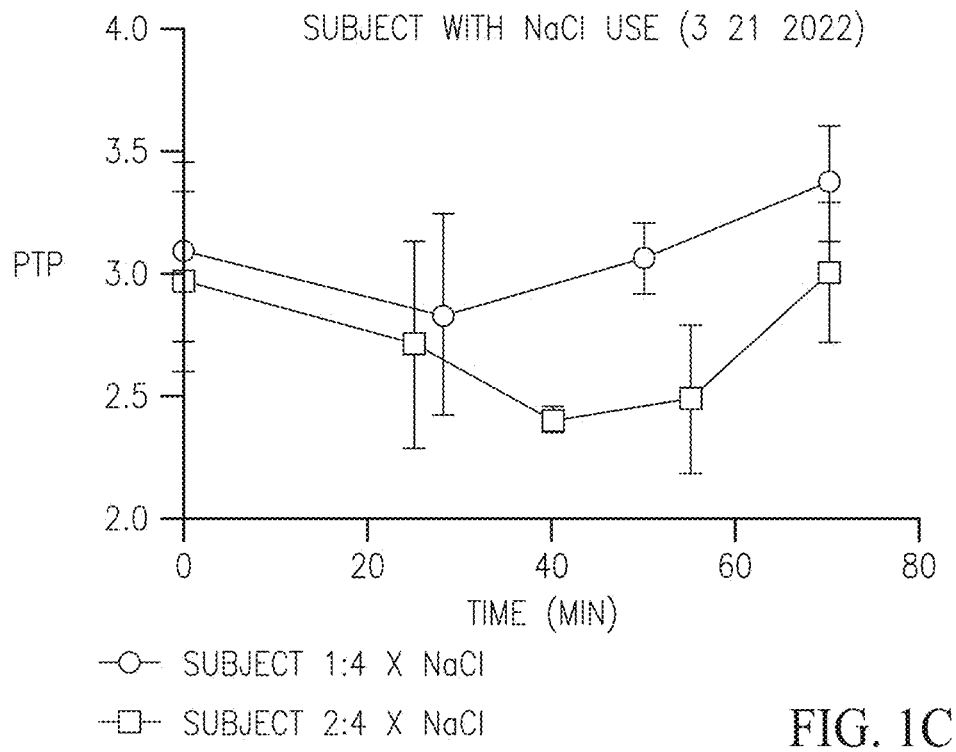
FIG. 1C is a graph showing measurements of phonation threshold pressure (PTP) for two subjects before and after administration of a pump spray of 5% sodium chloride in water to the subjects as droplets with diameter 8 microns to 12 microns, taken at several times, and under conditions as explained with reference to Example 2.
Figure 1D:
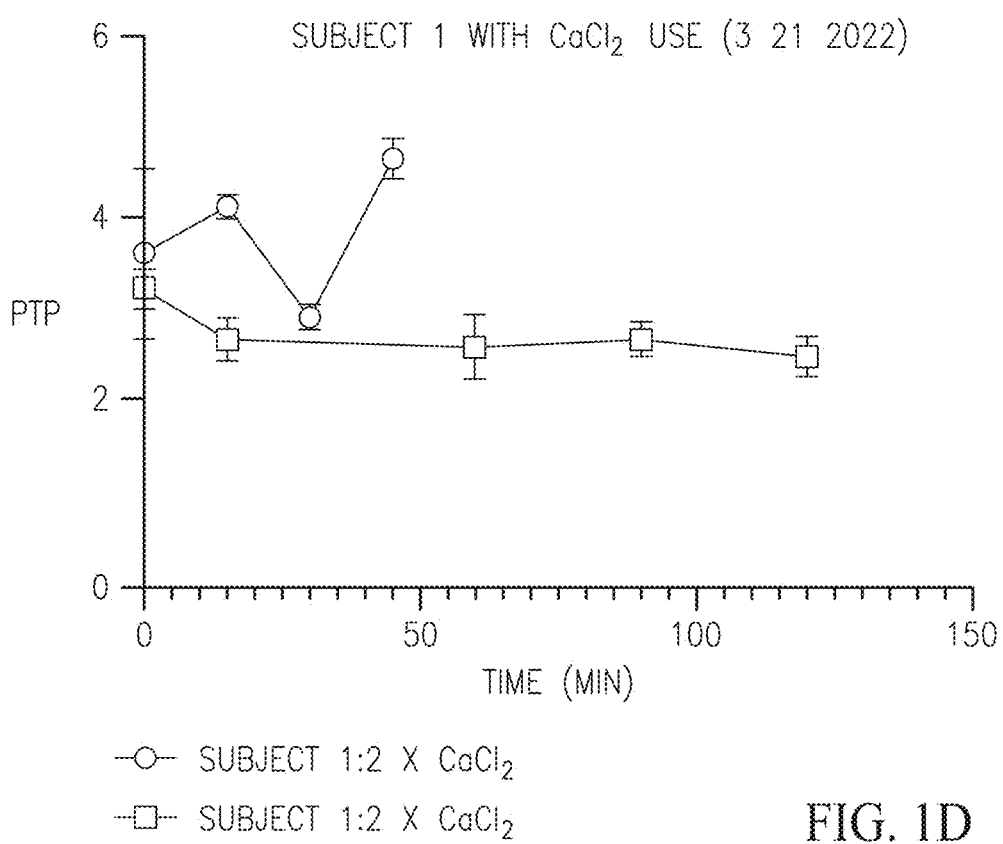
FIG. 1D is a graph showing measurements of phonation threshold pressure (PTP) for a first subject before and after administration of a pump spray of 5% calcium chloride in water to the subjects as droplets with diameter 8 microns to 12 microns over two courses of administration, the second course with twice the salt delivery than the first course, the measurements taken at several times, and under conditions as explained with reference to Example 3.
Figure 1E:
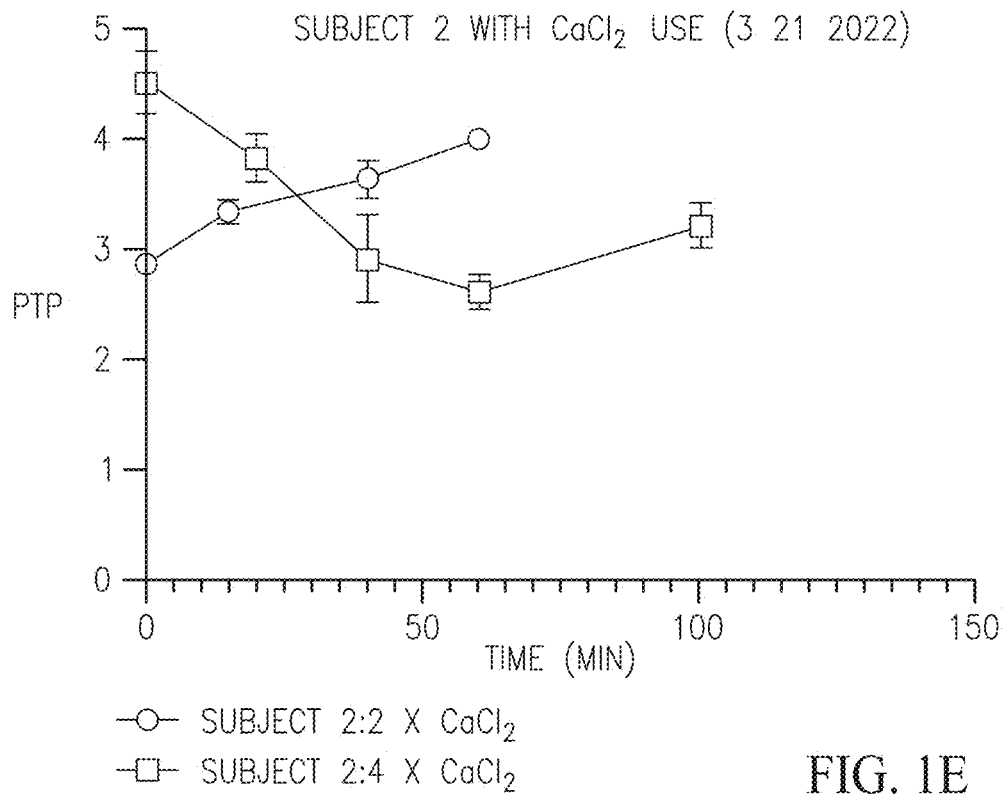
FIG. 1E is a graph showing measurements of phonation threshold pressure (PTP) for a second subject before and after administration of a pump spray of 5% calcium chloride in water to the subjects as droplets with diameter 8 microns to 12 microns over two courses of administration, the second course with twice the salt delivery than the first course, the measurements taken at several times, and under conditions as explained with reference to Example 3.

Inventors hypothesized that in the many conditions in which the glottis dehydrates, promoting risks of lower air flow (oxygen saturation), lowered quality of voice, and possibly cough, depositing hydrating salts in the glottis and trachea would increase surface hydration of the glottis and trachea, and this would improve quality of voice, air flow, and reduce cough incidence. A measure of the effectiveness of the hygienic administration being PTP, the deposition of salts in the larynx and trachea would lower PTP. Inventors also hypothesized that one or more disorders or diseases (e.g., gastrointestinal esophageal reflux disease; asthma) could be advantageously addressed or treated by increasing the pH of the larynx and/or surrounding tissue, for instance via depositing of hydrating salts with a sufficiently high pH to the targeted tissues.

It has been shown that the drinking of water may lower PTP by less than approximately 10% (see, Verdoni et al. Journal of Speech and Hearing Research, Volume 37, 1001-1007, October 1994) (while other studies have found the drinking of water to have no effect on PTP, see Tanner et al. 2010). The inventors hypothesized that the direct topical delivery of salts onto the larynx and trachea might decrease PTP at least to the degree observed for water drinking while faster and for periods of time that would vary with dose of salt and, at sufficient doses, with type of salt. Notably the inventors hypothesized that calcium and magnesium, given their ability to compete for sodium channels in the airways and therefore slow the movement of sodium ions into cells following osmotic challenge, would prolong the duration of airway hydration in comparison to sodium and/or potassium. It should therefore be possible to prolong the duration of airway hydration in proportion to the among of calcium and/or magnesium chloride delivered. This would argue against the use of sodium or potassium chloride in the formulation. Moreover, magnesium, given its role as a muscle relaxer (see www.researchgate.net/profile/Grigorios-Chatziparasidis/publication/11660132_Magnesium_as_a_Relaxing_Factor_of_Airway_Smooth_Muscles/links/602fe5d94585158939b64533/Magnesium-as-a-Relaxing-Factor-of-Airway-Smooth-Muscles.pdf), might at sufficient doses promote longer PTP lowering following administration than, say sodium, and that both magnesium and calcium, given their roles in stabilizing the desensitized state of P2X3 receptors, known to play a critical role in the triggering of cough, might, in the case of cough, further promote diminution of cough incidence at sufficient doses.

The inventors further hypothesized that, laryngeal hypersensitivity often being associated with acidic airway lining fluid in the larynx and trachea (18% to 28% of the human population have gastroesophageal reflux disease, promoting acidic larynx and laryngeal hypersensitivity, www.ncbi.nlm.nih.gov/pmc/articles/PMC6194652/), notably with pH less than 6, or critically less than 5, and most critically less than 4—the hydrating salt solutions would be most effective with a pH of at least approximately 7. Nasal salt solutions frequently possess pH that is lower than 7, and possibly lower than 6. To reduce triggers of glottal constriction, the inventors designed a preferred pH of their hydrating solutions, buffered by bicarbonate, citrate, phosphate or other buffers, in the range pH 7.0 up to around 10.0, or preferably around 7.5 up to around 9.5, or more preferably around 8.0 up to around 9.0, or even more preferably 8.0 to 8.5 or most preferably around 8.0. It is noted that the approximate pH of airway lining fluid in the distal lung is 7.2, and that airway lining fluid with a pH of 7.5 or above is often characteristic of disease.

Example 1 Overnight Dehydration Effect Relative to Natural Daily Hydration

The inventors sought to determine the degree and duration to which PTP might increase owing to the dehydration that accompanies a night's sleep followed by a morning without drinking or eating. Baseline PTP was measured over the first 15 to 30 minutes one morning for subject 1 when the subject did not drink or eat between the time of awakening and the end of the experiment, and on another morning for the same subject when the subject ate, drank and had a coffee. There was a trend to increase over the short experiment when the subject did not drink and to decrease when the subject did drink. On another morning this subject and another did not eat or drink after awakening (following a night of no food or drink) and only receiving at the start of the experiment 2 breaths of the NaCl airway hydration (2 breaths of NaCl being insufficient to produce reduction in PTP, see Example 2). In both cases PTP was measured for at least 45 minutes. See FIG. 1A.

In these, and all of the experiments performed in the following examples, PTP was assessed with the participant pronouncing the sound "pa" repeatedly during a single expiration. Using the AeroView software, three PTP values were obtained by identifying the 3 lowest threshold pressure peaks and determining the PTP from these. This was repeated twice to obtain three average PTP values. The PTP value corresponding to each of the participants at each of a number of moments in time was determined by an average of the three PTP values for each respective moment in time and reported as the average+/−standard deviation.

The average PTP of each subject on the dehydration morning increased over time very significantly. The subjects were in a dehydrated state that grew rapidly progressively worse.

We then measured the next morning PTP after a 10-hour period during which the two subjects neither ate nor drank liquids (overnight) and while measuring PTP values after they ate breakfast and drank an 8 ounce glass of water immediately after the first PTP measurement. The results shown in FIG. 1B reveal that their PTP remained relatively constant.

Example 2 NaCl Laryngeal Hydrating Salts

Inventors sought to determine the degree and duration to which PTP might be lowered in a human subject by NaCl laryngeal hydration. The subjects neither ate nor drank for 1 hour prior to the measurements. A pump spray of 5% sodium chloride in water was prepared, the pump spray designed to deliver droplets with diameter 8 microns to 13 microns. PTP was first measured using the Aeroview System to determine a baseline PTP value as described in Example 1. The subject then activated the pump spray for 4 seconds and inhaled deeply through the nose over these 4 seconds with the mist approximately 2 inches from the nose. This was done four times (leading to an estimated 1.0 mg to 1.6 mg delivered salt dose and approximately 0.2 mg to 0.4 mg deposited salt dose in the larynx and surrounding tissues). PTP was measured 15 minutes post administration, measured again at 30 minutes, then measured at 60 minutes and measured at 2 hours after administration using the Aeroview System. The results are shown in FIG. 1C for the 2 subjects. PTP diminished well over 10% for one individual and less than 10% for the second individual and returned to baseline within approximately one hour after administration.

Example 3 $CaCl_2$ Laryngeal Hydrating Salts

Inventors sought to determine the degree and duration to which PTP might be lowered in a human subject by $CaCl_2$ laryngeal hydration following a full night of fasting (10 h)

and over a two-hour period during which the subject neither ate nor drank liquids. A pump spray of 5% calcium chloride in water was prepared, the pump spray designed to deliver droplets with diameter 8 microns to 13 microns. PTP was first measured using the Aeroview System to determine a baseline PTP value as described in Example 1. The subject then activated the pump spray for 4 seconds and inhaled deeply through the nose over these 4 seconds with the mist approximately 2 inches from the nose. This was done twice during a first course of administration (leading to an estimated 0.5 mg delivered salt dose and approximately 0.15 mg deposited salt dose in the larynx and surrounding tissues, denominated as a "low dose") and done four times during a second course of administration (leading to an estimated 1.0 mg delivered salt dose and approximately 0.3 mg deposited salt dose in the larynx and surrounding tissues, denominated as a "high dose"). PTP was measured 15 minutes post administration, measured again at 30 minutes, then measured at 60 minutes and measured at 2 hours after administration. The results are shown in FIGS. 1D and 1E for 2 subjects, respectively, for each of a "low dose" and a "high dose." PTP increased, reflecting dehydration circumstances and the lack of effect of the topical hydration. The experiment was repeated with the subjects administering the hypertonic sodium chloride nasally four times (leading to an estimated 1.0 mg to 1.6 mg delivered salt dose and approximately 0.2 mg to 0.4 mg deposited salt dose in the larynx and surrounding tissues). PTP was measured 15 minutes post administration, measured again at 30 minutes, then measured at 60 minutes and measured at 2 hours post after administration using the Aeroview System. The results are shown in 1.4A and 1.4B for the 2 subjects, and for each of a "low dose" and a "high dose" for each subject. PTP diminished by approximately 15% (subject 1) to approximately 40% (subject 2) and remained significantly below baseline even at 2 hours post administration. The longer duration of suppression by $CaCl_2$ (FIGS. 1D and 1E) relative to NaCl (FIG. 1C) at the same dose of salt reflects the diminution of ion flux into epithelial cells post osmotic shrinkage owing to the divalent cation (Ca++) interaction with the epithelial sodium (Na) channels.

Example 4 $MgCl_2$ Laryngeal Hydrating Salts

Figure 1F:
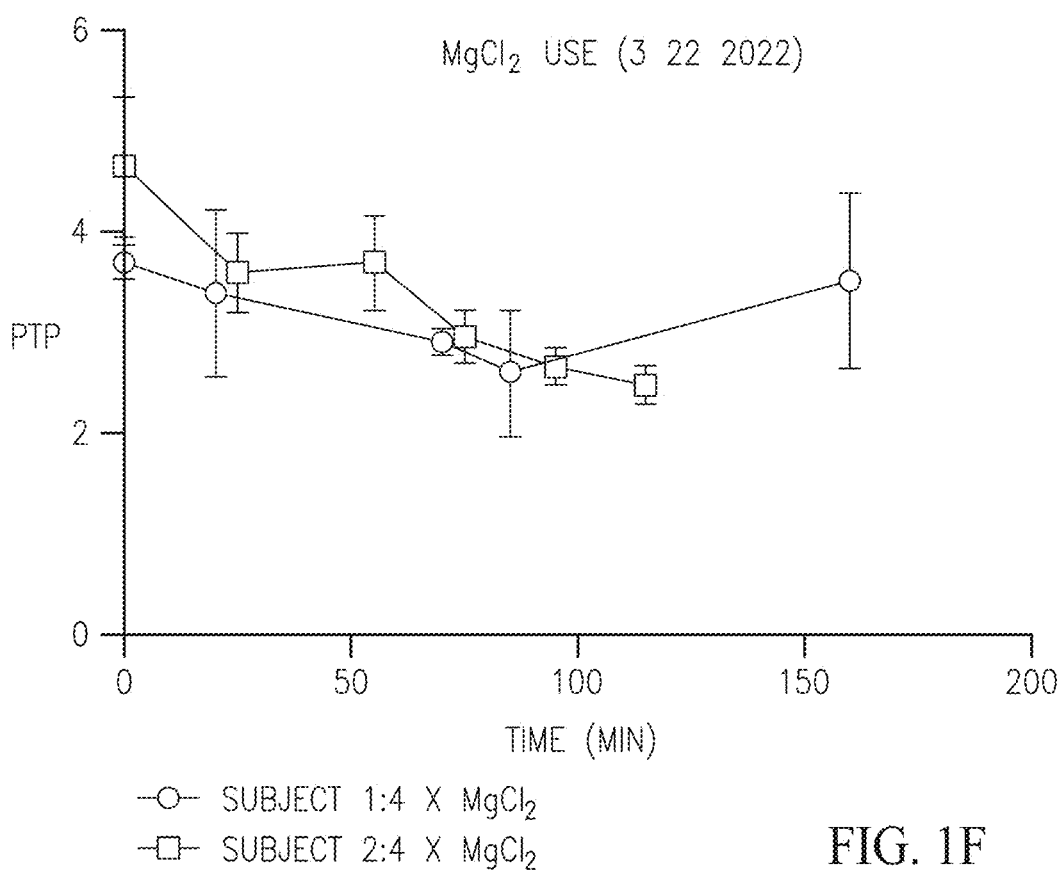
FIG. 1F is a graph showing measurements of phonation threshold pressure (PTP) for two subjects before and after administration of a pump spray of 5% magnesium chloride in water to the subjects as droplets with diameter 8 microns to 12 microns, taken at several times, and under conditions as explained with reference to Example 4.

Inventors sought to determine the degree and duration to which PTP might be lowered in a human subject by $MgCl_2$ laryngeal hydration following a full night of fasting (10 h) and over a two-hour period during which the subject neither ate nor drank liquids. A pump spray of 5% magnesium chloride in water was prepared, the pump spray designed to deliver droplets with diameter 8 microns to 13 microns. PTP was initially measured using the Aeroview System to determine a baseline PTP value as described in Example 1. The subject then activated the pump spray for 4 seconds and inhaled deeply through the nose over these 4 seconds with the mist approximately 2 inches from the nose. This was done four times (leading to an estimated 1.0 mg delivered salt dose and approximately 0.2 mg to 0.4 mg deposited salt dose in the larynx and surrounding tissues). PTP was measured 15 minutes post administration, measured again at 30 minutes, then measured at 60 minutes and measured at 2 hours after administration using the Aeroview System. The results are shown in FIG. 1F for the 2 subjects. PTP diminished by approximately 15% to 30% and returned to baseline in around three hours for one individual and remained low for the other individual after 2 hours post administration. The longer duration of suppression by $MgCl_2$ relative to NaCl (FIG. 1C) at the same dose of salt, similar to the suppression observed with Ca++ (FIGS. 1D, 1E), again reflects the diminution of ion flux into epithelial cells post osmotic shrinkage owing to the divalent cation (Mg++) interaction with the epithelial sodium (Na) channels.

Example 5 Buffered $CaCl_2$ Laryngeal Hydrating Salts

Given the optimal effectiveness of the divalent salts at producing a prolonged hydration of the larynx (as reflected in the lowered PUP values), inventors chose one of the two, notably calcium chloride, to optimize the pH. The pH of the 5% $CaCl_2$ solution was measured and observed to be pH=6.4. To produce a neutral or slightly basic solution optimal for the conditions of the larynx and trachea, a 5% $CaCl_2$ solution was prepared and titrated via a bicarbonate buffer to obtain a 5% $CaCl_2$ solution with pH 7. Over two days the pH remained constant at approximately 7-7.1.

Example 6 Laryngeal Dehydration by Exercise

Figure 1G:
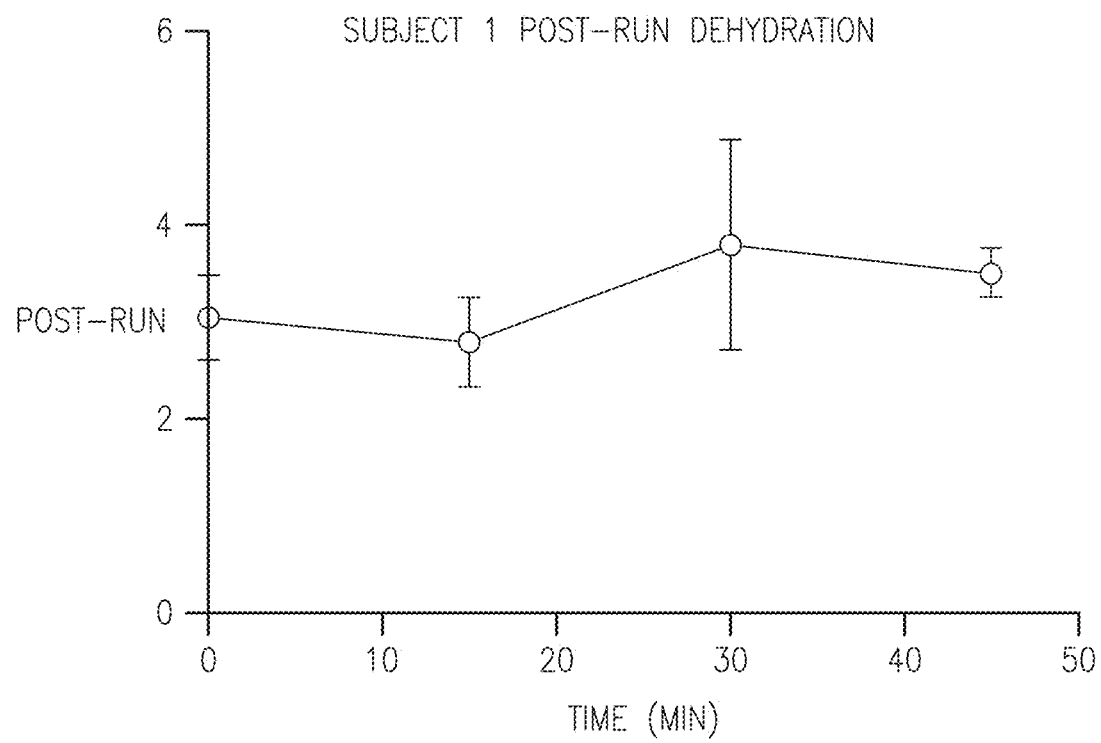
FIG. 1G is a graph showing baseline measurements of phonation threshold pressure (PTP) for a subject, taken at before and at several times after running for an hour, as explained with reference to Example 6.

Inventors sought to determine the degree and duration to which PTP might be increased in a human subject by strenuous exercise and perspiration. PTP was initially measured using the Aeroview System to determine a baseline PTP value as described in Example 1. The subject then ran for one hour. PTP was measured 15 minutes post the run, and measured again at 30 minutes, and at 45 minutes after administration using the Aeroview System. The results are shown in FIG. 1G for the subject. PTP was increased significantly over the 45 minutes by approximately 20%.

Example 7 Cough Management with Laryngeal Hydrating Salts

Figure 1H:
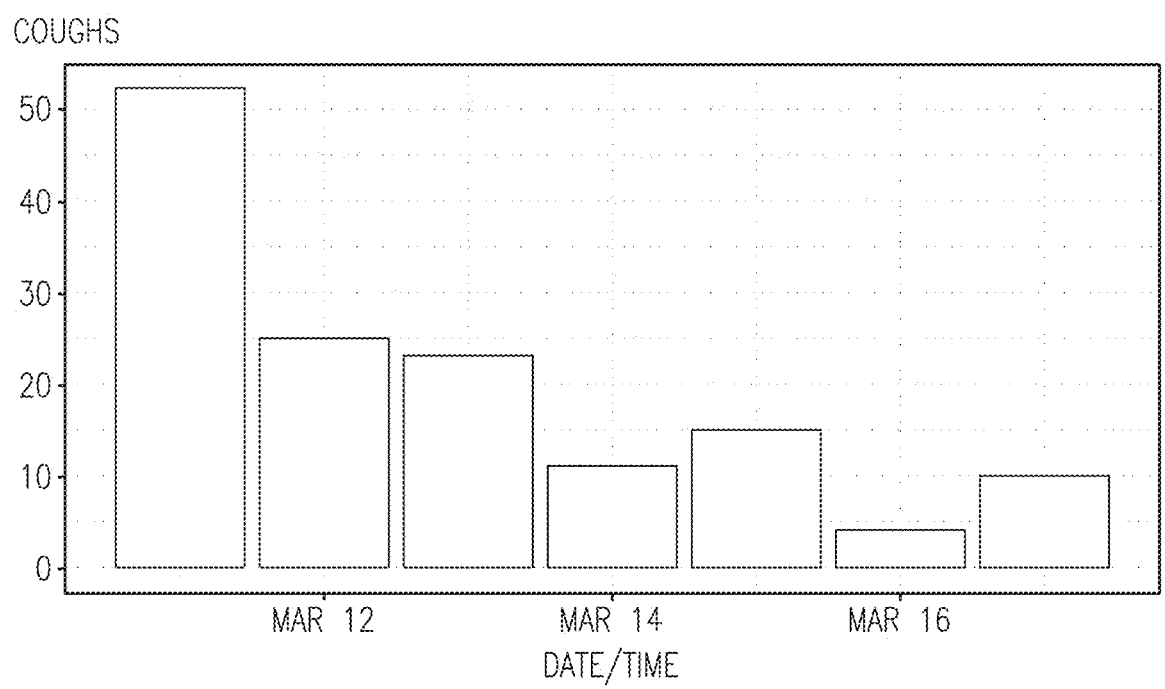
FIG. 1H is a graph showing cough frequency for a subject measured over seven days and at several times over each day, for three days prior to administration, and for four days during administration of a pump spray of 5% calcium chloride and 0.1% sodium chloride in water to the subject as droplets with diameter 8 microns to 12 microns, under the conditions explained with reference to Example 7.

Inventors sought to determine the degree to which chronic refractory cough might be diminished by delivery of laryngeal hydrating salts, and specifically by the calcium chloride compositions. A pump spray of 4.99% calcium chloride and 0.1% NaCl in water was prepared. A baseline chronic cough frequency (coughs per hour and coughs per day) of the subject for 3 days was measured using a digital AI technology (HYFE) that operated with an Android phone. The subject wore the phone around the neck or kept the phone nearby his or her person. The phone and application remained on generally for 24 h per day while occasionally for lesser periods during which the subject was prone to coughing. After the baseline period, on day 4 (March 14), the subject began to administer the laryngeal hydrating salts every 4 hours from first waking until the end of the day. The subject continued for four days. Each administration involved two nasal inhalations (leading to an estimated 0.5 mg to 0.8 mg delivered salt dose and approximately 0.1 mg to 0.2 mg deposited salt dose in the larynx and surrounding tissues). Cough frequency for the subject was monitored as shown in FIG. 1H. Cough frequency (per day) over the four days of airway hydration administration diminished (average 9) by around 70% relative to the three days of non-treatment (average 33) with a variance of 32% diminution on the highest cough frequency day (treatment) relative to the lowest cough frequency day (non-treatment) to 91% on the lowest cough frequency day (treatment) relative to the highest cough frequency day (non-treatment).

Example 8 Sports Application

Inventors sought to explore whether the laryngeal hydration described in the previous examples, and specifically as described in Example 3, might alter oxygen saturation as well.

Figure 3A:
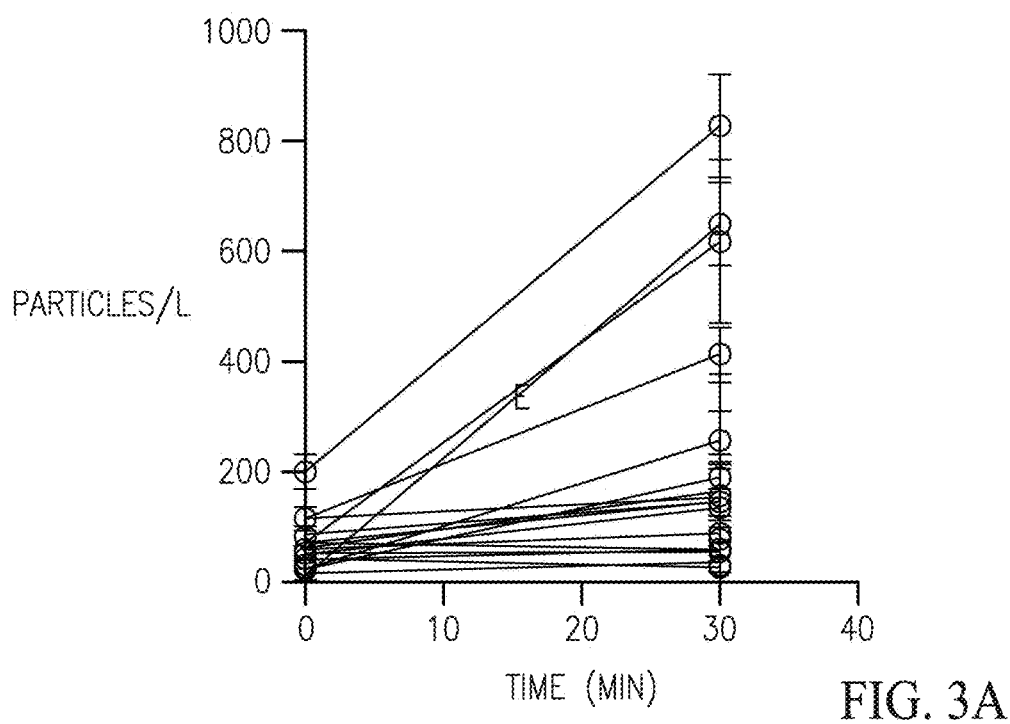
FIG. 3A is a graph showing exhaled aerosol particles from a number of healthy human subjects in an exercise-induced dehydration study for all subjects before and after 30 minutes of exercise.
Figure 3B:
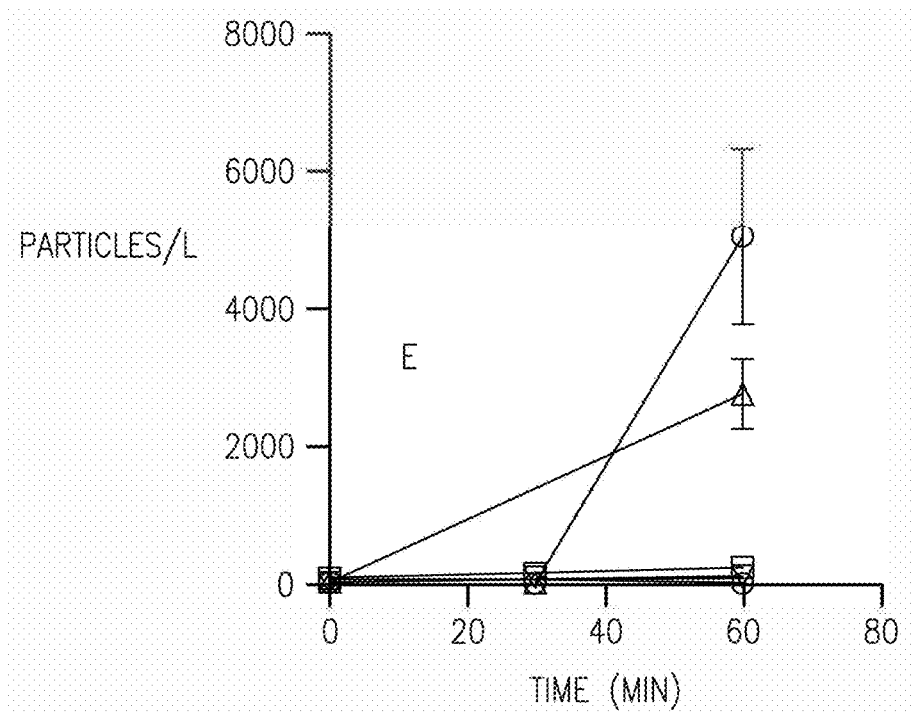
FIG. 3B is a graph showing exhaled aerosol particles from the number of healthy human subjects in the exercise-induced dehydration study for all non-treatment "control" subjects before, during and after 60 minutes of exercise.
Figure 3C:
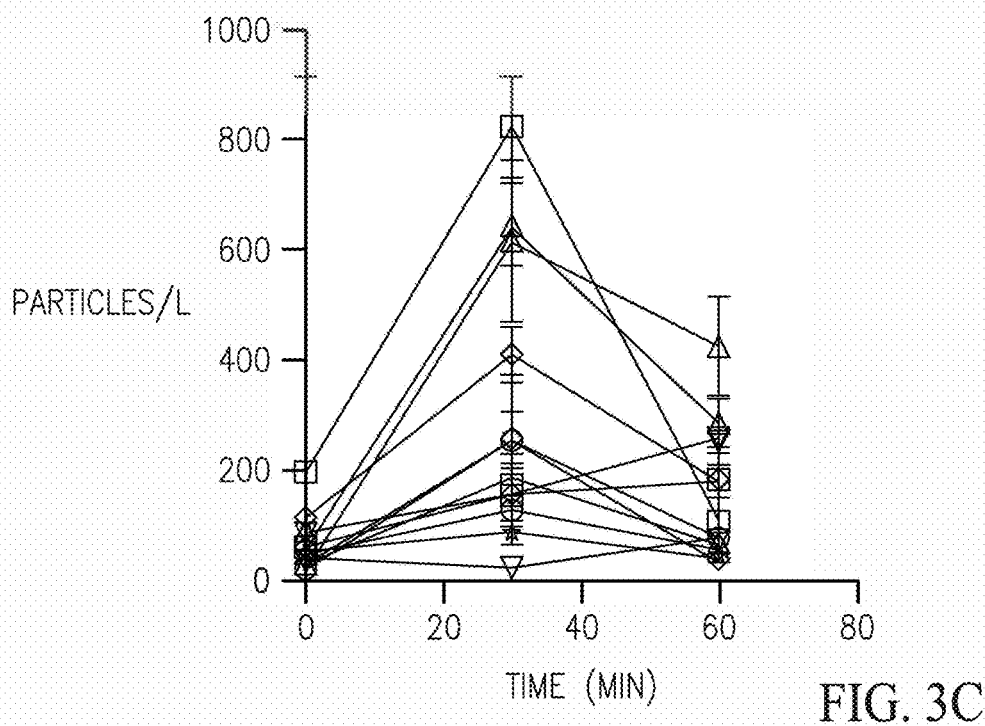
FIG. 3C is a graph showing exhaled aerosol particles from the number of healthy human subjects in the exercise-induced dehydration study for all treatment subjects before and after administration of a hydrating aerosol of droplets comprising a salt-based formulation or composition to the upper airway, the hydrating aerosol administered at 30 minutes of exercise.
Figure 3D:
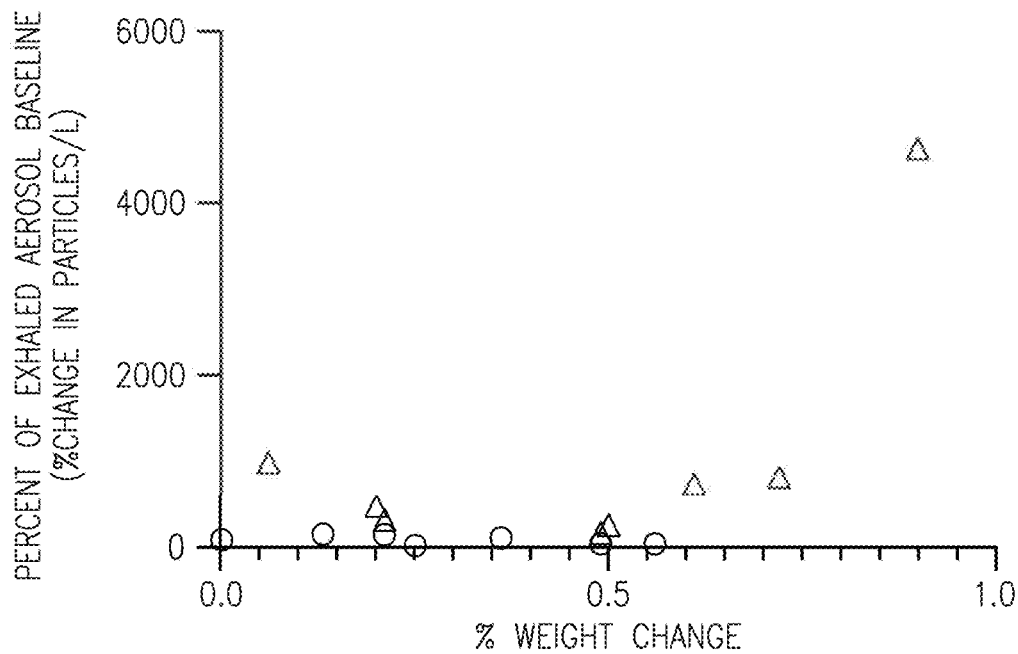
FIG. 3D is a graph showing an effect of dehydration weight loss on exhaled aerosol particles over the course of the exercise-induced dehydration for the subjects after 30 minutes of exercise.

A randomized observational two-armed study of exercise-induced dehydration was conducted using 20 young (22-45 years of age), low-BMI (21-28) human volunteers in Boston, Massachusetts. Healthy volunteers (17 males, 3 females, no smokers) participated in a coordinated workout that involved weight training and other physical exercises over 60 minutes within an air-conditioned gymnasium at 20-25 C and 50-70% relative humidity with all exhaled aerosol measurements performed once subjects had recovered normal tidal breathing. Water loss among the participants ranged from 0.1% to 0.9% of total body mass over the course of the 60 minutes. At 30 minutes into the workout half of the subjects were randomly selected to receive by nasal inhalation a hydrating composition, notably a calcium-rich hypertonic salt solution (4.99% calcium chloride and 0.01% sodium chloride by weight) with droplet size 8 µm to 12 µm targeting the nose, trachea, and main bronchi. Each administration involved two nasal inhalations (leading to an estimated 0.5 mg to 0.8 mg delivered salt dose and approximately 0.1-0.2 mg deposited salt dose in the larynx and surrounding tissues). Exhaled aerosol numbers increased significantly for all subjects (P=0.002) following 30 minutes of exercise from mean values of 58.8+/−17.1 particles per liter of air (n=21) to 220.6+/−97.5 particles per liter of air (n=19) (FIG. 3A). For the control group mean exhaled aerosol post 60 minutes of exercise (855+/−995 particles per liter of air) (FIG. 3B) did not significantly change (P=0.204). For the active group at 60 minutes (30 minutes post administration of the calcium-rich hypertonic salts) exhaled aerosol significantly diminished (P=0.045) with mean exhaled aerosol of 151.9+/−113.2 particles per liter of air (FIG. 3C) Exhaled aerosol generally increased with weight loss for all subjects prior to salt administration (FIG. 3D). Those above the median weight loss of 0.24% exhaled 688.3%+/−448.9% more aerosol relative to baseline, and those below the median 0.24% weight loss exhaled 225.4%+/−97.7% relative to baseline, while these differences were without significance (P=0.33).

Pulse oxygen saturation pressure was evaluated in a subset of the human volunteer subjects. Mean oxygen saturation fell significantly (P<0.05) for all subjects (n=6) from 98.7%+/−0.9% prior to exercise to 96.7%+/−0.5% at 30 minutes of exercise. Mean oxygen saturation for the control group (n=3) reached 96.5%+/−0.8% at 60 minutes post the commencement of exercise, an insignificant change relative to levels at 30 minutes while significantly below the pre-exercise levels (P=0.01). For those subjects (n=3) who received the laryngeal-targeted calcium-rich salts at 30 minutes post exercise, oxygen saturation rose significantly (P<0.05) for two of the three subjects and remained unchanged (P>0.05) for the third; mean oxygen saturation for the group was 97.1%+/−0.5% at 60 minutes post the commencement of exercise. These trends are similar to those reported elsewhere in an exercise-induced dehydration study following systemic hydration.

Administration of laryngeal hydration by hydrating salts can, for example, increase oxygen saturation by approximately 1%, 2%, 3%, 4%, 5%, 6%, 7%, 8%, 9%, 10% or even more depending on the degree of dehydration of the glottis, which can vary based on the dryness of the air and the overall loss of water from or dehydration of the individual.

Example 9 Disease Application

Inventors sought to explore whether the laryngeal hydration described in the previous examples might alter oxygen saturation in states of lung infection (i.e., where dehydration often occurs).

The effect of daily administration of calcium-rich hypertonic salts to the upper airways on exhaled aerosol, oxygen saturation, and disease symptoms was evaluated in a randomized double-blinded nasal-saline control study of 40 moderately symptomatic COVID-19 patients admitted into Bangalore Baptist Hospital during the period May-June when the delta variant predominated infections in India. Most of the COVID-19-positive subjects in the two arms of the study entered the hospital with fever, cough, body pain and loss of smell or taste sensation (Table of FIGS. 1K, 1L, 1M, 1N, 1O, 1P, 1Q, 1R, 1S), and mean initial self-reported symptom scores of 3.15+/−0.17 (no statistical difference in symptom scores was observed between the two groups, P=0.599). Three of the subjects in the active group were escalated to intensive care prior to completing the three days of treatment and were therefore excluded from the post-treatment results. See Table of FIGS. 1K, 1L, 1M, 1N, 1O, 1P, 1Q, 1R, 1S.

Administration of the active reduced exhaled aerosol in all subjects (FIG. 4A) 30 minutes post administration, and for all but one subject for the duration of the assessment (up to 2 hours post administration). Administration of the SIMPLY SALINE™ (i.e., purified water, sodium chloride, and sodium bicarbonate) control did not change overall exhaled aerosol for the group (P=0.122), while several of the subjects did exhale fewer respiratory droplets post administration of the nasal saline control.

This diminution of exhaled aerosol following the nasal saline control reflects that patients in the study adopted prone positions in the hospital. On delivery of salt solution to the nose, and not to the larynx and trachea, inclining the neck, or placing the head in a relatively horizontal (prone) position, can deliver a solution applied initially to the nose, into the larynx by post-nasal drip, an alternative means of delivering the laryngeal hydrating salt compositions.

Figure 4A:
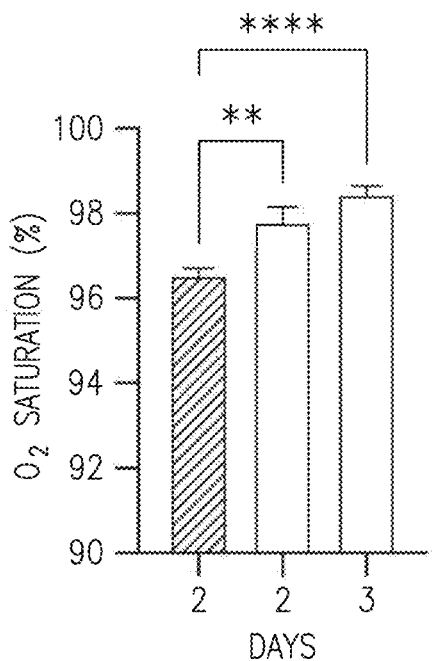
FIG. 4A is a graph showing oxygen saturation levels as a function of days after administration of an aerosol of droplets comprising a salt-based formulation or composition (FEND) for 17 subjects.
Figure 4B:
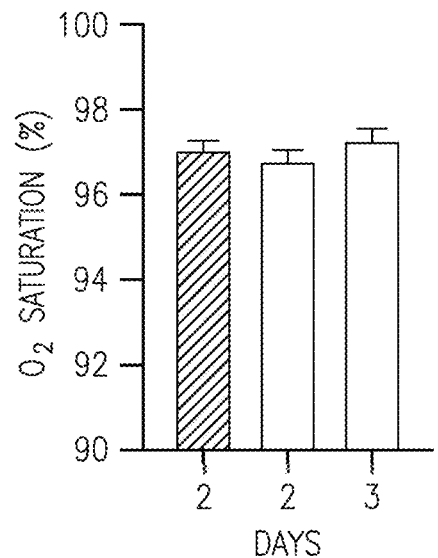
FIG. 4B is a graph showing oxygen saturation levels as a function of days after administration of an aerosol of droplets comprising a salt-based formulation or composition (sodium chloride) for 20 subjects.

Among the subjects of each group who entered the trial with elevated CRP levels (CRP>10 mg/mL), intravenous antibiotics or steroids were needed in only 25% of the active group (n=8) versus 63.64% of the saline control group (n=11) (FIG. 4B). CRP levels fell from day 1 to day 3 in 75% of the active group and in 52.6% of the control group (FIGS. 1K, 1L, 1M, 1N, 1O, 1P, 1Q, 1R, 1S).

Oxygen saturation levels began at similar levels for the active and control groups at the start of the study. Over the course of the three days of administration, oxygen saturation rose significantly (P=5.981e-07) in the active group and did not change (P=0.533) in the SIMPLY SALINE™ control group. These results are similar to the results reported in Example 6, in the circumstances of exercise-induced dehydration, and suggest that drying out of the glottis in a respiratory disease such as COVID-19, can lead to a fall in oxygen saturation, which can be reversed by proper laryngeal hydration with hydrating salts.

It would also be possible to treat one or more disorders or diseases (e.g., gastrointestinal esophageal reflux disease; asthma) via administration of a salt-based composition with a pH selected to neutralize or approximately neutralize a pH of the larynx and/or tissue surrounding or otherwise proximate the larynx.

A non-buffered NaCl based saline may typically have a pH of around 6.5. In contrast, a healthy larynx and/or trachea is typically associated with a saline having a pH of around 7.0. A saline associated with an acidic larynx typically has a pH of around 4 to around 6.5. In at least some implementations, the compositions or treatments herein advantageously employ a saline of magnesium chloride ($MgCl_2$) and/or calcium chloride ($CaCl_2$) that may be buffered having a pH of around 8 to around 10. Additionally or alternatively, in at least some implementations, the compositions or treatments herein can advantageously be non-aerated, for example comprising or employing an inert gas (e.g., nitrogen) instead of air or at least partially displacing air, the inert gas advantageously inhibiting or even preventing carbon dioxide ($CO_2$) contact which might otherwise lower the pH of the composition from a desired pH of around 8 to around 10. Thus, there are at least two ways of maintaining a basic pH of a solution with the described salts. One approach employs a buffer for the Mg and/or Ca/Mg solutions. Another approach uses the natural pH of $CaCl_2$ and $MgCl_2$ (pH around 9-10 when formed), and prevents $CO_2$ contact with the composition by filling in nitrogen, for instance to prevent or at least inhibit the formation of carbonic acid. Administration can also involve preventing or at least inhibiting the entry or ingress of $CO_2$ during use. In the latter case, while there may be some acidity that results from reaction with $CO_2$ on administration (e.g., spraying) into the airways, the composition maintains a basic pH.

For a nose, the amount of airway lining fluid is estimated to be about 160 mg, and for a combination of a larynx and trachea the amount of airway lining fluid is estimated to be about 60 mg. A mass of salt solution per inhalation that deposits in the nose is estimated to be approximately 10 mg, and that deposited to the larynx and trachea is estimated to be approximately 3 mg per inhalation. As such, it estimated that it would take about 4 breaths to raise a pH of the larynx and trachea, and optionally the nose, to between about 6 and 7 employing a composition with a nominal pH of about 9.

Various compositions can be compared to one another based on compositional variables. A first FEND composition comprises NaCl and $CaCL_2$, and has a pH of around 6 to 6.5. The first FEND composition includes both monovalent and divalent salts, and is acidic. A second FEND composition comprises $CaCl_2$ and $MgCl_2$, and has a pH of around 7 to 8. The second FEND composition advantageously employs only divalent salt as compared to the first FEND composition and has a relatively higher pH than the first FEND composition. A third FEND composition of comprises $MgCl_2$ buffered with bicarbonate, and has a pH of around 8 to 9. The third FEND composition advantageously employs only divalent salt as compared to the first FEND composition and has a relatively higher pH than the second FEND composition. The third FEND composition is expected to have the highest efficacy of these three exemplary FEND compositions.

Example 10 Aging and High BMI

Inventors sought to determine the degree to which aging or high BMI increases upper airway dehydration, and whether, therefore, in advanced age or high BMI states, delivery of laryngeal hydrating salts might bring benefits, ranging from increased oxygen saturation to reduced cough frequency, improved voice quality and reduced risks of respiratory illness.

Figure 1J:
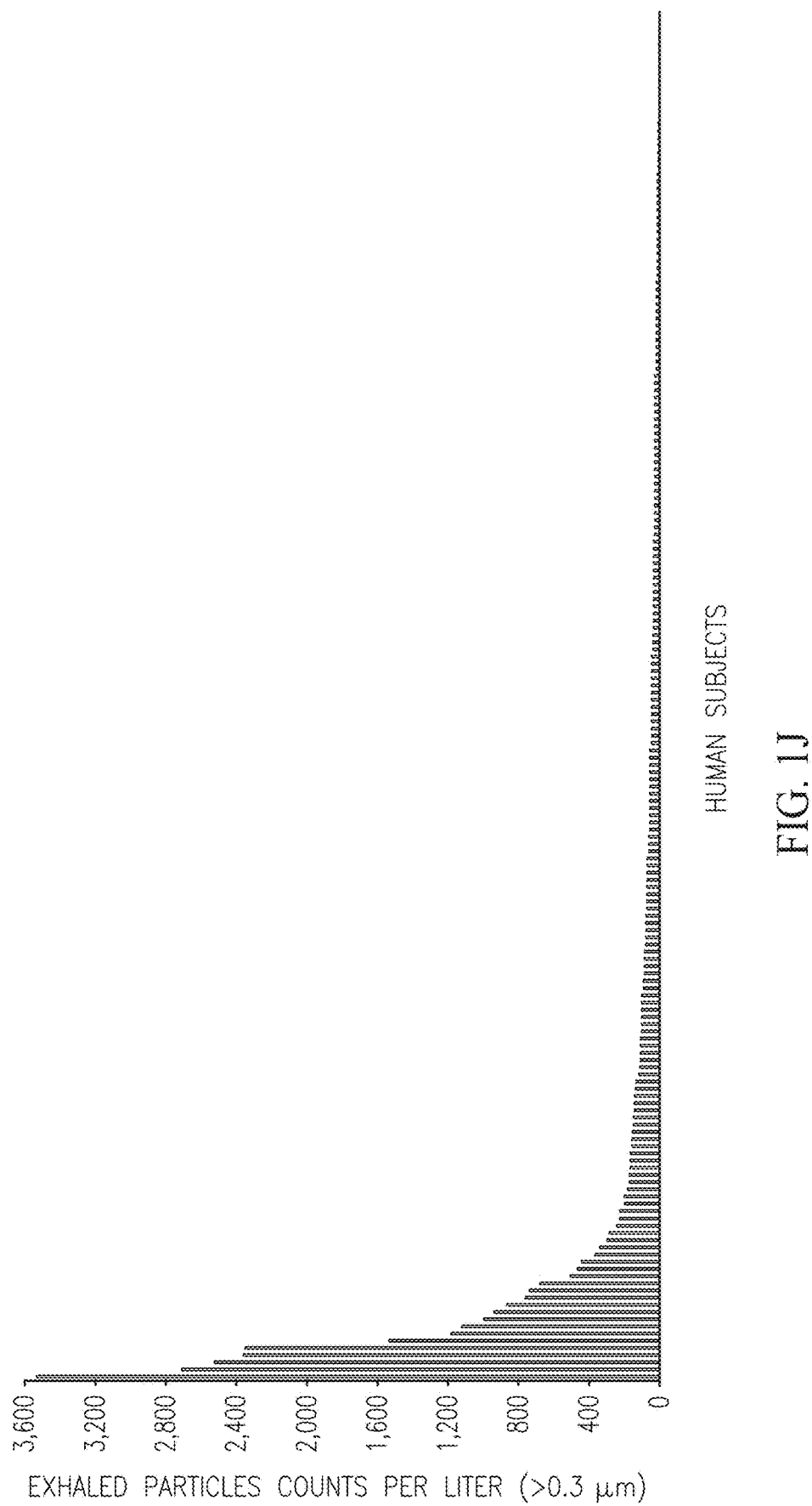
FIG. 1J is a graph showing measurements of exhaled breath particles for 74 essential workers at a food processing facility and of 120 volunteers at Grand Rapids Community College.

The exhaled aerosol of 194 human volunteers at two sites in North Carolina (74 subjects) and Michigan (120 subjects) was evaluated. Observational cohort studies were conducted of essential workers in Asheville, North Carolina, and of students, staff and faculty at Grand Rapids Junior College in Grand Rapids, Michigan over a total period of four days. The results from these measurements are shown in FIG. 1J. Data represents particle counts per liter of exhaled air (particle diameter larger than 300 nm) for each of the 194 individuals. Error bars represent standard deviation sample calculations based on three to 12 exhaled aerosol count measurements with each measurement an average of counts over a five second time interval.

Exhaled aerosol particle numbers varied three orders of magnitude between subjects, and were remarkably consistent across the two study sites. Subjects were categorized by those exhaling greater or less than 156 particles per liter of air. This demarcation was chosen since the individuals above this threshold aerosol number exhaled 80% of the total particle production from the 194 human volunteers while being less than 20% of the total members of the group—analogous to the conventional definition of super spreading of airborne infectious disease. Within this high producing group, we noted that approximately 80% of the "super spreader" (of aerosol) production was generated by approximately half of the group, i.e., eighteen individuals. Qualified as "low spreaders" were those 159 individuals who exhaled below 156 particles per liter. The individual data for each category are shown with standard deviations (FIGS. 1A, 1B, 1C, 1D, 1E, 1F and 1G). We evaluated relationships between exhaled aerosol particle number and sex, age, and body mass index (BMI). No correlation was found with sex, while significant correlations were observed between exhaled aerosol, age and BMI—and particularly BMI-years. Each of the 146 individuals for whom we obtained age and BMI information were characterized by their age multiplied by their BMI, or by their BMI years. Half of the group (73 individuals) with lowest BMI years (less than 650 BMI years) exhaled significantly less aerosol than the half of the group (73 individuals) with highest BMI years (above 650 BMI years) ($p<0.015$. All volunteers<26 years of age and all subjects under 22 BMI were characterized as low spreaders of exhaled bioaerosol.

Notably, the increase in exhaled aerosol in the older and higher BMI subjects is similar to the increase seen in exercise-dehydrated younger subjects or, as shown in Field et al. (2021), in the airways of those who are breathing very dry air relatively to the breathing of humid air. Whole-body dehydration being understood to correlated with advancing age and increasing BMI, these results are assumed to be indicative of the dehydration of the larynx and trachea with advanced age and increasing BMI.

FIG. 2A shows a portion of a human subject 200, with enlarged cutaway views respectively illustrating a glottis of the human in a relatively open configuration 202a during inhalation and in a relatively closed configuration 202b during exhalation during normal tidal breathing.

Figure 2B:
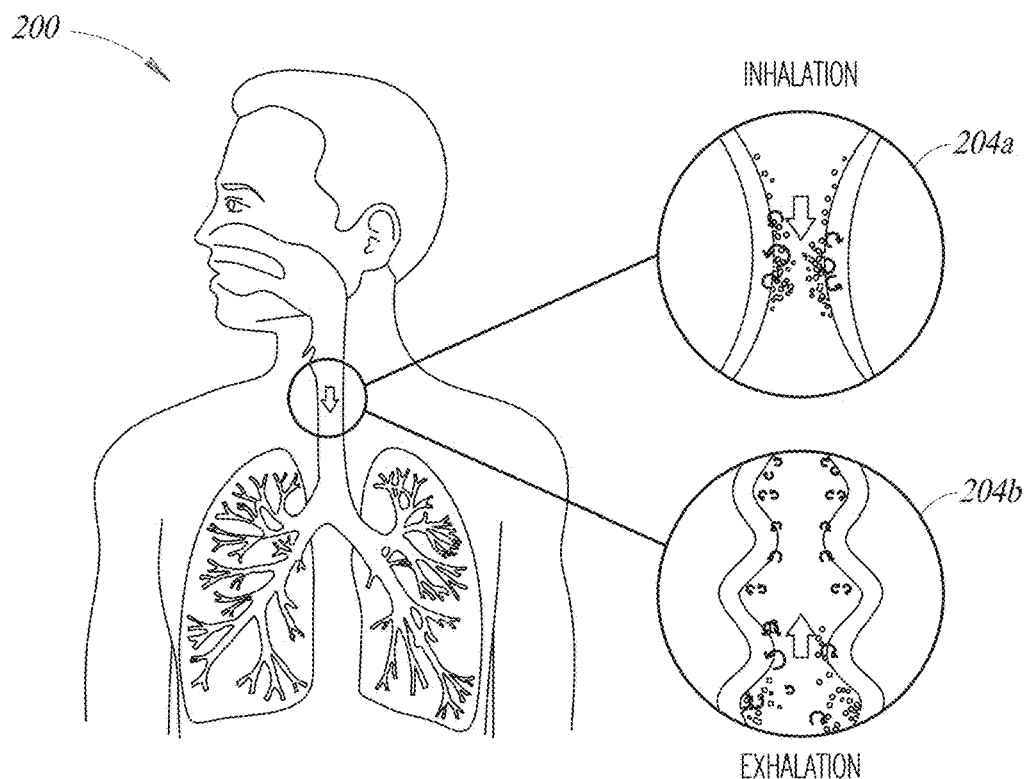
FIG. 2B is an illustration showing the human subject of FIG. 2A, with enlarged views respectively illustrating airflow, droplet generation and turbulent eddies in a larynx of the human subject during inhalation and during phonation.

FIG. 2B shows a portion of the human subject 200 of FIG. 2A, with enlarged views respectively illustrating airflow, droplet generation and turbulent eddies in a larynx 204 of the human subject during inhalation 204a and during phonation 204b.

Figure 2C:
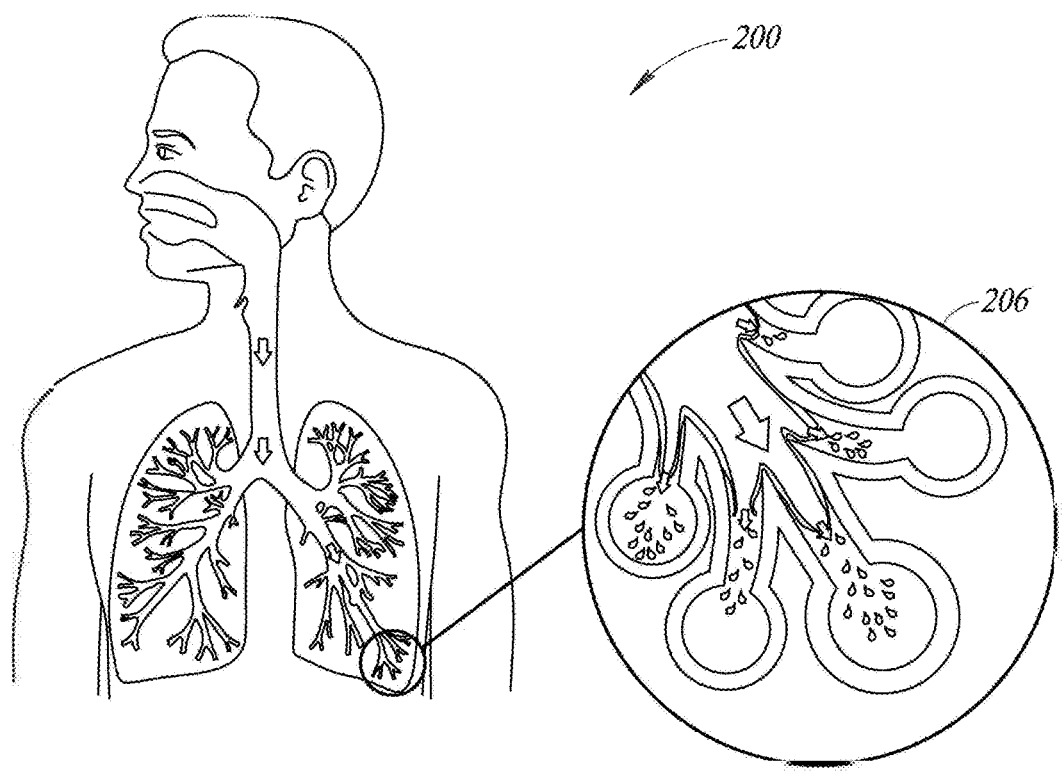
FIG. 2C is an illustration showing a human subject, with an enlarged view illustrating airflow in the lower respiratory tract during inhalation during normal tidal breathing.

FIG. 2C shows a portion of the human subject 200, with an enlarged view illustrating airflow in the lower respiratory tract 206 during inhalation during normal tidal breathing.

FIG. 4A is a graph 400a showing oxygen saturation levels as a function of days after nasal spray administration of an aerosol of droplets comprising a salt-based formulation or composition (hypertonic calcium-rich salt, e.g., 0.43M CaCl, 0.05M NaCl; 4.72% CaCl, 0.31% NaCl) for 17 subjects.

FIG. 4B is a graph 400b showing oxygen saturation levels as a function of days after nasal spray administration of an aerosol of droplets comprising a salt-based formulation or composition (isotonic saline of 0.9% sodium chloride) for 20 subjects.

Experimental results were obtained of various attempts to treat persistent coughing of an individual with an aerosol of droplets with a salt-based formulation or composition and comparing such without treatment (baseline) and with treatment using codeine. While a small data set, such demonstrates the ability to suppress persistent coughing via treatment with a hydrating aerosol of droplets with a median volume size of approximately 8 μm to approximately 12 μm, the droplets comprising a solvent and a salt-based formulation or composition (e.g., calcium-rich) to target a larynx and/or tissue surrounding or otherwise in the vicinity of the larynx.

In particular, an informal study was run on a single subject suffering from a post viral cough exacerbation with about 15 coughs per hour. The presented data is complicated given time changes from PST to EST on December 7$^{th}$ and back to PST on December 12$^{th}$, and some uncertainty about whether the subject correctly administered the hydrating aerosol on December 11$^{th}$.

Experimental intervention points occurred when the subject self-administered a hydrating aerosol of droplets with a median volume size of approximately 8 μm to approximately 13 μm, the droplets comprising a solvent and a salt-based formulation or composition (e.g., calcium-rich) to target a larynx and/or tissue surrounding or otherwise in the vicinity of the larynx.

Administration can, for example, reduce frequency of coughing by approximately 5%, 10%, 20% or even more.

Subjectively, the subject reported feeling better after self-administration of the hydrating aerosol for an hour or so following administration. The subject also reported dramatic relief following self-administration of codeine which relief wore off over about 4 to 5 hours following administration of codeine.

Experimental results were obtained of various attempts to treat persistent coughing of an individual with an aerosol of droplets with a salt-based formulation or composition and comparing such without treatment (baseline) and with treatment using codeine.

As discussed herein, the larynx needs hydration, and opens up less well when dry as opposed to when hydrated. Oxygen saturation can fall when the larynx is dry, as it does in response to exercise, aging, or in experiencing sleep apnea. A dry larynx can with time become a hypersensitive larynx. Seasoned athletes frequently have laryngeal hypersensitivity syndrome (LHS), as do some singers. Chronic cough is more common with a dry larynx. Many experiencing chronic cough (5-10% of the human population) also have LHS.

As also discussed herein, the trachea needs hydration, as a dry trachea fails to clear the particles that are inhaled every day and night. Dehydration leads cilia to cease beating, and airways become inflamed. Dehydration of the trachea can cause respiratory droplets to increase, and carry inhaled particles deep into the lungs and back into the outside environment.

The nose, larynx, and trachea, when dry, create osmotic stresses on epithelial cells that are severe, resulting in mucus production, which results in congestion, and can cause trouble with sleeping, an underlying trigger of sleep apnea.

Epithelial cells respond to increased salt in mucus by pumping out water by osmosis. Sodium and potassium diffuse back in to the cell by ion channels. Calcium and magnesium compete for the ion channels modulating rate of membrane transport.

Topical upper airway hydration can be achieved by targeting calcium and/or magnesium salts to the upper airways with benefits lasting up to six hours following brief nasal inhalation. Compositions comprising divalent salts and moisture can be advantageously delivered to the larynx and trachea via the nose with simple, affordable hygienic, over-the-counter (OTC) products that improve breathing and addresses massive healthcare needs and global markets ranging from airborne disease to chronic cough.

Targeted delivery of proprietary compositions of natural salts and water via an aerosol with approximately 8 micron to approximately 15 micron mass media aerodynamic diameter droplets, approximately 9 microns to approximately 13 microns, approximately 9 microns to approximately 12 microns, approximately 8 microns to approximately 13 microns, or approximately 8 microns to approximately 12 microns, uniquely targets hydration to the nose, larynx, and/or trachea.

Hypertonic salt treatments only provide approximately 30 to approximately 60 minutes of hydration benefit. The compositions described wherein can extend the benefit to several hours, by natural modulation of epithelial sodium channel transport via divalent cations (Ca, Mg).

At least some of the compositions described wherein can advantageously address acid larynx reflux. Most nasal salines are acidic. At least some of the compositions described herein have a pH of 7.0 up to around 10.0, or preferably around 7.5 up to around 9.5, or more preferably around 8 up to around 8.5, or even more preferably around 8 up to around 8.5, or most preferably around 8.0, for optimal laryngeal pH to avoid laryngeal hypersensitivity.

Measures of phonation threshold pressure (PTP) and exhaled aerosol are used to demonstrate effectiveness.

A fine mist approximately 8 micron to approximately 15 micron mass median aerodynamic diameter droplets, approximately 9 microns to approximately 13 microns, approximately 9 microns to approximately 12 microns, approximately 8 microns to approximately 13 microns, or approximately 8 microns to approximately 12 microns, assures optimal coverage of sinus and olfactory bulb, while retaining the composition in the upper airways of the respiratory tract, to optimize air flow, reduce coughing, improving particle clearance and/or reducing respiratory droplets. Such can provide natural stabilizers to remedy the desensitized state of P2X3 receptors.

A mechanism of action (MoA) is hydration, and the composition formulated for site of action and mode of action.

In some implementations, the composition can be formulated and/or employed for cosmetic applications (e.g., hygiene). In some implementations, the composition can be formulated and/or employed for medical applications (e.g., regulated as a medical device, OTC drug or treatment, and/or prescription drug or treatment) for particular indications, e.g., chronic cough, laryngeal reflux in GERD (gastroesophageal reflux disease), dysphonia, sleep apnea, or suppressed oxygen saturation (at high altitudes or in high-endurance exercise). Additionally, de novo or "respiratory therapy" (upper airway saline nebulization) applications are possible.

One or more described compositions comprising water and a salt-based composition or formulation (e.g., FEND) is employed as a simple, new, hydration rite, and is grounded in aerosol physics. As described herein, in some implementations the composition takes the form of an aerosol with a mass median aerodynamic diameter or size of from around 8 microns to around 15 microns, approximately 9 microns to approximately 13 microns, approximately 9 microns to approximately 12 microns, approximately 8 microns to approximately 13 microns, approximately 8 microns to approximately 12 microns, or from around 10 microns to around 11 microns, which can be nasally inhaled an which deposit in the nose, trachea and main bronchi, but not into the deep lung. The FEND composition is the first to effectively deposit high concentrations of divalent cations (Ca, Mg) that promote hydration in this the upper airways. Such can advantageously be produced in a world-class pharmaceutical grade aseptic filling operation, allowing safe production of a preservative-free FEND composition, comprising only natural salts and water. The FEND composition is taken is a daily ritual; recommended regular use comprising two nasal inspirations each of 3 times a day.

Eighty million Americans suffer from allergies, asthma, COPD, sleep apnea and other respiratory conditions. Many people, and in particular, caregivers are focused on shared health and increasingly conscious of the risk of shared air. Respiratory illness is the primary reason for reporting to sports clinic other than injury. Strenuous exercise inflames the airways.

Refractory cough afflicts 5-10% of the human population. 21 million adults in the United States are diagnosed chronic cough. Chronic cough is often provoked by acid larynx (a symptom of GERD, 18-28% of North Americans). Chronic (dry) cough is the primary reason patients see a doctor. Chronic cough can be provoked by dry, polluted air and systemic dehydration resulting, for example, from exercise and old age. Current treatments are ineffective. The most recent approval of a cough drug occurred in 1958. Merck's Gefapixant, a P2X3 antagonist, is near FDA approval. Other P2X3 antagonists (oral delivery), e.g., Bayer are entering Phase III trials. P2X3 antagonists are modestly effective but associated with significant side effects. There appears to be no existing effective treatment options for laryngeal reflux. The laryngeal hydration composition can also include a therapeutic molecule whose therapeutic effect involves the targeting of receptors in the upper airways, such as P2X3, TRPV, or ACE2 receptors.

The delivery of salts as described herein can advantageously be employed to also deliver P2X3 antagonist and/or other cough-receptor drugs or pharmaceuticals to reduce cough reflex. Such can advantageously provide at least three distinct benefits. 1. Such can advantageously reduce the ATP signaling by hydrating the airway, which will likely improve the ability of the receptor antagonist to reduce ATP activation. 2. Calcium and/or magnesium will likely reduce speed of return of the receptor from its desensitized state to its sensitized state post release of the receptor by the antagonist. 3. Delivery of the antagonist via the nose and not the mouth will reduce dysgeusia (loss of taste sensation) as is common with orally delivered P2X3 antagonists.

FEND may reduce cough incidence and increase laryngeal pH in laryngeal hypersensitive patients. A study will be performed using 5% buffered $CaCl_2$ aerosol delivered every 4 hours. Primary efficacy measure will be reduction of cough incidence. Secondary efficacy measures will include: pH laryngeal fluid (CBC), PTP, exhaled aerosol measures, and assessment of inflammation.

Condensation Layers, Airway Lining Fluids, and ATP Concentration

The inventors sought a basic quantitative understanding of condensation layers as relates to these questions and their implications to respiratory health. Within the model constraints summarized in the Condensation Layer Modeling section, below, the biophysics of airway condensation layers was explored in the limiting circumstances of perturbations around a "base case" of breathing of warm equatorial air (30° C.), with high (60%) and low (10%) relative humidity (RH), nasal or mouth inhalation, and exhalation times of 1, 2 or 5 seconds, ranging from fast to slow breathing. Also explored was the impact of elevated breathing rate, as occurs in sustained high-exertion exercise, meaning a high minute volume (assumed 100 L/min) and duration of approximately 1 hour or more, being the approximate time reported from in vitro experiments for PCL height to change to the levels predicted in our steady-state time-averaged analysis. To provide further insight, a relationship was sought between quantitative predictions and micro-structural parameters of the mucus hydrogel using a classical hydrodynamic model of osmosis. Using assumptions summarized in the Condensation Layer Modeling section, discussed below, an estimate was made of a degree of time-averaged structural evolution of upper airway lining fluid during sustained normal tidal breathing for an airway lining fluid containing the principal salts of the airways (sodium, potassium, calcium and magnesium chloride) and water, and also following the rehydration of the ALF by the topical delivery of hypertonic salines. The results of the research are included herein.

Results Regarding Condensation Layers, Airway Lining Fluids, and ATP Concentration Biophysical Model Evaporation from the airways during normal tidal breathing promotes osmotic movement of water through the ALF toward the air surface by way of an imbalance of osmolytes (salt cations) above and below the mucus layer. This imbalance can be expressed by time-averaged condensation layer salt concentration:

$$\overline{C_c} = C_* \left(1 + \frac{\overline{Q_e}\chi}{PE_{epith}} + \frac{\overline{Q_e}\chi}{PE_m}\right) \quad (1)$$

and time-averaged PCL concentration:

$$\overline{C_{PCL}} = C_* \left(1 + \frac{\overline{Q_e}\chi}{PE_{epith}}\right) \quad (2)$$

relative to the salt concentration of the surrounding tissue, $C^*$. Here, an over bar denotes a time average (over many identical tidal breaths), and evaporation and ALF transport is characterized by the average mass rate of water evaporation, $Q_e$ (mg/s), with $PE_m$ the mass permeability of the mucus (mg/s), and $PE_{epith}$ the net (transcellular and paracellular) mass permeability of the epithelium (mg/s).

The osmotic pressure imbalance expressed by Eqs (1) and (2) pulls water from epithelial cells and surrounding tissues into the PCL and up through the condensation layer. Moisture that is supplied via osmotic water movement to the condensation layer is characterized by an airway dehydration factor $\chi$ where:

$$\chi = \frac{V_{sat}}{V_{exh}} \left(1 - \frac{RH_{inh}}{100}\right) \quad (3)$$

with $RH_{inh}$ the relative humidity of inhaled air entering the carina, $V_{sat}$ the air volume from the carina to the generation of airways beyond which complete water saturation is attained, and $V_{TV}$ is the tidal volume. The factor $\chi$ expresses the fractional degree to which evaporation from the upper airways is supplied by water drawn from the ALF versus water that has been condensed from air emanating from the central and lower airways.

The higher salt concentration in the condensation layer [see Eq (1) above] relative to the PCL [see Eq (2)] produces a pressure force on the air lumen side of the (water permeating) mucus that displaces the mucus toward the epithelium, reducing the thickness of the PCL over many breaths of inhalation and exhalation time T by an amount:

$$\bar{l}_{PCL} = l^0_{PCL} - \frac{1}{2}\overline{Q_e}T\frac{\chi}{\rho A} \quad (4)$$

where A is the cross-sectional area of the airways and $\rho$ the mass density of water. In most circumstances, including those of healthy hydrated airways, the condensation layer thickens to approximately the same extent:

$$\bar{l}_c = \frac{l^0_c + l^0_{PCL} - (l^0_{PCL} - \frac{1}{2}\frac{\overline{Q_e}\chi T}{\rho A}(1 + \overline{Q_e}\chi/\overline{PE_{epith}})}{1 + \overline{Q_e}\chi/\overline{PE_{epith}} + \overline{Q_e}\chi/\overline{PE_m}} \quad (5)$$

as is more obvious in the healthy circumstance of high mucus and epithelial water permeabilities, notably $$\bar{l}_c \approx l^0_c + \frac{1}{2}\frac{\overline{Q_e}\chi T}{\rho A} \quad (6)$$

The PCL thins therefore in a very intuitive way. In perfectly hydrated conditions ($\chi$=0) the layer does not thin. In dehydrated airways (1>$\chi$>0), and in those conditions where a condensation layer remains above the mucus, thinning of the PCL is counterbalanced by the thickening of the condensation layer, so that the ALF volume is nearly perfectly conserved. The condensation layer thickens [see Eq (6)] to the same amount the PCL thins reflecting a pure displacement of the mucus downward into the ALF—with water moving up through the pores of the mucus to supply water to the condensation layer and hydrate inhaled air.

Setting the left side of Eq (5) to zero leads to the definition of a critical epithelial permeability $$\overline{PE_{epith}}^{CRIT} = \chi\overline{Q_e}\left(\frac{l^0_{PCL} - \frac{1}{2}\frac{\overline{Q_e}\chi T}{\rho A}}{l^0_c + \frac{1}{2}\frac{\overline{Q_e}\chi T}{\rho A}}\right) \quad (7)$$

characterizing a condition where the airway epithelium is unable to supply the water needed to hydrate inhaled air. The condensation layer in this case disappears. At values of epithelial permeability below the critical value (above) the condensation layer thickness becomes negative, and the water/air surface begins to recede into the mucus, with the mucus drying out. A similar loss of condensation layer thickness can occur when the mucus permeability becomes vanishingly small [see Eq (5)], as on shrinkage of the mucus hydrogel (increase in solids content) during drying, acidification, and evolution of ionic composition. With low mucus permeability, the thickness of the condensation layer becomes vanishingly small, while it does not entirely disappear so long as epithelial permeation is sufficiently large.

The displacement of mucus and loss of PCL volume that occurs due to evaporative draw of water, stresses underlying cilia and releases ATP, both of which alter cilia beat and enhance inflammation. Forces applied to cilia tips as via interactions with a displaced mucus have been shown to be sufficient to stimulate stretch-activated membrane channels, enhancing acidity and reducing cilia beat frequency, and to increase inflammatory markers including cytokines such as interleukin-1$\beta$ (IL-1$\beta$), interleukin-6 (IL-6) and tumor necrosis factor-$\alpha$ (TNF-$\alpha$).

For small deformations of cilia (small diminution of PCL thickness relative to the hydrated thickness), the concentration of inflammatory markers can be estimated to first-order approximation by a linear relation between cilia deformation and time-averaged ALF $$\overline{CI}(ALFBiomarkers): \begin{cases} \overline{CI_{ATP}} \approx CI0_{ATP}\left[1 + \alpha_{ATP}\frac{\overline{Q_e}T\chi}{A}\right] \\ \overline{CI_{CYTO}} \approx CI0_{CYTO}\left[1 + \alpha_I\frac{\overline{Q_e}T\chi}{A}\right] \end{cases}$$

biomarker concentration (CI) by relative to baseline values $CI0_{ATP}$, $CI0_{CYTO}$ and dimensional inflammatory constants $\alpha_{ALF}$, $\alpha_{CYTO}$.

Contact between the mucus and cilia also reduces cilia beat frequency (CBF), which to first-degree approximation can similarly be expressed relative to a hydrated state $CBF_0$ and dimensionless CBF constant $\alpha_{CBF}$ $$\overline{CBF} \approx CBF_0\left[1 + \alpha_{CBF}\frac{\overline{Q_e}T\chi}{A}\right] \quad (9)$$

Loss of ALF volume, as occurs with inadequate permeation of mucus or epithelial layers, increases nonvolatile solute concentration in the ALF as well [see Eq (1)]. The impact of ALF volume reduction on surfactants present in the ALF is to increase surface elasticity, which enhances the tendency for surface breakup under the shear flow of air that occurs during inhalation. This phenomenon, which scales in proportion to the Capillary Number (Ca=$\mu u_a/\gamma$, where $\mu$ is the viscosity of water, $u_a$ a characteristic air velocity, and $\gamma$ the surface tension), promotes the generation of respiratory droplets as can be measured in the form of exhaled breath particles, or EBP. We estimate EBP to first-order approximation by a linear relation to condensation layer solute concentration [see Eq (1)] relative to a hydrated state $EBP_0$, with $\alpha_{EBP}$ a dimensionless breakup constant:

$$\overline{EBP} \approx EBP_0\left[1 + \frac{\overline{Q_e}\chi}{\overline{PE_m}} + \frac{\overline{Q_e}\chi}{\overline{PE_{epith}}}\right] \quad (10)$$

PCL thickness can be restored, and dysfunction reduced, by deposition of hypertonic saline on the surface of the ALF. Unlike the case of isotonic saline, for which deposition on the surface of ALF increases the condensation layer thickness without increasing PCL thickness and therefore is incapable of modulating dysfunction, deposition of hypertonic saline with concentration $C_D$ may raise the tonicity of the ALF sufficiently to hydrate the PCL by osmotic dehydration of epithelial cells. This mass can be estimated by a simple mass balance, assuming uniform deposition of a mass of hypertonic droplets $M_D$ in the upper airways (nose and trachea). The salt concentration of deposited droplets needed to raise the tonicity of the upper airway ALF mass $M_{ALF}$) to regain the volume of PCL lost through dehydration is therefore:

$$C_D = C_* \left[ \left(1 + \frac{\overline{d}}{l_{c0} + l_{m0} + l_{PCL0}}\right)\left(\frac{M^0_{ALF}}{M_D} + 1\right) - \frac{M^0_{ALF}}{M_D} \right]$$

Deposition in the nose, larynx and trachea (where the majority of water evaporation occurs on inhalation) of hypertonic droplets of mass $M_D$ and concentration $C_D$ will then restore the hydrated height of the PCL for the duration of time required for clearance of the added salts by transcellular and paracellular pathways of epithelial permeation. In the circumstances of small displacement of the mucus, as with the above estimates, Eq (11) simplifies to the following expression for the needed mass of hypertonic salt in the upper airways to restore the PCL volume:

$$M_D \approx \frac{\overline{d} M^0_{ALF} C_*/C_D}{l^0_c + l^0_m + l^0_{PCL}} \quad (12)$$

Equation (12) expresses the relationship that the mass of salt water deposited on the upper airway surface (A) divided by the total mass of ALF in the upper airways, should compensate in hypertonic concentration $C_D$ to draw by osmosis from epithelial cells the water volume required to restore the PCL volume loss represented by the mucus displacement [see Eq (4)].

Dehydration, Dysfunction and the Triggering of Cough Reflex

A base case was evaluated of the nasal or mouth breathing of warm air (30° C.) in several circumstances of human breathing ranging from dry (10% RH) to moist (60% RH) air. All cases assume a tidal volume of 0.5 L with fast (T=1 s), moderate (T=2 s) and slow (T=5 s) breaths. Assuming a 1 second (s) transition from inhalation to exhalation, these cases correspond to a range of 20 breaths per minute (T=1 s) to 5-6 breaths per minute (T=5 s). Also considered was the case of mouth breathing during strenuous exercise (increasing the ventilation rate by a factor 5 from the fast breathing case, i.e. from 20 L/min to 100 L/min). Table 1 in FIG. 8 summarizes the principal dehydration characteristics appearing in Eq (1) to Eq (4) in these circumstances.

As can be seen by the values of the airway dehydration factor $\chi$ (Table 1), slow nasal inhalation of dry (10% RH) and humid (60%) RH air leads, according to Eq (3), to nearly complete hydration of inhaled air within the upper airways ($\chi$=0). The consequence is that, while some dehydration occurs beyond the carina, inhaled air humidity is nearly 90% from the carina and the condensation layer is nearly completely restored by condensation of water on exhalation (i.e., $\chi$~0). In an opposite extreme of fast (T=1 s) mouth breathing, $\chi$=0.3, and very dry air passes the carina (10% RH), penetrating as far as generation 17, beyond which the airways begin to branch into the alveolar sacs.

Strenuous exercise (meaning in our analysis a sustained breathing of air at 100 L/min), which amplifies the evaporation of water in the trachea owing to a far faster rate of air flow, leads to a similar degree of dehydration as the mouth breathing of dry air ($\chi$=0.3), while the steady-state time-averaged thinning of the PCL (Table 1, FIG. 8) is far more severe on exercise (1.5 µm), roughly a 20% diminution of the PCL thickness relative to the fully hydrated state. This results from the fact [see Eq (4)] that the rate of osmotic water transport via the mucus is elevated during exercise (elevation of mean tracheal air velocity of 5x in comparison to the sedentary mouth-breathing case), thinning the PCL. The mass rate of water evaporation ($Q_e$) varies with ambient humidity and speed of inhalation between a total evaporative loss of water mass ($Q_e T$) of approximately 1 to 16 mg in the upper airways.

Figure 9A:
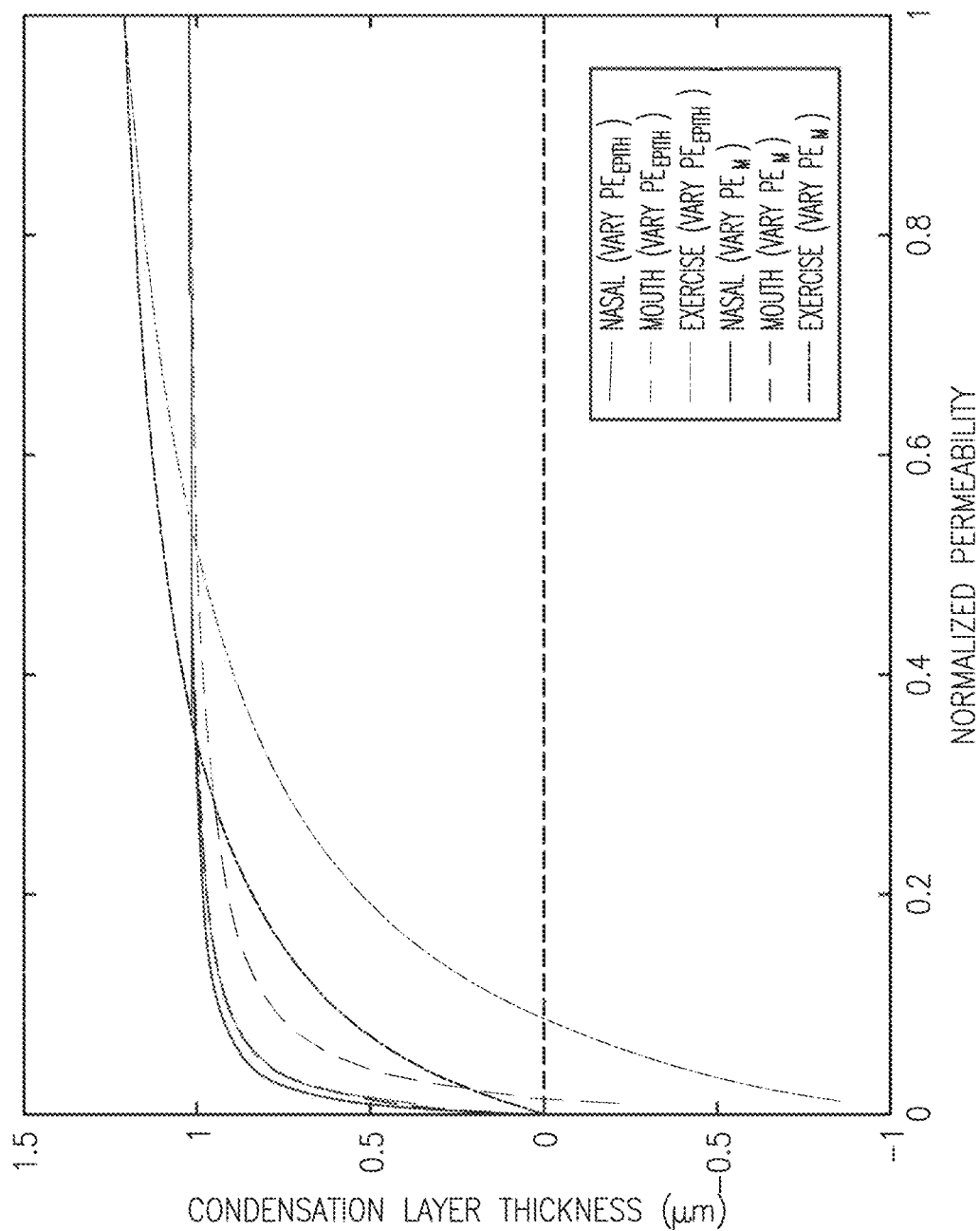
FIG. 9A is a graph showing a time averaged condensation layer thickness versus a permeability of a mucus or epithelial cell layer normalized by a permeability value in fully hydrated conditions (100 µm/s) on fast (T=1 s) breathing of dry air (10% RH), according to at least one illustrated embodiment.
Figure 9B:
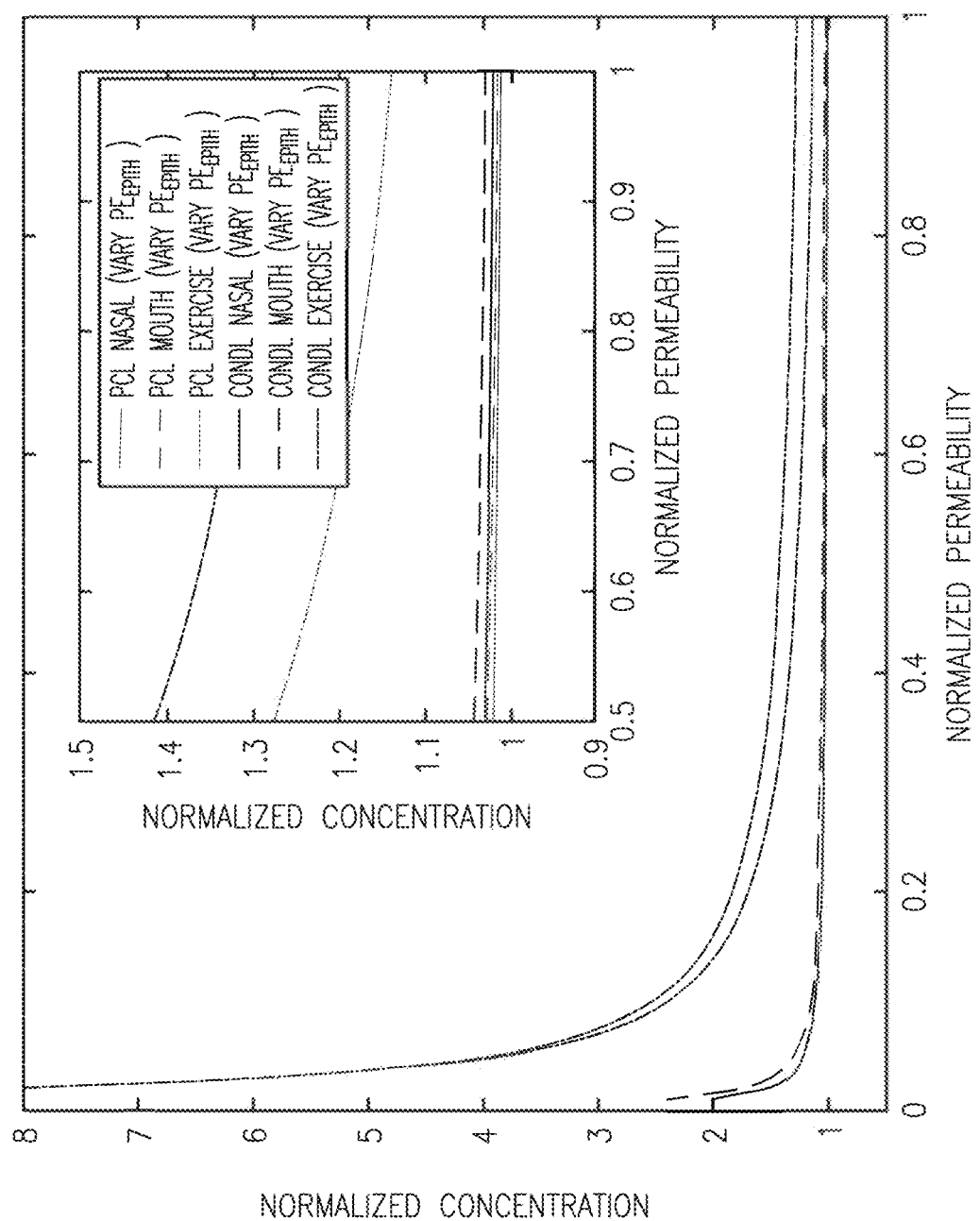
FIG. 9B is a graph a time averaged normalized salt concentration versus a permeability of a mucus or epithelial cell layer normalized by a permeability value in fully hydrated conditions (100 µm/s) on fast (T=1 s) breathing of dry air (10% RH), according to at least one illustrated embodiment.

FIGS. 9A and 9B respectively show a plot of the condensation layer thickness and a plot of salt concentration [Eqs (5) and (1)] on the fast (T=1 s) breathing of dry air (10% RH) versus the permeability of the mucus or epithelial cell layer normalized by the permeability value in fully hydrated conditions (100 µm/s). At high water permeation, water evaporation in the upper airways increases the thickness and salt concentration of the condensation layer to a small degree relative to fully hydrated conditions in all conditions other than the case of mouth breathing of dry air (see insert of FIG. 9B) and especially the case of strenuous exercise. At low water permeation, as may occur at low pH or with the drying out of the mucus, condensation layer thickness can fall, and even recede into the mucus (negative condensation layer thickness), and salt concentration can rise precipitously. Loss of condensation layer thickness may occur within the range of reported values of mucus and epithelia water permeabilities (approximately 1 to 150 µm/s) for the case of strenuous exercise. Drying out the mucus (negative condensation layer thickness) is less likely while can occur with exercise (FIG. 9A) at about 20% of the normalized epithelial membrane permeability, and around 10% of this value in the case of fast mouth breathing of dry air. Otherwise, with nasal breathing, and especially with slow nasal breathing, the condensation layer is robust, the mucus remains hydrated, and the ALF volume is conserved.

An estimated $\alpha_{ALF}$~1.4 was determined by fitting Eq (8) to the measured rise of extracellular ATP release on the placing of a mucus mimetic hydrogel over an in vitro monolayer of ciliated epithelial cells and increasing the cilia stress linearly in proportion to hydrogel solids content. The predictions of ATP and inflammatory cytokine concentration, CBF reduction and EBP augmentation in all the cases of normal tidal breathing and exercise considered here, are shown in Table 2 illustrated in FIG. 10. The predictions used ($\alpha_{CTYO}$~0.28, $\alpha_{CBF}$~0.15, $\alpha_{CBP}$~21.3) and an average epithelial water permeability~20 µm/s by comparison of the predictions with experimental data in the case of strenuous exercise as further described below. Strenuous exercise and mouth breathing of dry air each produce the greatest rise in ATP concentration, and are most inflammatory (Table 2, FIG. 10), with the greatest reduction in CBF and elevation of EBP. Fast mouth breathing of dry air not only creates significant inflammation in the upper airways (Table 2, FIG. 10), these conditions extend far into the airways, as can be seen by the deep penetration of dry air for these cases (10% RH tidal breathing and exercise) from Table 1, FIG. 8.

Table 2 shown in FIG. 10 also summarizes the masses of topically deposited 5% hypertonic salt solution that restore the PCL thickness in the nose, larynx and trachea. As these estimates are based on the assumption of uniform deposition in the nose, larynx and trachea, and depending on the mass median aerodynamic diameter of the nasally inhaled solution [a 10 µm droplet inhaled via the nose deposits approximately 70% of the inhaled mass in the nose and 30% in the larynx and trachea], larger masses may be used, notably if the targeted tissue is the larynx and/or the trachea.

The predictions of airway inflammation and EBP were compared with experimental findings in the most dehydrating conditions of strenuous exercise and mouth breathing of dry air. Four published reports of strenuous exercise were considered, denominated as: Osaka study (i.e., Tatsuya, U, Yoshikawa, T, Ueda, YK, Orita, K, Fujimoto, S. Effects of acute prolonged strenuous exercise on the salivary stress markers and inflammatory cytokines. Japanese Journal of Physical Fitness and Sports Medicine, 2011, Volume 60, Issue 3, Pages 295-304), Boston study (i.e., C George, G Scheuch, U Seifart, L Inbaraj, S Chandrasingh, I Nair, A Hickey, M Barer, E Fletcher, R Field, J Salzman, N Moelis, D Ausiello, D. A. Edwards. COVID-19 symptoms reduce with targeted hydration of the nose, larynx and trachea. *Sci. Rep.* 12, Article number: 4599 (2022)); Munich study (i.e., Mutsch B, Heiber M, Grätz F, Hain R, Schönfelder M, Kaps S, Schranner D, Kähler C J, Wackerhage H. Aerosol particle emission increases exponentially above moderate exercise intensity resulting in superemission during maximal exercise. Proc Natl Acad Sci USA. 2022 May 31; 119(22): e2202521119. doi: 10.1073/pnas.2202521119. Epub 2022 May 23. PMID: 35605123; PMCID: PMC9295808); and Nebraska study (i.e., Müns G, Singer P, Wolf F, Rubinstein I. Impaired nasal mucociliary clearance in long-distance runners. Int J Sports Med. 1995 May; 16(4):209-13. doi: 10.1055/s-2007-972993. PMID: 7657412). In the Osaka, Boston and Munich studies, human subjects worked out on exercise machines for one hour. Inflammatory cytokines and salinity were measured in the saliva of the athletes in the Osaka study, before and after exercise, while EBP was measured before and after exercise in the Boston and Munich studies. These three studies were performed indoors at or near 25° C. without report of ambient relative humidity. In the Nebraska study, subjects ran a marathon in cold (4° C.) conditions, and nasal CBF was evaluated before and after the race and compared to a sedentary control group. Predictions based on Eqs (8)-(10) were compared with the findings of these studies using the parameters summarized Table 2, FIG. 10. Based on these same parameter values, the predictions were compared with experimental findings obtained in sedentary conditions from a Cambridge study (i.e., Edwards. David. A., Brenner, H. and Wasan, D. T. 1991 *Interfacial Transport Processes and Rheology.* Boston, MA: Butterworth-Heinemann, 558 pp.) of human subjects mouth breathing dry and humid air, and following the nasal inhalation of 5% hypertonic salines. The primary results of these comparisons are summarized in FIGS. 11A and 11B.

Figure 11A:
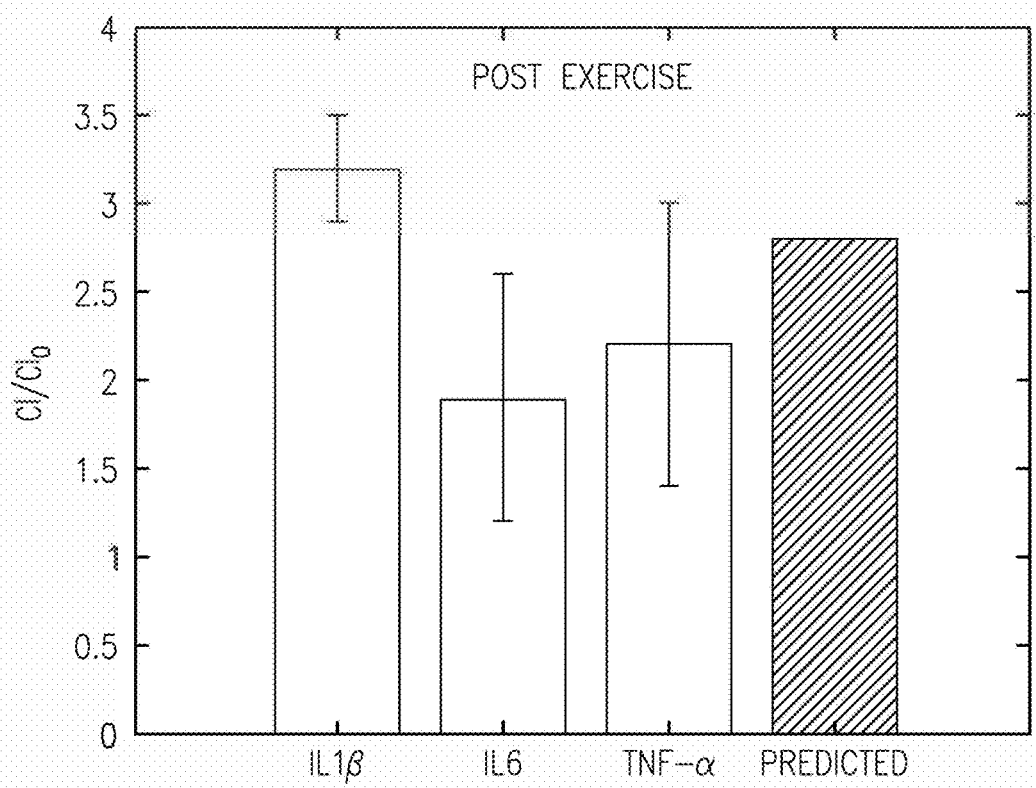
FIG. 11A is a graph showing inflammatory cytokine data from three exercise studies in Osaka, Boston and Munich, according to at least one illustrated embodiment.
Figure 11B:
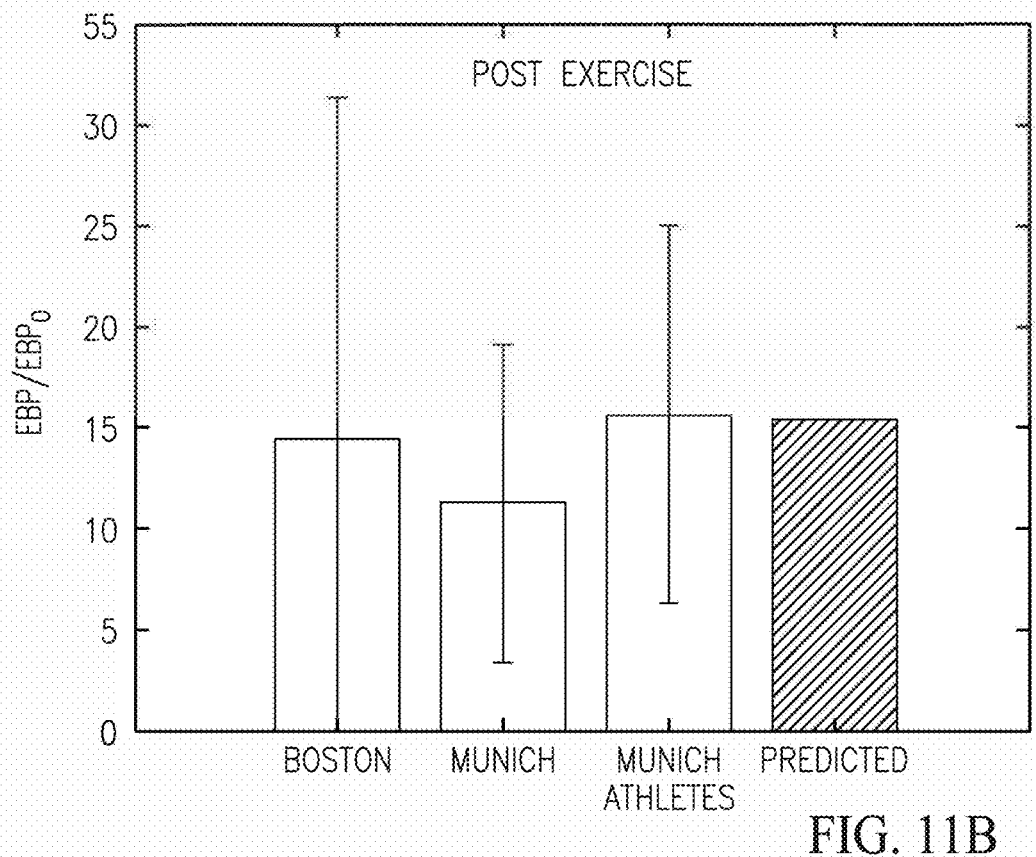
FIG. 11B is a graph showing exhaled breath particle data from three exercise studies in Osaka, Boston and Munich, according to at least one illustrated embodiment.

FIGS. 11A and 11B show the inflammatory cytokine and exhaled breath particle data from three exercise studies in Osaka, Boston and Munich. Elevated inflammatory cytokines, and highly elevated exhaled breath particles, reflect dehydration of the airways, as is confirmed by the theoretical predictions based on Eq (8) and Eq (10). The more elevated EBP in seasoned athletes observed in the Munich study relative to non-seasoned athletes is insignificant as are differences between the Munich and Boston results. In both the Boston study (where all participants were fit athletes) and the Munich study, variability in exhaled aerosol increased dramatically with exercise.

Figure 11C:
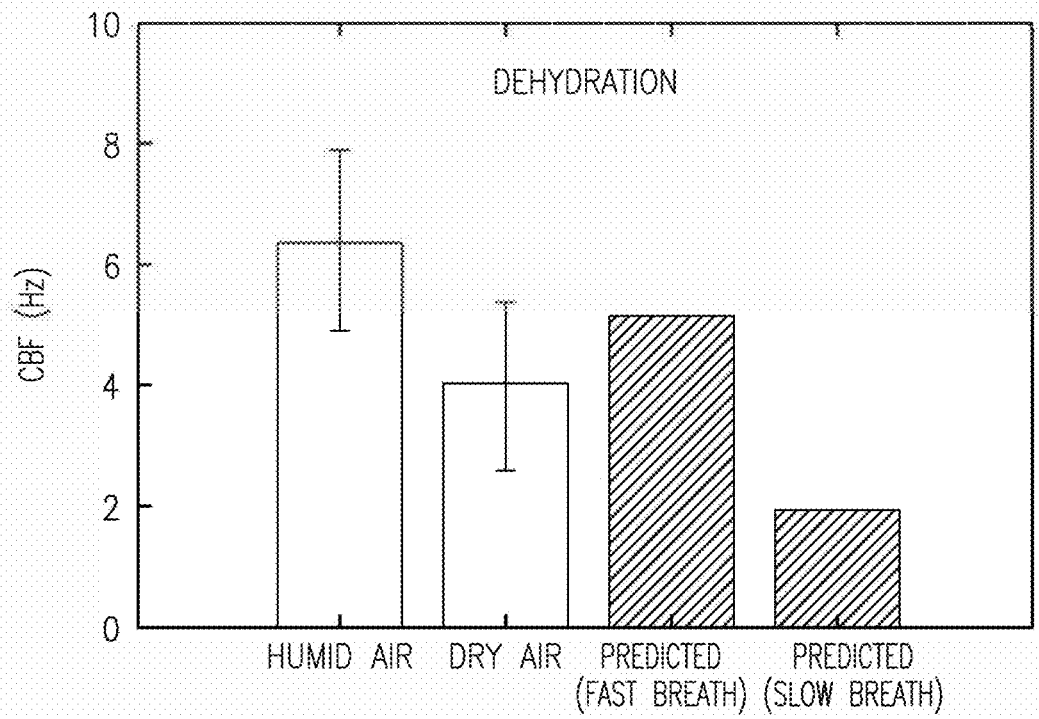
FIG. 11C is a graph showing cilia beat frequency (CBF) data following exposure to humid and dry air from studies in Mannheim and Cambridge, MA, according to at least one illustrated embodiment.
Figure 11D:
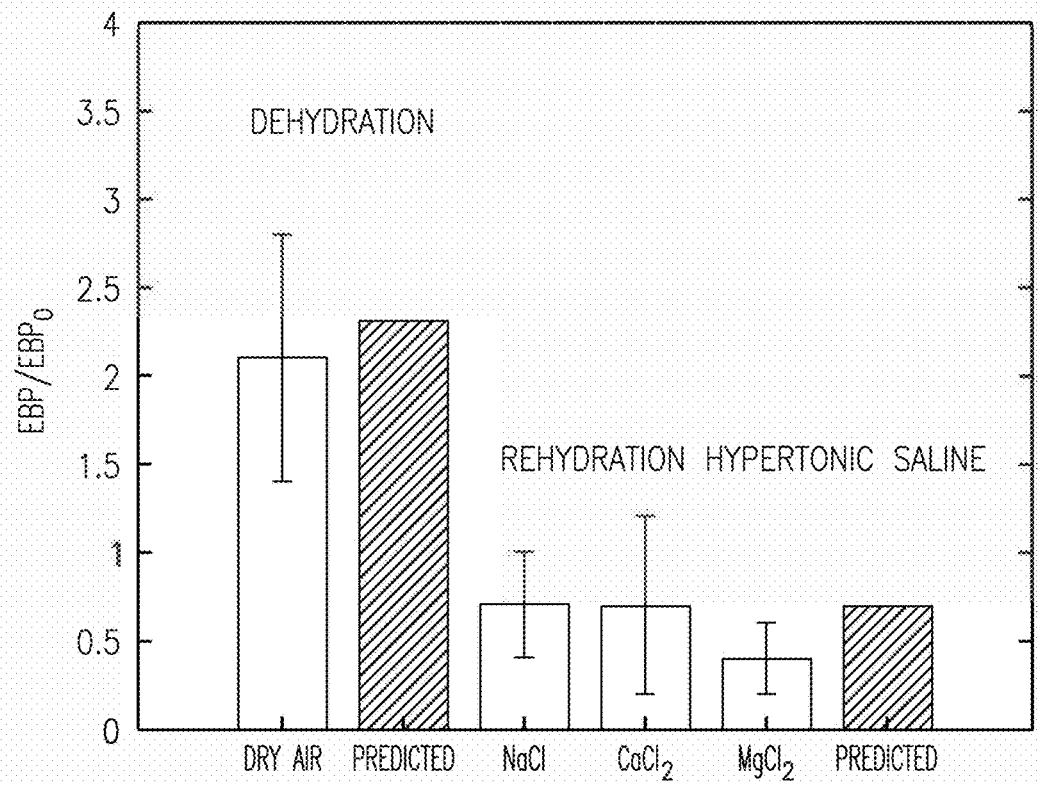
FIG. 11D is a graph showing exhaled breath particle (EBP) data following exposure to humid and dry air from studies in Mannheim and Cambridge, MA, according to at least one illustrated embodiment.
Figure 12A:
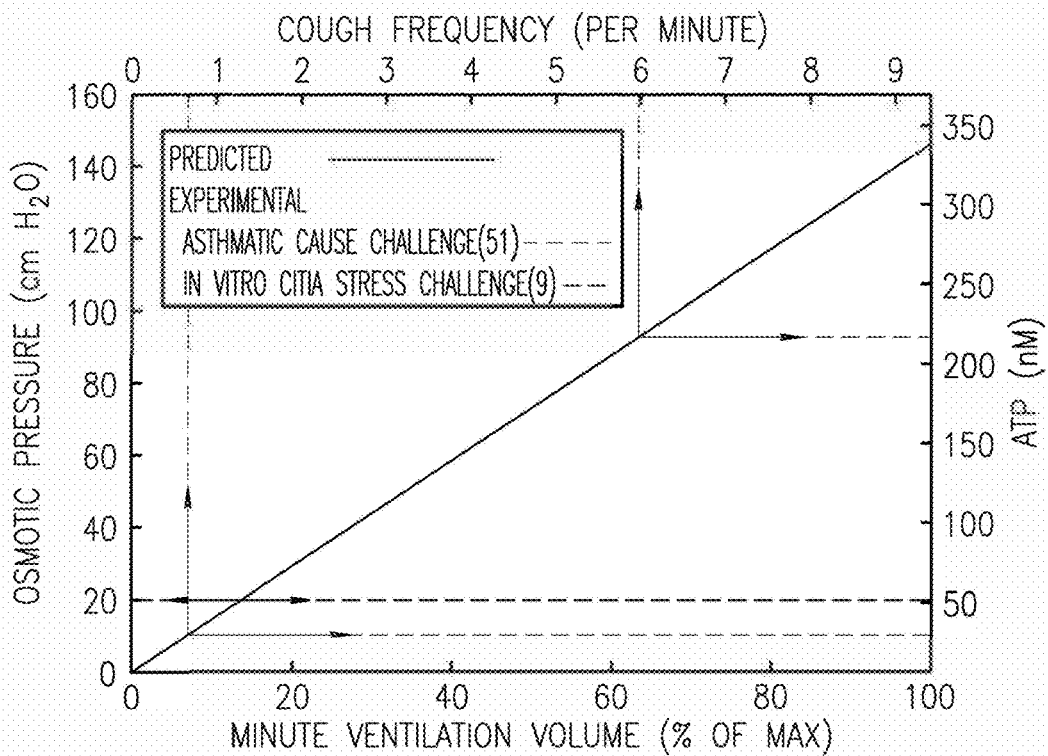
FIG. 12A is a graph showing cough incidence (number of coughs) versus minute volume as a percentage of maximum minute volume following deep breathing of dry air for a set of healthy subjects, according to at least one illustrated embodiment.
Figure 12B:
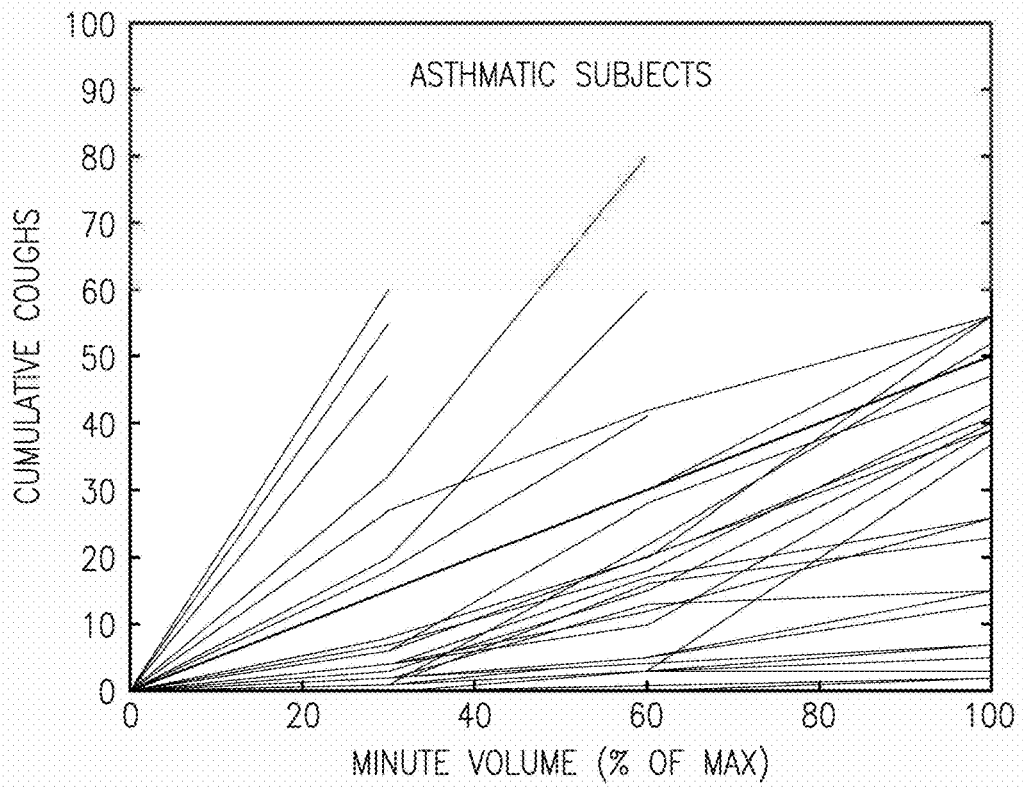
FIG. 12B is a graph showing cough incidence (number of coughs) versus minute volume as a percentage of maximum minute volume following deep breathing of dry air for a set of asthmatic subjects, according to at least one illustrated embodiment.

FIGS. 11C and 11D show the cilia beat frequency (CBF) and exhaled breath particle (EBP) data following exposure to humid and dry air in Mannheim and Cambridge studies.

In the Mannheim study (FIG. 11C), newly tracheotomized patients were treated either with cool (ambient temperature) dry (compressed) air and nebulization of isotonic saline or heated (37° C.) humidified (100% RH) air eight hours per day for 14 days post tracheotomy. Epithelial tracheal cells were harvested at days 2, 4, 6, 8 and 10 post surgery and CBF measured in vitro in both (non-randomized) groups. We predicted the EBF reduction from the results of Table 2 assuming the baseline (perfectly humid) $CBF_0$=6.4 Hz, and the mouth-breathing (no nasal humidification) 30° C., 10% RH case with time of inhalation either 1 s or 5 s (breaths per minute were unspecified in the study). We assumed the nebulization of isotonic saline would have no impact on CBF given the absence of osmotic gradient to hydrate the PCL—as has been confirmed experimentally elsewhere. The reduction of CBF in the cold air tracheotomized patients relative to the perfectly humid air is in the range of the predicted values based on the mechanism of the mucus membrane displacement that follows the thinning of the PCL without ALF volume loss (owing to the thickening of the condensation layer).

In the Cambridge study (FIG. 11D), human subjects breathed ambient (25° C.) humid (40-50% RH) air for 20 minutes, then moved into a dry air (10% RH) ambient temperature environment where they remained for 2 hours. EBF increased over 2-fold in the study on moving from the humid to the dry air environment. Our prediction is based on the mouth-breathing 30° C., 10% RH and 60% RH cases with time of inhalation 1 s. A similar rise in respiratory droplets is predicted based on the mechanism of the concentrating of non-evaporating solutes (surfactants) in the condensation layer that occurs in the dry air condition. Following the breathing of the dry air for 2 h, the subjects in the Cambridge study inhaled approximately 10 mg of 5% hypertonic saline (with either NaCl, or $CaCl_2$, or $MgCl_2$) amounting to an estimated 3 mg deposition in the larynx and trachea based on a mass-median droplet diameter of around 10 μm. The reduction in EBF measured in the study in all three hypertonic saline cases is predicted on the basis of the 2.5 mg 5% hypertonic saline case of Table 2, FIG. 10, relative to the dry air (10% RH) case and based on the mechanism of the restoration of PCL thickness that occurs owing to the osmotic action of the hypertonic salts on the epithelial cell layer. The similar degrees of suppression observed for EBP with hypertonic 5% NaCl, or $CaCl_2$, or $MgCl_2$, aligns with the osmotic mechanism, while the time duration of the salt rehydration will vary depending on clearance times, sodium clearing more rapidly than calcium and magnesium, as reported in the Cambridge study and has been reported elsewhere.

It was sought to understand the relevance of these dehydration-driven changes to upper airway function to propensity to cough. Incidence of chronic cough has been reported to grow approximately linearly with ATP concentration on topical deposition of ATP in healthy normal and asthmatic human subjects, with a marked dependence on ATP in the case of (hyper-responsive) asthmatic airways and a weak dependence in the case of healthy airways. Given a linear relationship between cough/ATP concentration and the dependence of ATP concentration on breathing parameters in Eq (8), we determined the following approximate relations between cough frequency (coughs per minute), dryness of the airways ($\chi$), inhalation period (T) and rate of evaporation ($Q_e$) (proportional to speed of inhalation or minute volume)

$$\overline{CF_N} \approx \alpha_{CF} ClO_{ATP} \frac{Q_e T \chi}{A} \qquad (13a)$$

-continued $$\overline{CF_{HS}} \approx \beta_{CF} CI0_{ATP} \frac{\overline{Q_e} T \chi}{A} \quad (13b)$$

where the baseline ATP concentration is $CI0_{ATP}$ and the parameters ($\alpha_{CF}$, $\beta_{CF}$) reflect the degree of sensitivity of the upper airways to cough triggers in normal and hypersensitive airways, and with the ratio of mass flux across the mucus to area of the airways expressed in mg/cm².

Inventors independently determined the values of ($\alpha_{CF}$, $\beta_{CF}$) in Eqs (13a, 13b) by comparing cough frequencies reported by for normal (healthy) and hypersensitive (asthmatic) human subjects following ATP delivery. We specifically examined the case in of topical aerosols with 1 μM, given the known tracheal deposition profile of 3 μm droplets at 15 L/min air flow and the precise nature of the delivery technique used in the study. Notably, aerosol delivery of 1 μM ATP produces a roughly 50 nM increase in ATP in the tracheal fluid, which is on the order of magnitude of ATP elevation measured following the stressing of cilia by a constraining mucus hydrogel layer. Note also that in the latter study, ATP concentration rises from a baseline of near 10 nM to around 80 nM as the solids content rises from a mass fraction of around 0.05 (similar to hydrated mucus) to around 0.3, which is approximately equal to the dehydration factor ($\chi$) following the mouth breathing of dry. We then determined from this comparison ($CI0_{ATP}$=10 nM) and ($\alpha_{CF}$=0.5, $\beta_{CF}$=30).

We considered the rise in cough incidence reported by Purokivi et al on the delivery of isocapnic hypernea of dry air (deep breathing of dry air with 5% $CO_2$) to the airways of healthy and asthmatic patients. In this random control study, coughs post challenge were monitored for up to 10 minutes, while most of the coughing occurred in the first minute post the challenge. To compare with theoretical predictions, we assumed the 10% RH case of Tables 1 and 2 with healthy and asthmatic patients deep breathing (T=5 s). For the normal and hypersensitive (asthmatic) cases of Eq (13) we used the values of ($CI0_{ATP}$=10 nM) and ($\alpha_{CF}$=0.5, $\beta_{CF}$=30) as deduced from the independent studies. The results of our comparisons are shown in FIGS. 12A and 12B.

ATP concentration rises in the airways of both normal and asthmatic subjects, while the hypersensitivity to ATP leads to a far greater cough incidence among the asthmatics (FIG. 12B). This cough incidence increases with increasing minute volume precisely given the dependence of PCL thickness on evaporation rate [see Eq (4)]. This growing propensity to cough on increased minute volume does not implicate ALF volume loss, as can be seen on consideration of Table 1 (FIG. 8) and FIGS. (9A and 9B), notably given the parallel and related thickening of the condensation layer [see Eq (5)].

Discussion Regarding ATP Concentration

Dehydration of the upper and central airways harms respiratory health and is a particular threat to human life given the worsening quality of air on the planet. The nature of this dehydration appears to be intimately related to the existence of a mucus condensation layer, simultaneously by its relationship to how and to what we breathe.

Our analysis indicates that the condensation layer is best preserved by the slow nasal breathing of around 6 breaths per minute (Table 1, FIG. 8). Over the range of dry (10% RH) to moist (60% RH) warm air environments considered here, slow nasal breathing nearly perfectly humidifies inhaled air as it passes beyond the carina, and as a consequence the upper airway condensation layer is almost entirely restored by water condensed from super-saturated air on exhalation (Table 1, FIG. 2). This greatly reduces the amount of water pulled via the mucus to hydrate inhaled air ($\chi$~0), so that very little displacement of the mucus occurs (Table 1), and cilia beat relatively freely and naturally (Table 2, FIG. 10).

We find that fast mouth breathing of dry air poses the greatest risk to the condensation layer on normal tidal breathing (Table 1, FIG. 8). The rapid movement of air, and the inability of the nose to humidify inhaled air, are such that dry air (as low as 10% RH, Table 1) penetrates the carina and dehydrates the airways as far as generation 17 of the airway tree (Table 1, FIG. 8 and Table 2, FIG. 10). With sustained mouth breathing of dry air the condensation layer can lose volume (FIGS. 9A, 9B), amplifying inflammation i.e. Eq (8), reducing CBF i.e. Eq (9), and increasing the generating of respiratory droplets i.e. Eq (10) (see Table 2, FIG. 10). These trends are reflected in comparison of theoretical predictions with experimental data shown in FIGS. 11A, 11B, 11C and 11D.

Our predictions of an approximately 40% diminution in the evaporation of water from the upper airways by mouth breathing of dry air versus nasal breathing (see e.g. the evaporative water losses reported in Table 1, FIG. 8 for 10% RH on fast nose and mouth breathing) imply a similar loss in upper airway water condensation on exhalation. This prediction aligns with a reported 42% increase in exhaled water condensate on oral versus nasal breathing. Our results reflect the poor hydration of air that occurs in the mouth relative to the nose, and therefore a greater evaporative stress on the larynx in the circumstance of mouth breathing, as has also been reported in relation to phonation effort and the evaporation of superficial water on the vocal folds. These results are also consistent with the rapid slowing of mucociliary clearance reported in cases of tracheotomies where dry air directly enters the trachea.

ATP release into ALF increases with airway dehydration (Eq 13) and notably with increasing minute volume or evaporation rate (Eq 13). As a consequence the most highly inflammatory conditions of normal breathing occur on strenuous exercise (Table 2, FIG. 10), consistent with experimental findings (FIGS. 11A, 11B, 11C and 11D) and presumably a contributing factor to respiratory health risks of high-endurance and elite athletes.

Our prediction that strenuous exercise produces an order of magnitude more respiratory droplets in the airways relative to sedentary conditions aligns with two recent independent experimental studies. The similar degrees of amplification of EBP in the two studies, even while the exercise routines were not identical (while breathing intensity and duration may be), is at least consistent with our prediction of an amplification in EBP entirely related to the combination of mouth breathing and very high inhaled air speed in the upper airways. While the health relevance of high EBP deserves further study, phenomena of airborne infectious disease spread in gymnasia, and the propensity of athletes to suffer from upper respiratory tract infections may be related.

That inflammatory conditions of airway dehydration may arise even in the absence of ALF volume loss does not appear to have been postulated previously. Our analysis suggests that the thinning of the PCL that occurs inevitably with the osmotic movement of water through the ALF produces airway stress and can lead to dysfunction. It is notable in this context that the inflammatory condition of the breathing of dry air (Table 2, FIG. 10) does not involve loss of ALF volume (Table 1, FIG. 8). Water passage via the mucus is simply very great owing to the relative dehydration of the central airways, and this presses the mucus into the PCL, disrupting normal cilia function and augmenting EBP.

Generally, the condensation layer appears to play a critical role in regulating ALF volume, balancing loss of thickness of the PCL that occurs owing to the movement of water out of the PCL and through the mucus to support evaporation. While in normal tidal breathing conditions other than the mouth breathing of dry air, the condensation layer appears to naturally counterbalance volume loss that occurs in the PCL due to water movement into the mucus, the condensation layer can thin, become fragile, and break into respiratory droplets in extreme dehydration circumstances. As the condensation layer begins to lose volume (FIG. 9A) it also increases in salinity (FIG. 9B), raising the risks of inflammation and airway dysfunction (FIGS. 11A, 11B, 11C and 11D).

Hypertonic saline has long been used to rehydrate the airways of cystic fibrosis patients. Our analysis indicates that the deposition of hypertonic salines [as opposed to isotonic salines, which have no impact] on the surface of upper airway lining fluid lifts the mucus above the epithelium, potentially restoring PCL volume that is otherwise lost due to excessive dehydration, and prolonging the restored hydration of the ALF for as long as it takes to clear added salt cations. Sodium ions, the cation most commonly used to promote the hyper osmotic hydration of dry airways, tend to clear from the ALF by diffusion across the apical epithelial membrane via epithelial sodium ion channels within approximately 30 to 60 minutes post administration. Calcium and magnesium ions when delivered to hydrate the upper airways clear more slowly, by a combination of paracellular and transcellular pathways, as in the epithelial absorption of calcium and magnesium in the gut following the ingestion of calcium- and magnesium-rich foods. The amounts of (sodium, potassium, calcium and magnesium chloride) salts added by the delivery of hypertonic salines as prescribed in Table 2, FIG. 10 are small compared to overall salt masses processed by the human body in the course of a single day (1 g $CaCl_2$, 500 mg $MgCl_2$), and are therefore minor relative to recommended daily salt intake. One milligram of 5% hypertonic salt solution that is comprised of 10:1 ratio of calcium to magnesium chloride solution, on depositing uniformly over the nose, larynx and trachea, will approximately double the natural calcium and magnesium chloride solutions in the ALF (see Table 3), while, by comparison, exposure of calcium to gut epithelia on the ingestion of calcium-rich foods, such as whole milk, has been reported to increase normal calcium levels at the gut epithelium by approximately 10-fold.

There are many limitations to our analysis. Our estimates of airway dysfunction are based on very small perturbations in PCL thickness and are therefore insufficient for estimating dysfunction in severely dehydrated airways. Our assumption of warm equatorial air simplified energy considerations, and avoided an obvious circumstance where further airway dehydration occurs, notably on the breathing of cold air (4-6). Breathing cold air leads to air of very low water content (similar to our 10% RH case) while also requiring heating of inhaled air in the upper airways, which reduces evaporation loss, and further prolongs the distance over which the inhaled air needs to travel in the airways to be properly heated and humidified.

In our analysis we assumed effective ion exchange between compartments of the ALF and therefore ignored a special circumstance as occurs in cystic fibrosis where the inability for chloride ions to transport across the epithelial membrane blocks water movement into the airways. This case of very low "effective" epithelial water permeability results in circumstances that in practice resemble very closely what is revealed in FIGS. 9A and 9B in the circumstance of vanishingly small epithelial water permeability. The mucus dries out, and eventually the PCL does as well, resulting in a thickening of the mucus and an adherence of the mucus against the apical epithelial wall.

We did not consider the shrinkage that can occur of the mucus layer owing to the dehydration of mucus, and the evolution of ionic content of the mucus, as can arise in relatively dehydrating breathing circumstances. This phenomenon has recently been studied and shown to produce shrinkage up to approximately 40% of a characteristic gel diameter, meaning a volume reduction of an order of magnitude or more. It is probable that shrinkage of this kind occurs in airway mucus as $\chi$ increases and promotes thinning of the condensation layer and rapid rise in salinity within the condensation layer (see FIGS. 9A and 9B). A similar phenomenon may occur in paracellular water movement and contribute to changes in epithelial permeability with high rates of water egress.

These questions of the dynamic changes that may arise in permeability properties of the mucus and epithelium should be further explored experimentally and theoretically. They may shed important light on dysfunction that occurs in the airways in normal healthy airway circumstances as well as on the progress toward disease.

While our elucidation of condensation layer biophysics aligns with many general observations of airway hydration, dehydration, and dysfunction, further comparison of model predictions with experiments is obviously needed, and assumptions inherent in the model should be relaxed and consequences explored. The coupling of upper airway dehydration with upper airway illnesses, including cough, laryngitis, exercise induced asthma, allergies—as well as lower airway illnesses that are effected by the depth of penetration of dehydration into the airways or by the proliferation of respiratory droplets in the upper airways that occurs in the dehydrated state—should be explored.

With rates of respiratory illnesses continuing to rise around the world, maintaining airway lining water by replenishing the condensation layer via a combination of effective breathing habits and the hydration of inhaled air appears a promising path of further research and translation to hygienic and therapeutic global health practice.

Condensation Layer Modeling Methods

We modeled the biophysics of the condensation layer with the model assumptions summarized in Table 3, FIG. 13. We assumed perfect mixing of air and water within the "compartments" of the nose (and nasal pharynx), trachea (and larynx) and bronchi (and bronchioles) and used upper airways dimensions as reported in the literature for human airways while from the carina to the small airways we assumed Weibel lung geometry. We assumed mass and energy transport to be decoupled by the assumption of warm ambient air and that inhaled air remained at 30° C. from the nose up to the carina and that from the main bronchi the air temperature rose to 35° C.—these temperatures being close to experimental observations in similar conditions. All of our mass transport considerations assumed steady or nearly steady state flow conditions representing time-averages of inhalation, exhalation, and cycles of repetitive tidal breathing. We assumed a base case of warm equatorial air (30° C.), with high (60%) and low (10%) relative humidity (RH), and inhalation and exhalation times of 1, 2 or 5 seconds, ranging from fast to slow breathing. We also considered a case of "exercise," as a special case of fast mouth breathing with a velocity of air flow 5 times elevated relative to normal breathing.

Given the very thin ALF relative to the curvature radii of the airways (ranging from hundreds of microns to several millimeters), we assumed the ALF to be essentially flat and of "infinite" lateral dimension, with the principal physics of water and ion transport occurring in one dimension (FIG. 1). Fully hydrated ALF is assumed to be 30 microns thick in the nose and tracheal compartments, and 10 microns thick from the carina to the small airways, with a periciliary layer (PCL) of structured water of approximately 7 microns thickness, covered by a mucus hydrogel layer whose structure is static, over which is a thin layer of water from which water is directly exchanged with inhaled and exhaled air. This condensation layer of water will inevitably be thickest following the slow exhalation of relatively warm humid air and thinnest following the rapid inhalation of relatively cool dry air. We assumed a steady-state fully hydrated condensation layer thickness of approximately 1 μm given the water content of supersaturated state of exhaled air during an exhalation into a relatively warm trachea.

As principal air flow in the nasal cavity (approximately 12 cm length from the tip of the nose to the nasal pharynx) occurs in the narrow air passage of the middle or inferior meatus (approximately 0.2 cm radius, or approximately 10 $cm^2$ surface area), we assume relatively quiescent conditions over the majority of ALF surface area within the nose (approximately 160 $cm^2$) over the course of inhalation on normal tidal breathing. Principal air velocity in the trachea (approximately 12 cm length from the larynx to the carina) being driven by the jet of air that emerges from the larynx (with typical peak air velocity on inhalation of approximately 3 m/s), we assume an average velocity on inhalation in the trachea of around 1 m/s. Finally, we assumed salt concentrations in hydrated ALF are approximately equivalent to blood concentrations, such that in the reference state ($C_0$) osmolarity equilibrium has been obtained between the airways and surrounding epithelial cells and vascularized tissues. Table 4 summarizes the approximate total masses of principal salt ions and water in the nose and trachea in a fully hydrated state.

The pore-level model of transport in the mucus hydrogel uses a periodic porous medium hydrodynamic model of osmosis as developed elsewhere. The analysis, while unnecessary in arriving at the predictions shared in the main articles, provides a "first principles view" of the parameters appeared in Eqs (1)-(11), and can be useful in a fuller analysis of interrelated heat and mass transfer, pore structure evolution (shrinking and expanding of the mucus), as well as transport of ion, inflammatory marker and other diffusive constituents of ALF. Mucus is modeled as a porous medium with infinitely long cylindrical pores (i.e., the radius of the pores, R, is much smaller than the length of the pores or the mucus thickness, L). Each pore is identical to the other, and of an effective diameter deduced from the model by comparison of predictions with reports of experimentally measured ALF permeability values. The model explicitly considers salt transport, including the principal cations sodium, calcium, potassium and magnesium. Each of these cations is assumed to have a similar electrostatic potential radius of a, outside of which there is zero potential, and inside of which the potential is infinitely attractive. Ion diffusion through the pores is restricted owing to interaction of the cations with anionic pore walls. In this limiting case of very strong attraction between cations and the anionic hydrogel freely diffusing cations diffuse within a restricted pore of radius R-a, as within the radius of electrostatic interactions they are immediately fixed by electrostatic attraction to the anionic hydrogel and disappear from solution. We deduced the dimensions of the model micro structure of mucus by comparing the formulas derived for permeability, reflection coefficient, and other transport characteristics with measured values of water permeability within hydrated airway mucus.

We determined the values of model parameters in Tables 1 (FIG. 8) and 2 (FIG. 10) by use of the data summarized in Tables 3, FIG. 13 (see also Table S1 for a summary of central airway Weibel geometry). The perturbation analysis by which we determined Eqs (8)-(11).

Figure 14A:
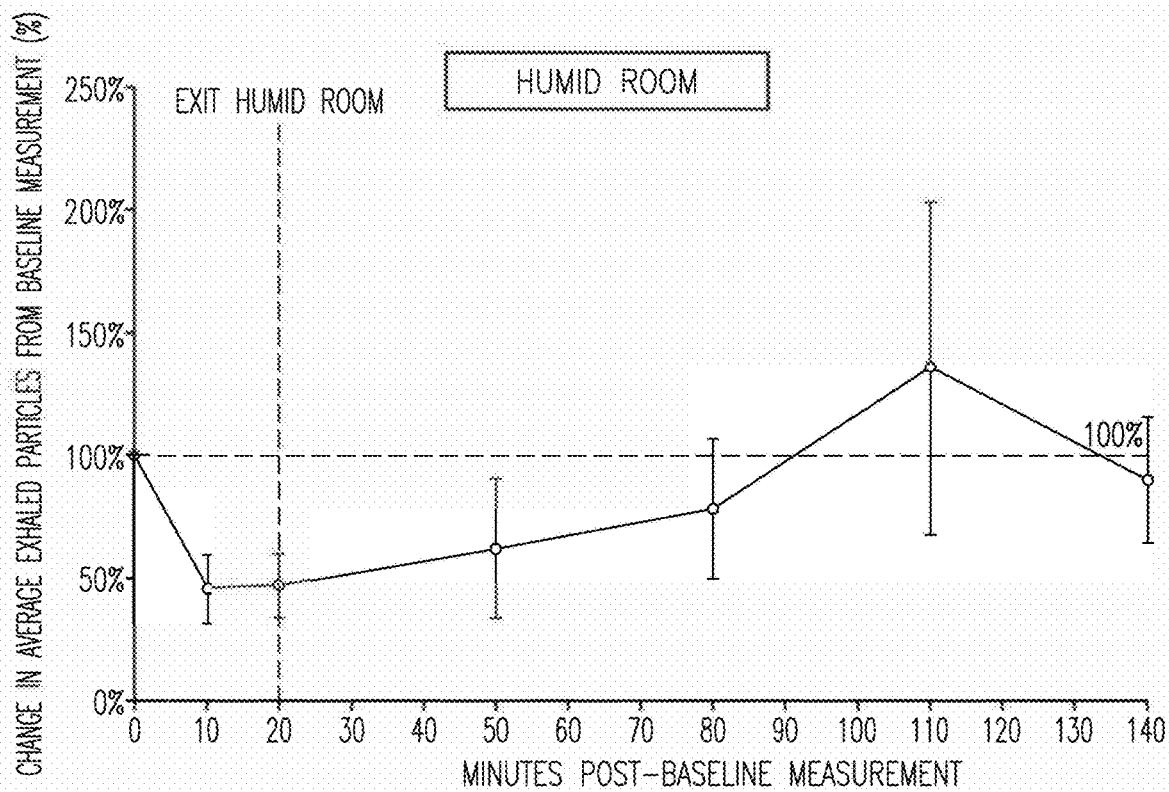
FIG. 14A is a graph showing a percentage change in average exhaled particles from a baseline versus time following entry or exit from a humid room, according to at least one illustrated embodiment.

FIG. 14A is a graph showing a percentage change in average exhaled particles from a baseline versus time following entry or exit from a humid room, according to at least one illustrated embodiment.

Figure 14B:
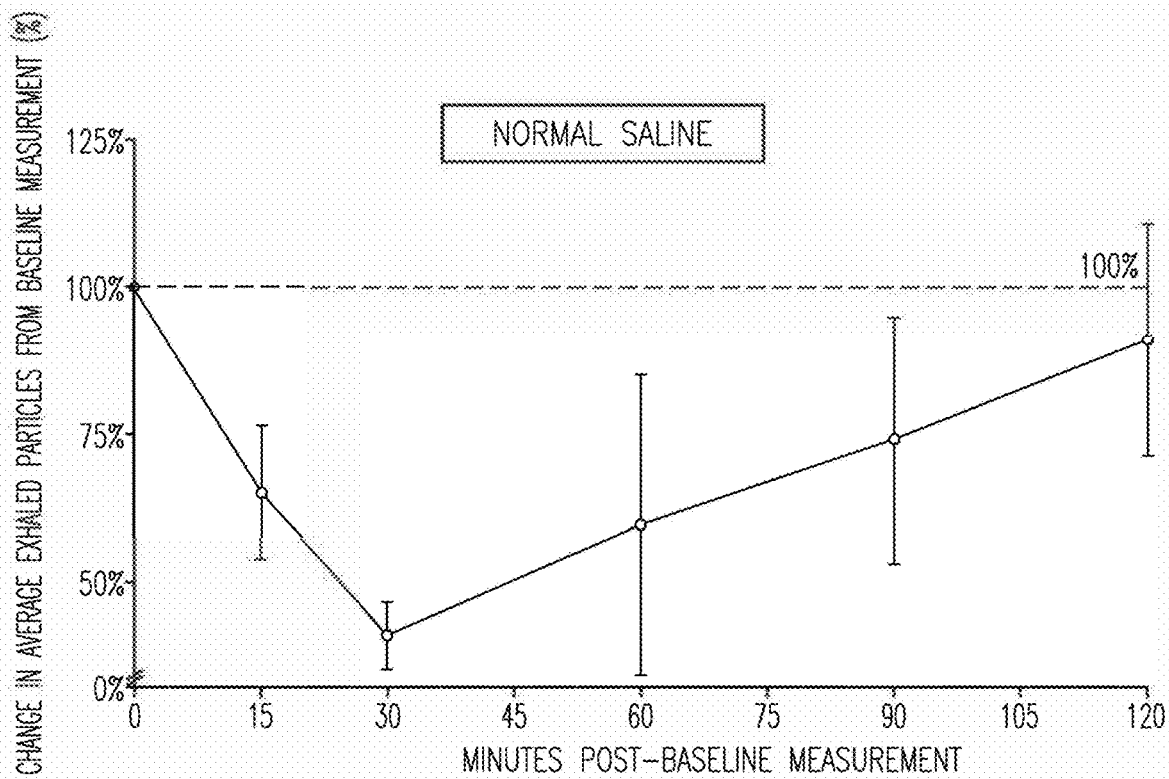
FIG. 14B is a graph showing a percentage change in average exhaled particles from a baseline versus time following delivery of normal saline to the subject, according to at least one illustrated embodiment.

FIG. 14B is a graph showing a percentage change in average exhaled particles from a baseline versus time following delivery of an aerosol of droplets comprising normal saline, the droplets sized to target the upper airways of a subject, according to at least one illustrated embodiment.

Figure 14C:
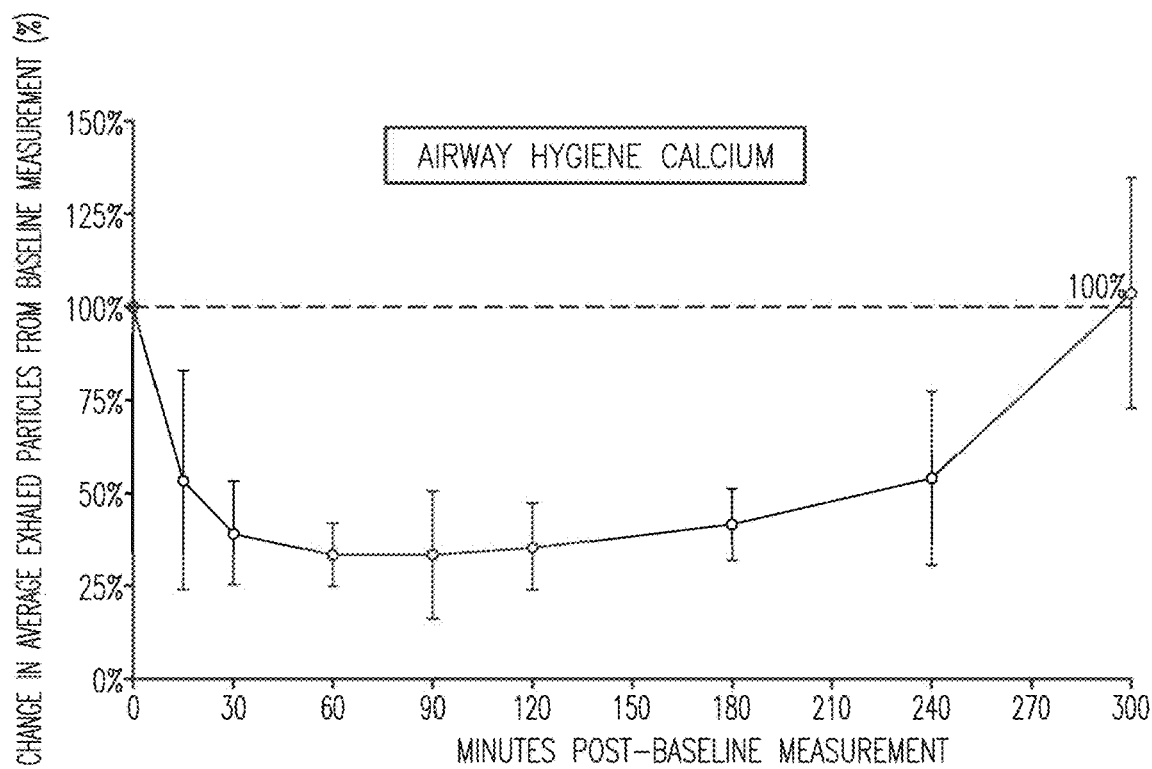
FIG. 14C is a graph showing a percentage change in average exhaled particles from a baseline versus time following delivery of an aerosol of droplets comprising a divalent salt in the form of $CaCl_2$, according to at least one illustrated embodiment.

FIG. 14C is a graph showing a percentage change in average exhaled particles from a baseline versus time following delivery of an aerosol of droplets comprising a divalent salt in the form of $CaCl_2$, the droplets sized to target the upper airways of human subject, according to at least one illustrated embodiment.

Figure 14D:
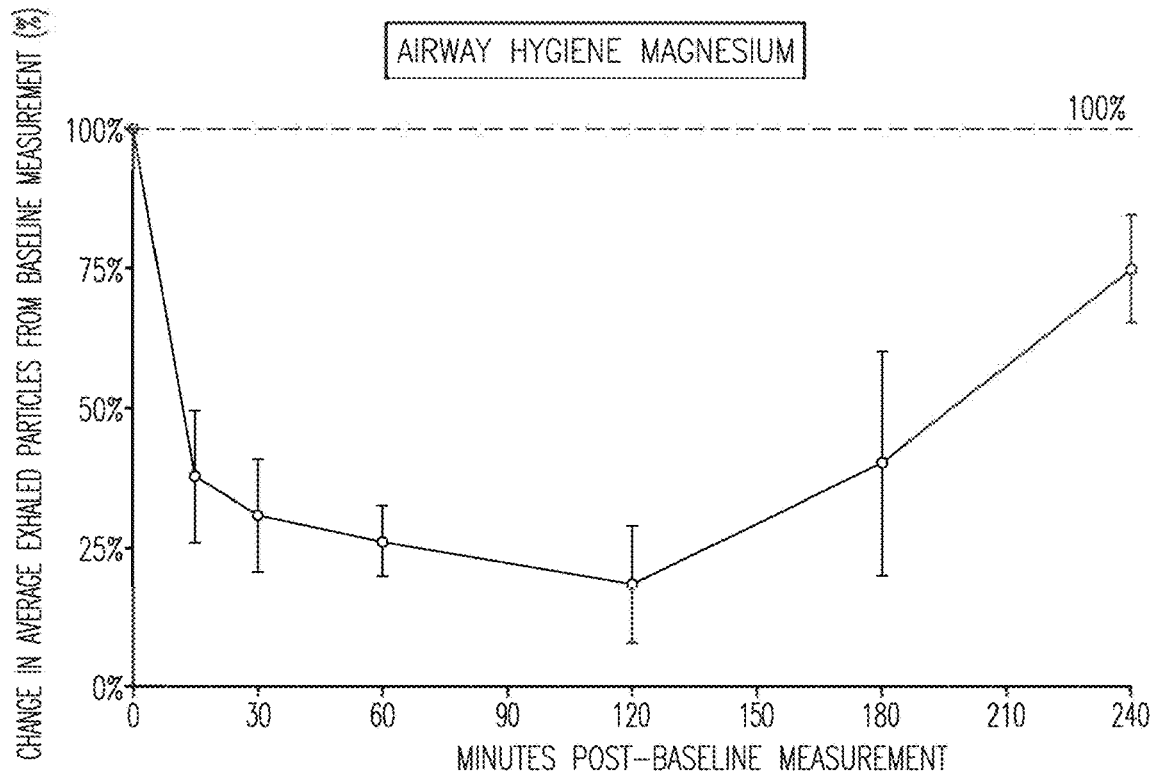
FIG. 14D is a graph showing a percentage change in average exhaled particles from a baseline versus time following delivery of an aerosol of droplets comprising a divalent salt in the form of $Mg\ Cl_2$, according to at least one illustrated embodiment.

FIG. 14D is a graph showing a percentage change in average exhaled particles from a baseline versus time following delivery of an aerosol of droplets comprising a divalent salt in the form of Mg $Cl_2$, the droplets sized to target the upper airways of a human subject, according to at least one illustrated embodiment.

Notably, divalent salts ($CaCl_2$, Mg $Cl_2$) targeting the upper airways hydrate the upper airways for 4-6 hours, while hypertonic saline (NaCl) only hydrates the upper airways for around 1 hour.

Laryngeal hydration by nasal inhalation of divalent salts ($CaCl_2$, Mg $Cl_2$) with a base pH (pH approximately 9 to approximately 10) provides hydration to the upper airways for 4 hours post inhalation, advantageously reducing triggers of chronic cough including ATP and acidity. Such could, for example be employed with a combination therapy with receptor-targeting drugs or pharmaceuticals.

Mucosal vaccines offer the potential to trigger robust protective immune responses at the predominant sites of pathogen infection. Current vaccines delivered by injection have various associated problems such as safety, compliance, morbidity and the relatively high cost of associated with mass immunization. While greater than 90% of pathogens gain access to the body via mucosal sites, injected vaccines typically provide only partial or even no protection at mucosal sites.

Only a handful of mucosal vaccines are currently licensed. This paucity is attributable at least in part to the general lack of effective delivery systems able to preserve vaccine antigen integrity and strong adjuvanticity. The majority of mucosal vaccines are administered by the oral and nasal routes, although other mucosal routes are of course possible. Intranasal delivery effectively induces antibody production in salivary glands, the NALT and the bronchus-associated lymphoid tissue (BALT) of the lower respiratory tract. The route of mucosal immunization should be carefully considered based at least in part on the mucosal sites targeted by different pathogens. In most cases, mucosal vaccination is also effective in priming systemic immune responses and generating serum antibodies with neutralizing properties. Some research suggests that BALT exists in children and adolescents but does not exist in significant amounts in adults. Without being bound by theory, such would suggest that mucosal vaccination may be more effective for children and adolescents if delivered to target the full upper airways rather than just targeting the nose. Various ranges of mean aerodynamic diameters or sizes are described herein that advantageously facilitate such targeting. Such could, for example be used to target respiratory syncytial virus (RSV). The mucosal vaccine can take many forms, for example an antigen vaccine or an RNA vaccine.

Mucosal immunization provides several possible advantages over subcutaneous and intramuscular routes, including protection from localized infection at the site of entry, clearance of organisms on mucosal surfaces, induction of long-term immunity through establishment of central and tissue-resident memory cells, and the ability to shape regulatory responses. Despite these advantages, significant barriers remain to achieving effective mucosal immunization. The epithelium also provides any obstacles to immunization, and the activation of immune recognition and effector pathways that leads to mucosal immunity has been difficult to achieve. Challenges can include controlling variability in delivery and site of deposition and environmental exposure of mucosal tissues. Airway mucosa are exposed constantly to environmental conditions, and notably impact hydration of the upper airways in ways that vary continually. Dehydration of the upper airways is a particular risk as the upper airways humidify inhaled air, with evaporation in proportion to the speed of air flow, especially great from the larynx to the 1st carina. With dehydration of the upper airways (and with lung infection by SARS CoV2, TB), respiratory droplets tend to form in greater numbers. Dehydration of the upper airways (exacerbated by mouth breathing and high minute volume) compresses cilia via mucus displacement to promote high levels of inflammatory cytokines among other markers of inflammation. Other consequence of dehydration include cough reflex. Hydrating the upper airways with hypertonic saline (as is used in the hydrating of the lungs of CF patients) with divalent salts (calcium and magnesium chloride) permits hydration for several hours versus 30 minutes.

Nasal targeted vaccines in principle illicit immune response via nasal associated lymphoid tissue. Depending on mode of delivery and animal/human model, mutual vaccine delivery can lead to significant loss of dose via excretion, or entry of dose into the mouth or the respiratory tract. Bronchus associated lymphoid tissue present in children and adolescents (in humans), but typically not in adults, may play a role in age-related differences in immune resistance and animal/human differences.

The inventors have recognized that at least one barrier can be a pH of tissue to which the mucosal vaccines (e.g., intranasal vaccines) are applied. In particular, many patients or subjects have an acidic pH in the tissues of the nose, larynx and/or trachea. Such can hinder the effectiveness of mucosal vaccines administered via the at least one or a nose, larynx or trachea of the subject. In particular, dehydrated nasal or tracheal airway lining fluid can have dehydrated mucus—which becomes a barrier of transport and therefore immunogenicity. Acidity increases the expression of angiotensin-converting enzyme 2 (ACE2) which presumably alters efficacy of a mucosal vaccine. Hypertonic salines are effective at hydrating the airways, while isotonic salines are not, which is why the former are used in cystic fibrous treatments and not the latter. The inventors have shown that divalent cation (e.g. calcium chloride and/or magnesium chloride) hypertonic salines hydrate the airways longer than monovalent (sodium chloride) salines. The inventors have especially focused on the upper airways as where dehydration is a significant issue.

The inventors have recognized that delivery of a large dose into the nose via droplets that are 50 μm or larger can lead (in animals) to drainage into the lungs while in humans (depending on the position of the head among other factors) to excretion, drainage into the mouth, or post-nasal drip drainage into the trachea). The inventors have also recognized that delivery by breath-activated aerosol (smaller than 8 μm) leads to effective dispersion in the airways, with the smallest MMAD~2 μm most distributed in the small airways. Optimal targeting of NALT, and potential targeting of BALT, is likely achieved by upper airway targeting of aerosol. Recent research suggests optimal coverage of upper airway mucosa achieved by nasal breath-activation of particles or droplets with MMAD in the range of 8 μm to 13 μm, inclusive.

To address such, a laryngeal hydration composition can be administered to at least one or a nose, larynx or trachea of a subject prior to administration of a mucosal vaccine (e.g., delivery of an antigen or an RNA vaccine or influenza vaccine), wherein the laryngeal hydration composition comprising one or more of sodium chloride, calcium chloride, potassium chloride or magnesium chloride. In some implementations, the laryngeal hydration composition can omit sodium chloride.

Administering the laryngeal hydration composition can, for example include administering the laryngeal hydration composition as an aerosol of droplets to at least one or a nose, larynx or trachea via nasal inhalation. Administering the laryngeal hydration composition can, for example, include administering the laryngeal hydration composition as an aerosol of droplets having a pH of 7.0 up to around 10.0, or preferably around 7.5 up to around 9.5, or more preferably around 8.0 up to around 9.0, or even more preferably 8.0 to 8.5 or most preferably around 8.0. Administering the laryngeal hydration composition can, for example, include administering the laryngeal hydration composition as an aerosol of droplets having a pH of around 8.0 up to around 8.5. Administering the laryngeal hydration composition can, for example, include administering the laryngeal hydration composition as an aerosol of droplets having a pH of around 8.0.

Administering the laryngeal hydration composition can, for example, include administering the laryngeal hydration composition as an aerosol of droplets having a having a mass median aerodynamic diameter or size ranging from approximately 8 microns to approximately 15 microns, approximately 9 microns to approximately 13 microns, approximately 9 microns to approximately 12 microns, approximately 8 microns to approximately 13 microns, approximately 8 microns to approximately 12 microns, or alternatively ranging from approximately 15 microns to approximately 500 microns where the head is tilted back to induce post-nasal drip, as measured by laser light scattering. Administering the laryngeal hydration composition can, for example, include administering the laryngeal hydration composition as an aerosol of dry particles salts, the dry particles having a mass median particle size ranging from approximately 8 microns to approximately 15 microns, approximately 9 microns to approximately 13 microns, approximately 9 microns to approximately 12 microns, approximately 8 microns to approximately 13 microns, approximately 8 microns to approximately 12 microns.

Administering the laryngeal hydration composition can, for example, include administering the laryngeal hydration composition as an aerosol of dry particles salts to at least one or a nose, larynx or trachea via nasal inhalation. Administering the laryngeal hydration composition can, for example, include administering the laryngeal hydration composition as an aerosol of dry particles salts and one or more inactive excipients.

Administering the laryngeal hydration composition can, for example include administering the laryngeal hydration composition that comprises approximately 0.9% to approximately 7% total salts by weight of the laryngeal hydration composition. administering the laryngeal hydration composition includes administering the laryngeal hydration composition that comprises approximately 5% total salts by weight of the laryngeal hydration composition. Administering the laryngeal hydration composition can, for example include administering the laryngeal hydration composition that comprises a dose, the dose which is formulated to deliver into a nose or a mouth at least 0.3 mg of total salt or approximately 2.5 mg of total salt.

Administering the laryngeal hydration composition can, for example include delivering into at least one of a nose or a mouth a minimal delivered quantity of approximately 0.3 mg of total salt to deposit a minimal deposited quantity of approximately 0.1 mg of salt to the larynx and other tissue surrounding or in the vicinity of the larynx in a respiratory tract of the subject.

Administering the laryngeal hydration composition can, for example include administering the laryngeal hydration composition that comprises a P2X3 antagonist drug.

Subsequently administering a mucosal vaccination (e.g., delivery of an antigen or an RNA vaccine) via the at least one or a nose, larynx or trachea of the subject can, for example include administering the mucosal vaccination within approximately 4 hours of administering the laryngeal hydration composition to the at least one or a nose, larynx or trachea of the subject, preferably within approximately 3 hours of administering the laryngeal hydration composition to the at least one or a nose, larynx or trachea of the subject; more preferably within approximately 2 hours of administering the laryngeal hydration composition to the at least one or a nose, larynx or trachea of the subject, and most preferably within approximately 1 hour of administering the laryngeal hydration composition to the at least one or a nose, larynx or trachea of the subject.

While generally described in terms of administration to the nose, larynx and/or trachea, such can be employed for mucosal vaccination (e.g., delivery of an antigen or an RNA vaccine) via other mucous membranes so long as the adjustment in pH (e.g., adjusting pH of the vaccination targeted tissue to be approximately neutral) not inconsistent with good health and/or comfort of the subject.

EXAMPLES

Example 1. A laryngeal hydration composition, comprising: water; and a salt-based composition comprising one or more of: sodium chloride, calcium chloride, potassium chloride or magnesium chloride, wherein the laryngeal hydration composition comprising the salt-based composition in the water has a pH of around 7.0 up to around 10.0, or preferably around 7.5 up to around 9.5, or more preferably around 8.0 up to around 9.0, or even more preferably 8.0 to 8.5 or most preferably around 8.0.

Example 2. The laryngeal hydration composition of example 1 wherein the laryngeal hydration composition takes the form of an aerosol of droplets, the droplets having a mass median aerodynamic diameter or size ranging from approximately 8 microns to approximately 15 microns, or preferably approximately 9 microns to approximately 13 microns, approximately 9 microns to approximately 12 microns, approximately 8 microns to approximately 13 microns, approximately 8 microns to approximately 12 microns, or alternatively ranging from approximately 15 microns to approximately 500 microns if to be used in conjunction with a tilting of the head to induce post-nasal drip, the mass median aerodynamic diameter as measured by laser light scattering.

Example 3. The laryngeal hydration composition of example 2 wherein each of the droplets has a pH of around 8.0 to around 8.5.

Example 4A. The laryngeal hydration composition of any of examples 1 through 3 wherein the laryngeal hydration composition omits any preservatives and is stored in a sterile-filled container prior to use. The salt-based composition in the water can be prepared within a sterile-filled container and within an oxygen-free atmosphere to maintain an elevated pH above 7.0.

Example 4B. The laryngeal hydration composition of any of examples 1 through 3 further comprising a buffer, for example one or more of: a bicarbonate buffer, a citrate buffer, or a phosphate buffer.

Example 5. A laryngeal hydration composition, comprising:
  dry particle salts comprising one or more of sodium chloride, calcium chloride, potassium chloride and magnesium chloride the dry particles having a mass median aerodynamic diameter ranging from approximately 9 microns to approximately 15 microns.

Example 6. The laryngeal hydration composition of example 5 wherein the laryngeal hydration composition further comprises at least one of: i) one or more inactive excipients, such as lactose or leucine; or ii) or more drugs.

Example 7. The laryngeal hydration composition of any of examples 1 through 6 wherein the laryngeal hydration composition comprises approximately 0.9% to approximately 10% total salts by weight of the laryngeal hydration composition.

Example 8. The laryngeal hydration composition of any of examples 1 through 7 wherein the laryngeal hydration composition comprises approximately 5% total salts by weight of the laryngeal hydration composition.

Example 9. The laryngeal hydration composition of any of examples 1 through 6 that comprises a dose, the dose which is formulated to deliver into a nose or a mouth at least approximately 0.1 mg of total salt or approximately 5 mg of total salt or approximately 0.3 mg of total salt or approximately 2.5 mg of total salt.

Example 10. The laryngeal hydration composition of any of examples 1 through 6, further comprising:
  a P2X3 antagonist drug.

Example 11. The laryngeal hydration composition of any of examples 1 through 6, further comprising:
  a therapeutic molecule whose therapeutic effect involves the targeting of receptors in the upper airways, such as P2X3, TRPV, or ACE2 receptors.

Example 12. The laryngeal hydration composition of any of examples 1 through 6 wherein the laryngeal hydration composition comprises at least one of calcium chloride or magnesium chloride and omits sodium chloride and potassium chloride.

Example 13. The laryngeal hydration composition of any of examples 1 through 12 wherein the laryngeal hydration composition is administrable to at least one of a larynx or a trachea to reduce a phonation threshold pressure relative to a dehydrated state of an individual having avoided eating, drinking fluids, hydrating the airways or breathing air with relatively humidity of 50% or greater for approximately 2 hours.

Example 14. The laryngeal hydration composition of any of examples 1 through 11 wherein the laryngeal hydration composition is administrable to at least one of a larynx or a trachea to reduce cough incidence, suppress cough reflex, improve voice quality and/or increase pulse oxygen saturation of a subject in a relatively dehydrated state of an individual having avoided eating, drinking fluids, hydrating the airways or breathing air with relatively humidity of 50% or greater for approximately 2 hours.

Example 15. The laryngeal hydration composition of any of examples 1 through 11 wherein administration of the laryngeal hydration composition achieves a reduction of phonation threshold pressure of at least 10% relative to the phonation threshold pressure measured in a relatively dehydrated state of an individual having avoided eating, drinking fluids, hydrating the airways or breathing air with relatively humidity of 50% or greater for approximately 2 hours.

Example 16. A method of reduced phonation threshold pressure, comprising:
- accessing a laryngeal hydration composition, the laryngeal hydration composition comprising one or more of sodium chloride, calcium chloride, potassium chloride or magnesium chloride; and
- administering the laryngeal hydration composition to at least one or a nose, larynx or trachea.

Example 17. The method of example 16 wherein administering the laryngeal hydration composition includes administering the laryngeal hydration composition as an aerosol of droplets to at least one or a nose, larynx or trachea via nasal inhalation.

Example 18. The method of example 16 wherein administering the laryngeal hydration composition includes administering the laryngeal hydration composition as an aerosol of droplets having a pH of 7.0 up to around 10.0, or preferably around 7.5 up to around 9.5, or more preferably around 8.0 up to around 9.0, or even more preferably 8.0 to 8.5 or most preferably around 8.0.

Example 19. The method of example 16 wherein administering the laryngeal hydration composition includes administering the laryngeal hydration composition as an aerosol of droplets having a pH of around 8.0 up to around 8.5.

Example 20. The method of example 16 wherein administering the laryngeal hydration composition includes administering the laryngeal hydration composition as an aerosol of droplets having a pH of around 8.0.

Example 21. The method of any of examples 16 through 20 wherein administering the laryngeal hydration composition includes administering the laryngeal hydration composition as an aerosol of droplets having a mass median aerodynamic diameter or size ranging from approximately 8 microns to approximately 15 microns, approximately 9 microns to approximately 13 microns, approximately 9 microns to approximately 12 microns, approximately 8 microns to approximately 13 microns, approximately 8 microns to approximately 12 microns, or ranging from approximately 15 microns to approximately 500 microns, the mass median aerodynamic diameter as measured by laser light scattering.

Example 22. The method of example 16 wherein administering the laryngeal hydration composition includes administering the laryngeal hydration composition as an aerosol of dry particles salts to at least one or a nose, larynx or trachea via nasal inhalation.

Example 23. The method of example 22 wherein administering the laryngeal hydration composition includes administering the laryngeal hydration composition as an aerosol of dry particles salts and one or more inactive excipients.

Example 24. The method of example 22 wherein administering the laryngeal hydration composition includes administering the laryngeal hydration composition as an aerosol of dry particles salts, the dry particles having a mass median particle size ranging from approximately 8 microns to approximately 12 microns.

Example 25. The method of any of examples 16 through 24 wherein administering the laryngeal hydration composition includes administering the laryngeal hydration composition that comprises approximately 0.9% to approximately 7% total salts by weight of the laryngeal hydration composition.

Example 26. The method of any of examples 16 through 24 wherein administering the laryngeal hydration composition includes administering the laryngeal hydration composition that comprises approximately 5% total salts by weight of the laryngeal hydration composition.

Example 27. The method of any of examples 16 through 24 wherein administering the laryngeal hydration composition includes administering the laryngeal hydration composition that comprises a dose, the dose which is formulated to deliver into a nose or a mouth at least 0.3 mg of total salt or approximately 2.5 mg of total salt.

Example 28. The method of any of examples 16 through 24 wherein administering the laryngeal hydration composition includes administering the laryngeal hydration composition that comprises a P2X3 antagonist drug.

Example 29. The method of any of examples 16 through 24 wherein administering the laryngeal hydration composition includes administering the laryngeal hydration composition that comprises at least one of calcium chloride or magnesium chloride and omits sodium chloride and potassium chloride.

Example 30. The method of any of examples 16 through 29 wherein administering the laryngeal hydration composition includes administering the laryngeal hydration composition to at least one of a larynx or a trachea to reduce a phonation threshold pressure.

Example 31. The method of any of examples 16 through 29 wherein administering the laryngeal hydration composition includes administering the laryngeal hydration composition to a larynx and a trachea via at least one of a nose or a mouth to reduce a phonation threshold pressure.

Example 32. The method of any of examples 16 through 29 wherein administering the laryngeal hydration composition includes administering the laryngeal hydration composition to at least one of a larynx or a trachea to reduce a phonation threshold pressure to reduce or suppress cough incidence, improve voice quality and/or increase pulse oxygen saturation of a subject.

Example 33. The method of any of examples 16 through 29 wherein administering the laryngeal hydration composition achieves a reduction of phonation threshold pressure of at least 10% relative to the phonation threshold pressure measured in a relatively dehydrated state of an individual having avoided eating, drinking fluids, hydrating the airways or breathing air with relatively humidity of 50% or greater for approximately 2 hours.

Example 34. The method of any of examples 16 through 29 used to treat a relatively non-hydrated larynx and trachea of a subject to reduce phonation threshold pressure by at least 10% within 15 minutes of administration, wherein administering the laryngeal hydration composition includes delivering into at least one of a nose or a mouth a minimal delivered quantity of approximately 0.3 mg of total salt to deposit a minimal deposited quantity of approximately 0.1 mg of salt to the larynx and other tissue surrounding or in the vicinity of the larynx in a respiratory tract of the subject.

Example 35. A method of suppressing coughing in a subject, method comprising:
generating an aerosol of droplets, the droplets of the aerosol of droplets each comprising a salt-based composition in water, the salt-based composition comprising sodium chloride, and the droplets have a mass median aerodynamic diameter or size ranging from approximately 8 microns to approximately 15 microns, approximately 9 microns to approximately 13 microns, approximately 9 microns to approximately 12 microns, approximately 8 microns to approximately 13 microns, approximately 8 microns to approximately 12 microns, or ranging from approximately 15 microns to approximately 500 microns, the mass median aerodynamic diameter as measured by laser light scattering; and
administering the aerosol of droplets to at least the nose and larynx of the subject by nasal inhalation to achieve at least one of a prophylactic or a therapeutic effect.

Example 36. The method of example 35, further comprising:
detecting an indication that the subject would benefit from cough suppression, wherein at least the administering the aerosol of droplets to at least a larynx of the subject by nasal inhalation to achieve at least one of a prophylactic or a therapeutic effect is in response to detecting the indication that the subject would benefit from cough suppression.

Example 37. A method of improving voice quality in a subject, method comprising:
generating an aerosol of droplets, the droplets of the aerosol of droplets each comprising a salt-based composition in water, the salt-based composition comprising sodium chloride, and the droplets have a mass median aerodynamic diameter or size ranging from approximately 8 microns to approximately 15 microns, approximately 9 microns to approximately 13 microns, approximately 9 microns to approximately 12 microns, approximately 8 microns to approximately 13 microns, approximately 8 microns to approximately 12 microns, or ranging from approximately 15 microns to approximately 500 microns, the mass median aerodynamic diameter as measured by laser light scattering; and
administering the aerosol of droplets to at least the nose and the larynx of the subject by nasal inhalation to achieve at least one of a prophylactic or a therapeutic effect.

Example 38. The method of example 37, further comprising:
detecting an indication that the subject would benefit from an improvement in voice quality including a schedule vocal performance or an existence or presence of an undesired vocal characteristic in the subject, wherein at least the administering by nasal inhalation the aerosol of droplets to at least the nose and larynx of the subject to achieve at least one of a prophylactic or a therapeutic effect is in response to detecting the indication that the subject would benefit from the improvement in voice quality.

Example 39. A method of increasing pulse oxygen saturation in a subject, method comprising:
generating an aerosol of droplets, the droplets of the aerosol of droplets each comprising a salt-based composition in water, the salt-based composition comprising sodium chloride, and the droplets have a mass median aerodynamic diameter or size ranging from approximately 8 microns to approximately 15 microns, approximately 9 microns to approximately 13 microns, approximately 9 microns to approximately 12 microns, approximately 8 microns to approximately 13 microns, approximately 8 microns to approximately 12 microns, or ranging from approximately 15 microns to approximately 500 microns, the mass median aerodynamic diameter as measured by laser light scattering; and
administering the aerosol of droplets to at least the nose and the larynx of the subject by nasal inhalation to achieve at least one of a prophylactic or a therapeutic effect.

Example 40. The method of example 39, further comprising:
detecting an indication that the subject would benefit from an increase in pulse oxygen saturation, wherein at least the administering the aerosol of droplets to at least a larynx of the subject to achieve at least one of a prophylactic or a therapeutic effect is in response to detecting the indication that the subject would benefit from the increase in pulse oxygen saturation.

Example 41. The method of any of examples 35 through 40, further comprising:
determining that the larynx of the subject is dehydrated, and wherein at least the administering the aerosol of droplets to at least a larynx of the subject to achieve at least one of a prophylactic or a therapeutic effect is in response to determining that the subject is dehydrated.

Example 42. The method of any of examples 35 through 40, further comprising:
determining that the subject is participating or will participate in a dehydrating activity, and wherein at least the administering the aerosol of droplets to at least a larynx of the subject to achieve at least one of a prophylactic or a therapeutic effect is in response to determining that the subject is participating in or will participate in the dehydrating activity.

Example 43. The method of any of examples 35 through 40, further comprising:
determining that the subject has an ailment, and wherein at least the administering the aerosol of droplets to at least a larynx of the subject to achieve at least one of a prophylactic or a therapeutic effect is in response to determining that the subject has the ailment.

Example 44. The method of any of examples 35 through 40 wherein administering the aerosol of droplets to at least a larynx of the subject to achieve at least one of a prophylactic or a therapeutic effect includes administering the aerosol of droplets to at least a larynx of the subject to achieve a delivery of at least 0.1 mg mass of salt.

Example 45. The method of any of examples 35 through 40 wherein administering the aerosol of droplets to at least a larynx of the subject to achieve at least one of a prophylactic or a therapeutic effect includes administering the aerosol of droplets to at least a larynx of the subject to achieve a delivery of from 0.1 mg to 4.0 mg mass of salt.

Example 46. The method of any of examples 35 through 40 wherein generating an aerosol of droplets includes generating the aerosol of droplets in a space from which the aerosol is naturally inspirable by the subject via a nose of the subject without any application of force beyond an inhalation by the subject.

Example 47. The method of any of examples 35 through 40 wherein administering the aerosol of droplets to at least a larynx of the subject to achieve at least one of a prophylactic or a therapeutic effect includes making the aerosol of droplets available for natural inspiration by the subject via a nose of the subject without any application of force beyond an inhalation by the subject.

Example 48. The method of any of examples 35 through 47 wherein generating an aerosol of droplets includes generating the aerosol of droplets wherein the salt-based composition further comprises one, more, or all of calcium chloride, magnesium chloride, and potassium chloride along with the sodium chloride.

Example 49. The method of any of examples 35 through 48 wherein generating an aerosol of droplets comprises generating an aerosol of droplets wherein each of the droplets comprise greater than 0.9% by weight of the droplet of the salt-based composition.

Example 50. The method of any of examples 35 through 48 wherein generating an aerosol of droplets comprises generating an aerosol of droplets wherein each of the droplets comprise greater than 1% by weight of the droplet of the salt-based composition.

Example 51. The method of any of examples 35 through 50 wherein generating an aerosol of droplets comprises generating an aerosol of droplets wherein the droplets have a mass median aerodynamic diameter or size ranging from 9 microns to 10 microns.

Example 52. The method of any of examples 35 through 50 wherein generating an aerosol of droplets comprises generating an aerosol of droplets wherein the droplets have a mass median aerodynamic diameter or size of approximately 15 microns, with a standard deviation of 2 microns or less.

Example 53. The method of any of examples 35 through 50 wherein generating an aerosol of droplets comprises generating an aerosol of droplets wherein the droplets have a mass median aerodynamic diameter or size ranging from 8 microns to 12 microns, with a standard deviation of 2 microns or less.

Example 54. The method of any of examples 35 through 50 wherein generating an aerosol of droplets comprises generating an aerosol of droplets wherein a majority of the droplets have an aerodynamic diameter or size between 9 microns and 10 microns in diameter.

Example 55. The method of any of examples 35 through 50 wherein generating an aerosol of droplets comprises generating an aerosol of droplets wherein a majority of the droplets have an aerodynamic diameter or size of approximately 11 microns in diameter.

Example 56. The method of any of examples 17 through 22 wherein administering the aerosol of droplets to at least a larynx of the subject by nasal or oral inhalation include administering the aerosol of droplets with a head of the subject in an upright position, not tilted back.

Example 57. The method of any of examples 35 through 50 wherein the droplets have a mass median aerodynamic diameter or size ranging from approximately 20 microns to approximately 500 microns and wherein administering the aerosol of droplets to at least a larynx of the subject by nasal or oral inhalation include administering the aerosol of droplets with a head of the subject in tilted back position.

Example 58. The method of any of examples 35 through 50 wherein the droplets have a mass median aerodynamic diameter or size ranging from approximately 20 microns to approximately 500 microns and wherein administering the aerosol of droplets to at least a larynx of the subject by nasal or oral inhalation include administering the aerosol of droplets with the subject a prone position.

Example 59. The method of any of examples 35 through 50, further comprising:
slowing down a velocity of the aerosol relative to a velocity of the aerosol as it leaves a dispenser and from which the aerosol becomes relatively quiescent.

Example 60. The method of any of examples 35 through 50 wherein generating an aerosol of droplets comprises generating the aerosol via one of an oscillating screen nebulizer or a spray pump with a plurality of apertures on the order of microns in size for a defined period of time in response to an activation event, and ceasing the generating after the defined period of time until a subsequent activation event.

Example 61. The method of any of examples 35 through 50 wherein generating an aerosol of droplets comprises generating the aerosol of droplets where the droplets further comprise:
a benzalkonium chloride preservative, or
an acid in an amount sufficient to reduce the pH of the salt-based composition to about 2 to about 3.

Example 62. The method of any of examples 35 through 60 wherein generating an aerosol of droplets comprises generating the aerosol of droplets from a sterile fill reservoir of the salt-based composition in water without any preservatives and with a pH of at least 7.0.

Example 63. The method of any of examples 35 through 62 wherein generating an aerosol of droplets includes generating an aerosol of droplets having a pH of 7.0 up to around 10.0, or preferably around 7.5 up to around 9.5, or more preferably around 8.0 up to around 9.0, or even more preferably 8.0 to 8.5 or most preferably around 8.0.

Example 64. A composition of an aerosol of droplets for delivery to a nose and a larynx, each droplet comprising:
water; and;
from about 0.9% to about 10% by weight of the droplet of a salt-based composition, the salt-based composition comprising sodium chloride; and
wherein the droplets have a mass median aerodynamic diameter or size ranging from approximately 8 microns to approximately 12 microns or ranging from approximately 20 microns to approximately 500 microns.

Example 65. The composition of example 64 wherein the droplets each comprise about 3% by weight of the droplet to about 10% by weight of the droplet of the salt-based composition.

Example 66. The composition of example 64 wherein the droplets each comprise about 4% by weight of the droplet to about 5% by weight of the droplet of the salt-based composition.

Example 67. The composition of any of examples 64 through 66 wherein the salt-based composition further comprises one, more or all of: calcium chloride, magnesium chloride, and potassium chloride.

Example 68. The composition of any of examples 64 through 67 wherein the droplets have a mass median aerodynamic diameter or size ranging from 9 microns to 10 microns.

Example 69. The composition of any of examples 64 through 67 wherein the droplets have a mass median aerodynamic diameter or size of approximately 11 microns, with a standard deviation of 2 microns or less.

Example 70. The composition of any of examples 64 through 67 wherein the droplets have a mass median aerodynamic diameter or size ranging from 8 microns to 12 microns, with a standard deviation of 1 micron or less.

Example 71. The composition of any of examples 64 through 67 wherein a majority of the droplets have an aerodynamic diameter or size of approximately 11 microns in diameter.

Example 72. The composition of any of examples 64 through 67 wherein a majority of the droplets have an aerodynamic diameter or size from about 20 microns to about 500 microns in diameter.

Example 73. The composition of any of examples 64 through 72 wherein the droplets each further comprises a preservative selected from the group consisting of benzalkonium chloride, benzoic acid, and benzoyl alcohol.

Example 74. The composition of example 73, wherein the preservative is benzalkonium chloride, and the benzalkonium chloride is present in an amount ranging from about 0.05% by weight of the droplet to about 0.2% by weight of the droplet.

Example 75. The composition of example 74 wherein the composition is sterile fill and is free of any preservative other than the sodium chloride, calcium chloride, potassium chloride or magnesium chloride.

Example 76. The composition of any of examples 64 through 72 wherein the composition is in the form of a 0.5 mg to 30 mg dosage.

Example 77. A laryngeal hydration composition to: reduce phonation threshold pressure, suppress coughing, increase blood oxygen saturation and/or improve voice characteristics in a subject, in response to one or more indications of such, wherein the laryngeal hydration composition comprises a therapeutically effective amount of one or more of sodium chloride, calcium chloride, potassium chloride or magnesium chloride.

Example 78. The laryngeal hydration composition of example 77 wherein the laryngeal hydration composition comprises a therapeutically effective amount of one or more divalent salts.

Example 79. The laryngeal hydration composition of example 77 wherein the laryngeal hydration composition comprises a therapeutically effective amount of one or more divalent salts and omits other salts.

Example 80. The laryngeal hydration composition of example 77 wherein the laryngeal hydration composition is free of any preservative other than the sodium chloride, calcium chloride, potassium chloride or magnesium chloride.

Example 81. The laryngeal hydration composition of any of examples 77 through 80 wherein the laryngeal hydration composition has a pH of 7.0 up to around 10.0, or preferably around 7.5 up to around 9.5, or more preferably around 8.0 up to around 9.0, or even more preferably 8.0 to 8.5 or most preferably around 8.0.

Example 82. A composition to: treat negative consequences of acidity that are associated with one or more disorders or diseases (e.g., gastrointestinal esophageal reflux disease, or asthma), in response to one or more indications of such, wherein the composition comprises water and a therapeutically effective amount of a salt-based composition comprising one or more of: sodium chloride, calcium chloride, potassium chloride or magnesium chloride, wherein the salt-based composition in the water has a pH selected to increase a pH of a larynx and/or tissue proximate the larynx of a subject (e.g., to achieve an approximately neutral pH or higher pH).

Example 83. The composition of example 82 wherein the composition comprises a therapeutically effective amount of one or more divalent salts.

Example 84. The composition of example 82 wherein the composition comprises a therapeutically effective amount of one or more divalent salts and omits other salts.

Example 85. The composition of example 82 wherein the composition comprises an aerosol of droplets and is delivered from a sterile-filled container with a pH selected to increase a pH of the larynx and/or tissue proximate the larynx of the subject. In some implementations the composition is free of any preservative other than the sodium chloride, calcium chloride, potassium chloride or magnesium chloride. The composition can optionally include a buffer, for example a bicarbonate buffer, a citrate buffer or a phosphate buffer to increase the pH of the salt-based composition in the water and/or to increase a pH of a larynx and/or tissue proximate the larynx of a subject.

Example 86. The composition of any of examples 82 through 85 wherein the composition has a pH of 7.0 up to around 10.0, or preferably around 7.5 up to around 9.5, or more preferably around 8.0 up to around 9.0, or even more preferably 8.0 to 8.5 or most preferably around 8.0.

Example 87. A laryngeal hydration composition to: reduce phonation threshold pressure, suppress coughing, increase blood oxygen saturation and/or improve voice characteristics in a subject, in response to one or more indications of such, wherein the composition comprises a therapeutically effective amount of an osmolitically active composition, for example, including large sugars, for instance mannitol, sorbitol, or trehalose alone or in any combination.

Example 88. The laryngeal hydration composition of example 87 wherein the composition takes the form of an aerosol of droplets having a mass median aerodynamic diameter or size ranging from approximately 8 microns to approximately 12 microns or ranging from approximately 15 microns to approximately 500 microns as measured by laser light scattering.

Example 89. A composition to treat negative consequences of acidity that are associated with one or more disorders or diseases (e.g., gastrointestinal esophageal reflux disease), in response to one or more indications of such, wherein the composition comprises a therapeutically effective amount of an osmolitically active composition, for example, including large sugars, for instance mannitol, sorbitol, or trehalose alone or in any combination to increase a pH of a larynx and/or tissue proximate the larynx of a subject (e.g., to achieve an approximately neutral pH or a higher pH).

Example 90. The composition of example 89 wherein the composition takes the form of an aerosol of droplets having a having a mass median aerodynamic diameter or size ranging from approximately 8 microns to approximately 12 microns or ranging from approximately 15 microns to approximately 500 microns as measured by laser light scattering.

Example 91. A composition according to any of examples 1 through 15 or 64 through 90 for use in hydrating at least one of a larynx or trachea of a subject.

Example 92. A composition according to any of examples 1 through 15 or 64 through 90 for use in reducing a phonation threshold pressure of a larynx and/or tissue proximate the larynx of a subject.

Example 93. A composition according to any of examples 1 through 15 or 64 through 90 for use in adjusting a pH of a larynx and/or tissue proximate the larynx of a subject.

Example 94. A composition according to any of examples 1 through 15 or 64 through 90 for use in adjusting a pH of a larynx and/or tissue proximate the larynx of a subject to achieve an approximately neutral pH or a higher pH than neutral.

Example 95A. A composition according to any of examples 1 through 15 or 64 through 90 for use in treating gastrointestinal esophageal reflux disease.

Example 95B. A composition according to any of examples 1 through 15 or 64 through 90 for use in treating asthma.

Example 96. A composition according to any of examples 1 through 15 or 64 through 90 for use in preparing at least one of a larynx, trachea or nose of a subject for a mucosal vaccination (e.g., delivery of an antigen or an RNA vaccine).

Example 97. A composition according to any of examples 1 through 15 or 64 through 90 for use in enhancing an effectiveness of a mucosal vaccination (e.g., delivery of an antigen or an RNA vaccine).

Example 98. A method of reduced phonation threshold pressure, comprising:
administering a laryngeal hydration composition to at least one or a nose, larynx or trachea of a subject, the laryngeal hydration composition comprising one or more of sodium chloride, calcium chloride, potassium chloride or magnesium chloride; and
subsequently administering a mucosal vaccination (e.g., delivery of an antigen or an RNA vaccine) via the at least one or a nose, larynx or trachea of the subject.

Example 99. The method of example 98 wherein administering the laryngeal hydration composition includes administering the laryngeal hydration composition as an aerosol of droplets to at least one or a nose, larynx or trachea via nasal inhalation.

Example 100. The method of example 98 wherein administering the laryngeal hydration composition includes administering the laryngeal hydration composition as an aerosol of droplets having a pH of 7.0 up to around 10.0, or preferably around 7.5 up to around 9.5, or more preferably around 8.0 up to around 9.0, or even more preferably 8.0 to 8.5 or most preferably around 8.0.

Example 101. The method of example 98 wherein administering the laryngeal hydration composition includes administering the laryngeal hydration composition as an aerosol of droplets having a pH of around 8.0 up to around 8.5.

Example 102. The method of example 98 wherein administering the laryngeal hydration composition includes administering the laryngeal hydration composition as an aerosol of droplets having a pH of around 8.0.

Example 103. The method of any of examples 98 through 102 wherein administering the laryngeal hydration composition includes administering the laryngeal hydration composition as an aerosol of droplets having a having a mass median aerodynamic diameter or size ranging from approximately 8 microns to approximately 15 microns, approximately 9 microns to approximately 13 microns, approximately 9 microns to approximately 12 microns, approximately 8 microns to approximately 13 microns, approximately 8 microns to approximately 12 microns, or ranging from approximately 15 microns to approximately 500 microns, the mass median aerodynamic diameter as measured by laser light scattering.

Example 104. The method of example 98 wherein administering the laryngeal hydration composition includes administering the laryngeal hydration composition as an aerosol of dry particles salts to at least one or a nose, larynx or trachea via nasal inhalation.

Example 105. The method of example 104 wherein administering the laryngeal hydration composition includes administering the laryngeal hydration composition as an aerosol of dry particles salts and one or more inactive excipients.

Example 106. The method of example 104 wherein administering the laryngeal hydration composition includes administering the laryngeal hydration composition as an aerosol of dry particles salts, the dry particles having a mass median particle size ranging from approximately 8 microns to approximately 12 microns.

Example 107. The method of any of examples 98 through 106 wherein administering the laryngeal hydration composition includes administering the laryngeal hydration composition that comprises approximately 0.9% to approximately 7% total salts by weight of the laryngeal hydration composition.

Example 108. The method of any of examples 98 through 106 wherein administering the laryngeal hydration composition includes administering the laryngeal hydration composition that comprises approximately 5% total salts by weight of the laryngeal hydration composition.

Example 109. The method of any of examples 98 through 106 wherein administering the laryngeal hydration composition includes administering the laryngeal hydration composition that comprises a dose, the dose which is formulated to deliver into a nose or a mouth at least 0.3 mg of total salt or approximately 2.5 mg of total salt.

Example 110. The method of any of examples 98 through 106 wherein administering the laryngeal hydration composition includes administering the laryngeal hydration composition that comprises a P2X3 antagonist drug.

Example 111. The method of any of examples 98 through 106 wherein administering the laryngeal hydration composition includes administering the laryngeal hydration composition that comprises at least one of calcium chloride or magnesium chloride and omits sodium chloride and potassium chloride.

Example 112. The method of any of examples 98 through 111 wherein administering the laryngeal hydration composition includes administering the laryngeal hydration composition to at least one of a larynx or a trachea to reduce a phonation threshold pressure.

Example 113. The method of any of examples 98 through 111 wherein administering the laryngeal hydration composition includes administering the laryngeal hydration composition to a larynx and a trachea via at least one of a nose or a mouth to reduce a phonation threshold pressure.

Example 114. The method of any of examples 98 through 111 wherein administering the laryngeal hydration composition includes administering the laryngeal hydration composition to at least one of a larynx or a trachea to reduce a phonation threshold pressure to reduce or suppress cough incidence, improve voice quality and/or increase pulse oxygen saturation of a subject.

Example 115. The method of any of examples 98 through 111 wherein administering the laryngeal hydration composition achieves a reduction of phonation threshold pressure of at least 10% relative to the phonation threshold pressure measured in a relatively dehydrated state of an individual having avoided eating, drinking fluids, hydrating the airways or breathing air with relatively humidity of 50% or greater for approximately 2 hours.

Example 116. The method of any of examples 98 through 111 used to treat a relatively non-hydrated larynx and trachea of a subject to reduce phonation threshold pressure by at least 10% within 15 minutes of administration, wherein administering the laryngeal hydration composition includes delivering into at least one of a nose or a mouth a minimal delivered quantity of approximately 0.3 mg of total salt to deposit a minimal deposited quantity of approximately 0.1 mg of salt to the larynx and other tissue surrounding or in the vicinity of the larynx in a respiratory tract of the subject.

Example 117. The method of any of examples 98 through 111 wherein subsequently administering a mucosal vaccination (e.g., delivery of an antigen or an RNA vaccine) via the at least one or a nose, larynx or trachea of the subject includes administering the mucosal vaccination within approximately 4 hours of administering the laryngeal hydration composition to the at least one or a nose, larynx or trachea of the subject, preferably within approximately 3 hours of administering the laryngeal hydration composition to the at least one or a nose, larynx or trachea of the subject; more preferably within approximately 2 hours of administering the laryngeal hydration composition to the at least one or a nose, larynx or trachea of the subject, and most preferably within approximately 1 hour of administering the laryngeal hydration composition to the at least one or a nose, larynx or trachea of the subject.

Applicants incorporate by reference the following: U.S. provisional patent application Ser. No. 62/687,970, filed Jun. 21, 2018; U.S. provisional patent application Ser. No. 62/652,069, filed Apr. 3, 2018; U.S. provisional patent application Ser. No. 62/628,395, filed Feb. 9, 2018; U.S. provisional patent application Ser. No. 62/556,974, filed Sep. 11, 2017; U.S. provisional patent application Ser. No. 62/727,123, filed Sep. 5, 2018; U.S. nonprovisional patent application Ser. No. 16/122,673, filed Sep. 5, 2018 (published as US2019-0105460); U.S. provisional patent application Ser. No. 63/048,421, filed Jul. 6, 2020; U.S. provisional patent application Ser. No. 63/121,448, filed Dec. 12, 2020; U.S. provisional patent application Ser. No. 63/130,099, filed Dec. 23, 2020; U.S. patent application Ser. No. 17/139,401, filed Dec. 31, 2020; International patent application Serial No. PCT/US2018/050250 (published as WO 2019/051403); International patent application Serial No. PCT/US2021/040331; U.S. provisional patent application Ser. No. 63/297,927, filed Jan. 10, 2022; U.S. provisional patent application Ser. No. 63/401,948, filed Aug. 29, 2022; U.S. patent application Ser. No. 63/324,461, filed on Mar. 28, 2022; U.S. patent application Ser. No. 63/331,398, filed on Apr. 15, 2022; U.S. patent application Ser. No. 63/395,926, filed on Aug. 8, 2022; U.S. patent application Ser. No. 63/401,948, filed on Aug. 29, 2022; U.S. provisional patent application Ser. No. 63/425,450, filed Nov. 15, 2022; and U.S. patent application Ser. No. 63/428,622, filed on Nov. 29, 2022.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A method of reducing coughing in an individual comprising administering by inhalation by the individual aerosolized droplets having a mass median aerodynamic diameter of between 8 and less than 15 microns of a sterile aqueous salt solution having a pH adjusted with a pH adjusting agent to between 7.5 and 10 and consisting of the pH adjusting agent and between 2% and 7% by weight of salt selected from the group consisting of $CaCl_2$), $MgCl_2$ and combinations thereof, in water.

2. The method of claim 1 wherein the salt is $CaCl_2$).

3. The method of claim 1 wherein the salt is $MgCl_2$.

4. The method of claim 1 wherein the salt is both $CaCl_2$) and $MgCl_2$.

5. The method of claim 1 wherein the droplets are formed at the time of administration using a sterile-filled aerosolization device.

6. The method of claim 1 wherein the salt is in the aqueous solution in a concentration between 4% and 5% by weight.

7. The method of claim 1 wherein the pH of the sterile aqueous salt solution is between 7.5 and 9.5.

8. The method of claim 7 wherein the pH is between 8 and 9.

9. The method of claim 1 wherein the pH adjusting agent is a pH buffering agent.

10. The method of claim 9 wherein the pH buffering agent is a bicarbonate, citrate or phosphate buffer.

11. The method of claim 1 wherein the droplets are between 9 and 14 microns in diameter.

12. The method of claim 1 wherein the droplets are formed using a spray pump comprising a droplet forming nozzle.

13. The method of claim 1 comprising administering with the sterile aqueous salt solution an additional therapeutic or active agent.

14. The method of claim 13 wherein the therapeutic agent is selected from the group of molecules targeting receptors in the upper airways.

15. The method of claim 14 wherein the receptors are selected from the group consisting of P2X3, TRPV, and ACE2 receptors.

* * * * *